(12) United States Patent
Ogbu et al.

(10) Patent No.: US 7,053,214 B2
(45) Date of Patent: May 30, 2006

(54) β-SHEET MIMETICS AND COMPOSITION AND METHODS RELATING THERETO

(75) Inventors: Cyprian O. Ogbu, Burlington, MA (US); Hwa-Ok Kim, Lexington, MA (US); Mark A Blaskovich, Bellevue, WA (US)

(73) Assignee: Myriad Genetics, Inc., Salt Lake City, UT (US)

( * ) Notice: Subject to any disclaimer, the term of this patent is extended or adjusted under 35 U.S.C. 154(b) by 181 days.

(21) Appl. No.: 10/367,575

(22) Filed: Feb. 14, 2003

(65) Prior Publication Data

US 2004/0014763 A1 Jan. 22, 2004

Related U.S. Application Data

(60) Provisional application No. 60/357,261, filed on Feb. 14, 2002.

(51) Int. Cl.
C07D 487/04 (2006.01)
A61K 31/5025 (2006.01)
A61P 11/06 (2006.01)

(52) U.S. Cl. .................. 544/236; 514/183; 514/221; 514/248; 540/473; 540/568

(58) Field of Classification Search .............. 514/183, 514/221, 248; 540/473, 568; 544/236
See application file for complete search history.

(56) References Cited

U.S. PATENT DOCUMENTS

| | | | |
|---|---|---|---|
| 4,307,094 A | 12/1981 | Hassall et al. | 424/250 |
| 4,479,937 A | 10/1984 | Sato et al. | 424/99 |
| 4,704,359 A | 11/1987 | Matsuo | 435/69 |
| 4,767,871 A | 8/1988 | Holmes et al. | 548/365 |
| 4,885,023 A | 12/1989 | Yamaguchi et al. | 544/255 |
| 5,049,181 A | 9/1991 | Pissiontas et al. | 71/90 |
| 5,180,418 A | 1/1993 | Pissiotas et al. | 504/193 |
| 5,552,400 A | 9/1996 | Dolle | 514/221 |
| 5,756,466 A | 5/1998 | Bemis | 514/18 |
| 6,020,331 A | 2/2000 | Kahn | 514/221 |
| 6,034,066 A | 3/2000 | Johnson | 514/18 |
| 6,117,896 A | 9/2000 | Qabar et al. | 514/384 |
| 6,245,764 B1 | 6/2001 | Kahn et al. | 514/248 |
| 6,372,744 B1 | 4/2002 | Qabar et al. | 514/248 |
| 6,586,426 B1 | 7/2003 | Kahn | 514/230.5 |

FOREIGN PATENT DOCUMENTS

| | | |
|---|---|---|
| CA | 593525 | 3/1960 |
| DE | 228812 | 10/1985 |
| DE | 3813884 | 11/1989 |
| EP | 104484 | 4/1984 |
| EP | 370955 | 5/1990 |
| EP | 599 444 A1 | 6/1994 |
| EP | 743 319 A1 | 11/1996 |
| JP | 59-172491 | 9/1984 |
| JP | 01-121290 | 5/1989 |
| WO | WO 93/16103 | 8/1993 |
| WO | WO 93/23403 | 11/1993 |
| WO | WO 94/10193 | 5/1994 |
| WO | WO 95/33751 | 12/1995 |
| WO | WO 95/35308 | 12/1995 |
| WO | WO 96/19483 | 6/1996 |
| WO | WO 99/41276 | 8/1999 |
| WO | WO 9941276 A1 * | 8/1999 |

OTHER PUBLICATIONS

Bruce E. Maryanoff, J. Med. Chem.; 2004; 47(4) pp. 769-787.*
William M. Abraham , Am J Physiol Lung Cell Mol Physiol 282: L193-L196, 2002.*
Tremaine WJ, Brzezinski A, Katz JA, Wolf DC, Fleming TJ, Mordenti J, Strenkoski-Nix LC, Kurth MC, Aliment Pharmacol Ther. Mar. 2002;16(3):407-13.*
Rodina, L. L.; Lorkina, A. V.; Korobitsyna, I. K. (USSR). Zhurnal Organicheskoi Khimii, 18(9), 1986-93 (Russian) 1982.*
G H Caughey, J Clin Invest. Feb. 15, 1996; 97(4): 895-896.*
Derwent World Patent Index abstract, "Hexa:hydro pyidazine or di:aza-norbornane di carbox:imide prepn—by cyclising . . . " Accession No. 86-048750, 1986. See also DD228812.
Derwent World Patent Index abstract, "2,3,5,8-Tetra:hydro-1H-(1,2,4)-tri:azolo-1,2-a) pyridazine derives.—selective herbicides used against grasses . . .," Accession No. 89-340639, 1989. See also DE 3813884.

(Continued)

*Primary Examiner*—Thomas C. McKenzie
(74) *Attorney, Agent, or Firm*—Andrew Gibbs; Jay Z. Zhang; Myriad IP Department

(57) ABSTRACT

Compounds having the following structure:

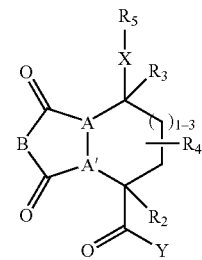

including pharmaceutically acceptable salts and stereoisomers thereof, wherein A, A', B, X, Y, $R_2$, $R_3$, $R_4$ and $R_5$ are as defined herein. Such compounds have utility over a wide range of applications, including use as diagnostic and therapeutic agents. In particular, compounds of this invention, and pharmaceutical compositions containing such compounds, are tryptase antagonists.

30 Claims, No Drawings

OTHER PUBLICATIONS

Adam et al., "Determination of theTriplet Lifetimes of 1,3-Cyclopentadiyl Biradicals Derived from the Photodenitrogenation of Azoalkanes with Time-Resolved Photoacoustic Calorimetry," *J. Org. Chem.*58: 1477-1482, 1993.

Derwent World Patent Index abstract, "New 4-phenyl-urazole derives.—used as herbicide in upland and paddy fields by soil or foliage treatment," Accession No. 84-279285, 1985. See also JP 59-172491.

Derwent World Patent Index abstract, "Tetra:hydro-triazolo-pyrdazine-3-thioxo-1(2H)-one deriv.—used as herbicides . . . ," Accession No. 89-182807, 1989. See also JP 01-121290.

Allen et al., "Molecular Modeling Of γ-Lactam Analogues of β-Lactam Antibacterial Agents: Synthesis And Biological Evaluation Of Selected Penem And Carbapenem Analogues," *Tetrahedron* 45 (7): 1905-1928, 1989.

Aspinall et al., "Enhanced Discrimination by Aza Dienophiles over their Olefinic Counterparts for the Diastereotopic Faces of Methyl (E,E)-5-(2', 3', 4', 6'-Tetra-o-acetyl-β- D-glucopyranosyloxy)penta-2,4-dienoate," *Tetrahedron Letters* 35(20): 3397-3400, 1994.

Attwood et al., "The Design and Synthesis of the Angiotensin Converting Enzyme Inhibitor Cilazapril and Related Bicyclic Compounds," *J. Chem. Soc. Perkin Trans. I* : 1011-1019, 1986.

Baldwin and Lee, "Synthesis Of Bicyclic γ-Lactams Via Oxazolidinones," *Tetrahedron* 42 (23): 6551-6554, 1986.

Baldwin et al., "γ-Lactam Analogues Of β-Lactam Antibiotics," *The Journal of Antibiotics* 44(1): 1-24, 1991.

Baldwin et al., "γ-Lactam Analogues Of Penicillanic and Carbapenicillanic Acids," *J. Chem. Soc., Chem. Commun.* 5:250-252, 1983.

Baldwin et al., "γ-Lactam Analogues Of Penicillanic and Carbapenicillanic Acids," *Tetrahedron* 40(21): 4513-4525, 1984.

Baldwin et al., "γ-Lactam Formation from Tripeptides with Isopenicillin N Synthase," *J. Chem. Soc. Commun.* (16): 1128-1130, 1988.

Baldwin et al., "A γ-Lactam Analogue Of Penems Possessing Antibacterial Activity," *Tetrahedron Letters* 27(30): 3461-3464, 1986.

Baldwin et al., "A γ-Lactam Analogue Of The Penems Possessing Antibacterial Activity," *Tetrahedron* 45(14): 4537-4550, 1989.

Baldwin et al., "Synthesis Of A Bicyclic γ-Lactam Dipeptide Analogue," *Heterocycles* 34(5): 903-906, 1992.

Baldwin et al., "Synthesis Of A Novel Bicyclic γ-Lactam Analogue Of The 1-Oxapenams," *Tetrahedron* 30(30) : 4019-4020, 1989.

Baldwin et al., "Synthesis of Potential β-Turn Bicyclic Dipeptide Mimetics," *J. Chem. Soc., Chem. Commun.* (11): 935-936, 1993.

Bauer et al., "Mehrfach ungesättigte Radikalkationen: Regio- und Stereochemie der oxidativen Dimerisierung von Heptafulvenen," *Chem. Ber.* 117: 809-826, 1984.

Baydar et al., "Acyl Analogues of the Ene Reaction," *J. Chem. Soc. Comm.* pp. 650-652, 1976.

Belshaw et al., "Synthesis, Structure and Mechanism in Immunophilin Research," *Synlett*: 381-392, 1994.

Bernabeu et al., "(2E)-4-Methoxy-2,4-pentadienamides as New Dienes in the Diels-Alder Reaction," *Tetrahedron Letters* 37(20): 3595-3598, 1996.

Bird et al., "Activation of Nuclear Transcription Factor NF-κB by Interleukin-1 Is Accompanied by Casein Kinase II-mediated Phosphorylation of the p65 Subunit," *The Journal of Biological Chemistry* 272(51): 32606-32612, 1997.

Boyd et al., "γ-Lactam Analogues Of Carbapenems," *Tetrahedron Letters* 27(30): 3457-3460, 1986.

Boyd et al., "γ-Lactam Analogues Of The Penems," *Tetrahedron Letters* 27(30): 3453-3456, 1986.

Boyd et al., "The Chemistry of N-Substituted 3-Amino-1H-2-benzopyran-1-ones and 5-Amino-2,3-dihydrofuran-2-ones. Ene-type Reactions involving Transfer of Acyl Groups. X-Ray Crystal Structure of cis-3,4-Dihydro-4-morpholinocarbonyl-3-p-nitrophenyl-1H-2-benzopyran-1-one," *J. Chem Soc. Perkin Trans. 1*: pp. 1351-1360, 1978.

Butt and Karathanasis, "Transcription Factors as Drug Targets: Opportunities for Therapeutic Selectivity," *Gene Expression*4: 319-336, 1995.

Claridge et al., "Synthesis And Analysis Of Leu-Enkephalin Analogues Containing Reverse Turn Peptidomimetics," *Bioorganic & Medicinal Chemistry Letters* 6(4): 485-490, 1996.

Colombo et al., "Conformationally Constrained Dipeptides: Synthesis of 7,5- and 6,5- Fused Bicyclic Lactams by Stereoselective Radical Cyclizations," *Tetrahedron Letters* 36(4): 625-628, 1995.

Colombo et al., "Synthesis of 7,5-Fused Bicyclic Lactams by Stereoselective Radical Cyclization," *Tetrahedron Letters* 35(23): 4031-4034, 1994.

Comille et al., "Anodic Amide Oxidations: Conformationally Restricted Peptide Building Blocks From The Direct Oxidation of Dipeptides," *Tetrahedron Letters* 35(38): 6989-6992, 1994.

Comille et al., "Electrochemical Cyclization of Dipeptides toward Novel Bicyclic, Reverse-Turn Peptidomimetics. 1. Synthesis and Conformational Analysis of 7,5-Bicyclic Systems," *J. Am. Chem. Soc.117*: 909-917, 1995.

Cowley and Stoodley, "Regio- and Stereo-selective Intermolecular Interceptions of a Conjugated N-Acylhydrazonium Ion," *Tetrahedron Letters* 35(42): 7853-7856, 1994.

Du Vigneaud and Carpenter, "The γ-Lactam of Benzylhomopenicilloic Acid and Related Compounds," in *The Chemistry of Penicillin*, Clarke et al. (eds.), Princeton University Press, Princeton, New Jersey, USA, 1949, pp. 1004-1017.

Etzkorn et al., "Cyclic Hexapeptides and Chimeric Peptides as Mimics of Tendamistat," *J. Am. Chem. Soc.* 116: 10412-10425, 1994.

Fobian et al., "New Routes To Conformationally Restricted Peptide Building Blocks: A Convenient Preparation Of Bicyclic Piperazinone Derivatives," *Bioorganic & Medicinal Chemistry Letters* 6(3): 315-318, 1996.

Gilbert and Thomas, "Nuclear Magnetic Resonance Studies and Conformations of Bicyclic Inhibitors of Angiotensin-converting Enzyme. Part 1. Octahydropyridazo[1,2-a]-pyridizanediones as Models for Alanylproline and Captopril," *J. Chem, Soc. Perkin Trans. II*(7): 1077-1082, 1985.

Goldschmidt et al., "Activation Of Electron Deficient Cycloheptatrienes By Tricarbonyliron Complexation," *Tetrahedron Letters* 31(46): 6711-6712, 1990.

Grangier et al., "Reactivity of Nucleophilic Uracil Derivatives," *J. Heterocyclic Chem.* 31: 1707-1714, 1994.

Hanessian et al., "Design And Synthesis Of A Prototype Model Antagonist Of Tachykinin NK-2 Receptor,"

*Bioorganic & Medicinal Chemistry Letters* 4(11): 1397-1400, 1994.

Hashiguchi et al., "Synthesis of γ-Lactam Analogues of Carbapanems with Substituted-thio Groups at the C-3 Position," *J. Chem. Soc. Perkin Trans. I*(8): 2345-2532, 1988.

Hassall et al., "The Design and Synthesis of New Triazolo, Pyrazolo-, and Pyridazo-pyridazine Derivatives as Inhibitors of Angiotensin Converting Enzyme," *J. Chem. Soc. Perkin Trans. I*: 155-164, 1984.

Jungeheim and Sigmund, "1,3-Dipolar Cycloaddition Reactions of Pyrazolidinium Ylides with Acetylenes. Synthesis of A New Class of Antibacterial Agents," *J. Org. Chem. 52*: 4007-4013, 1987.

Jungheim et al., "1,3-Dipolar Cycloaddition Reactions Of Pyrazolidinium Ylides With Vinyl Sulfones. A Regioselective Synthesis Of Bicyclic Pyrazolidinone Antibacterial Agents," *Tetrahedron* 44(11): 3119-3126, 1988.

Jungheim et al., "Bicyclic Pyrazolidinones, A New Class Of Antibacterial Agent Based On The β-Lactam Model," *Tetrahedron Letters* (3): 285-288, 1987.

Jungheim et al., "Bicyclic Pyrazolidinones, Steric And Electronic Effects On Antibacterial Activity," *Tetrahedron Letters* 2828(3): 289-292, 1987.

Li et al., "Conformationally Restricted Peptide Mimetics: The Incorporation of 6,5-Bicyclic Lactam Ring Skeletons into Peptides," *J. Org. Chem. 60*: 8155-8170, 1995.

Lombart and Lubell, "A Claisen condensation approach to prepare azabicycloalkane amino acid β-turn mimetics," *Peptides 1994* Proceedings of the 23rd European Peptide Symposium, H.L.S. Maia (ed.), 1995, pp. 696-697.

Lombart and Lubell, "Synthesis of Enantiopure A,ω-Diamino Dicarboxylates and Azabicycloalkane Amino Acids by Claisen Condensation of A-[N-(Phenylfluorenyl)amino] Dicarboxylates," *The Journal of Organic Chemistry* 59(21): 6147-6149, 1994.

Marchand-Brynaert et al., "New γ-Lactam Homologs Of Penems," *Bioorganic & Medicinal Chemistry Letters* 3(11): 2303-2308, 1993.

Mathews and Tulinsky, "Active-Site Mimetic of Thrombin," *Acta Crystallographica Section D. Biological Crystallography D51*(4): 550-559, Jul. 1, 1995.

Mayer et al., "A unique geometry of the active site of angiotensin-converting enzyme consistent with structure-activity studies," *Journal of Computer-Aided Molecular Design 1*: 3-16, 1987.

Moynagh et al., "Interleukin-1 activates transcription factor Nf κB in glial cells," *Biochem. J. 294*: 343-347, 1993.

Mueller and Revesz, "Synthesis of 6,5-Fused Bicyclic Lactams as Potential Dipeptide β-Turn Mimetics," *Tetrahedron Letters* 35(24): 4091-4092, 1994.

Nagai and Kato, "Synthesis of Phenyl-substituted BTD (bicyclic-turned dipeptide) and its incorporation into bioactive peptides," *Peptides* Proceedings of the 11th American Peptide Symposium, J.E. Rivier and G.R. Marshall (eds.), 1990, pp. 653-654.

Nagai and Sato, "Synthesis Of A Bicyclic Dipeptide With The Shape Of β-Turn Central Part," *Tetrahedron Letters* 26(5): 647-650, 1985.

Nagai et al., "Bicyclic Turned Dipeptide (BTD) as a β-Turn Mimetic; its Design, Synthesis and Incorporation into Bioactive Peptides," *Tetrahedron* 49(17): 3577-3592, 1993.

Roberts et al., "Asymmetric Synthesis of Two-Residue Modules Designed for Mimicry of Beta Strands," *Tetrahedron Letters* 36(5): 691-694, 1995.

Robl et al., "Dual Metalloprotease Inhibitors. 6. Incorporation of Bicyclic and Substituted Monocyclic Azepinones as Dipeptide Surrogates in Angiotensin-Converting Enzyme/Neutral Endopeptidase Inhibitors," *J. Med. Chem. 39*: 494-502, 1996.

Robl et al., "Dual Metalloprotease Inhibitors. III. Utilization Of Bicyclic And Monocyclic Diazepinone Based Mercaptoacetyls," *Bioorganic & Medicinal Chemistry Letters* 4(16): 2055-2060, 1994.

Robl, "Peptidomimetic Synthesis: Utilization of N-Acyliminium Ion Cyclization Chemistry in the Generation of 7,6- and 7,5-Fused Bicyclic Lactams," *Tetrahedron Letters* 35(3): 393-396, 1994.

Rubartelli and Sitia, "Interleukin Iβ and thioredoxin are secreted through a novel pathway of secretion," *Biochem. Soc. Trans. 19*: 255-259, 1991.

Seguchi and Tanaka, "Ready Alcoholysis of the Cycloadducts (Urazole) of 4-Phenyl-1,2,4-triazole-3,5-dione by Solvent-assisted Backbone Participation," *J. Chem. Soc. Perkin Trans. 1*: pp. 2883-2884, 1991.

Sen and Packer, "Antioxidant and redox regulation of gene trancription," *FASEB J. 10*: 709-720, 1996.

Slomcyznska et al., "Electrochemical Cyclization of Dipeptides to Form Novel Bicyclic, Reverse-Turn Peptidomimetics. 2. Synthesis and Conformational Analysis of 6,5-Bicyclic Systems," *J. Org. Chem. 61*(4): 1198-1204, 1996.

Slusarchyk et al., "Dual Metalloprotease Inhibitors. V. Utilization Of Bicyclilc Azepinonethiazolidines And Azepinonetetrahydrothiazines In Constrained Peptidomimetics Of Mercaptoacyl Dipeptides," *Bioorganic & Medicinal Chemistry Letters* 5(7): 753-758, 1995.

Songyang et al., "Use of an oriented peptide library to determine the optimal substrates of protein kinases," *Current Biology* 4(11): 973-982, 1994.

Subasinghe et al., "Bicyclic Thiazolidine Lactam Peptidomimetics of the Dopamine Receptor Modulating Peptide Pro-Leu-Gly-NH$_2$," *J. Med. Chem. 36*: 2356-2361, 1993.

Ternansky and Draheim, "[3.3.0] Pyrazolodinones: An Efficient Synthesis Of A New Class Of Synthetic Antibacterial Agents," *Tetrahedron Letters* 31(20): 2805-2808, 1990.

Ternansky and Draheim, "[4.3.0] Pyrazolidinones As Potential Antibacterial Agents," *Tetrahedron Letters* 29(50): 6569-6572, 1988.

Ternansky and Draheim, "Structure-Activity Relationship within a Series of Pyrazolidinone Antibacterial Agents. 1. Effect of Nuclear Modification on *In Vitro* Activity," *J. Med. Chem. 36*(22): 3219-3223, 1993.

Ternansky and Draheim, "The Chemistry of Substituted Pyrazolidinones; Applications to the Synthesis of Bicyclic Derivatives," *Tetrahedron* 48(5): 777-796, 1992.

Ternansky and Draheim, "The Synthesis and Biological Evaluation of Pyrazolidinone Antibacterial Agents," in *Recent Advances in the Chemistry of β-Lactam Antibiotics*, Bentley and Southgate (eds.), Royal Society Of Chemistry, Cambridge, England, 3rd-6th Jul., 1988, Special Publication No. 70, Chapter 9, "The Synthesis and Biological Evaluation of Pyrazolidinone Antibacterial Agents," pp. 139-156.

Ternansky et al., "Structure-Activity Relationship within a Series of Pyrazolidinone Antibacterial Agents. 2. Effect of Side-Chain Modification on *In Vitro* Activity and Pharmacokinetic Parameters," *J. Med. Chem. 36*: 3224-3229, 1993.

Thomas and Whitcombe, "Nuclear Magnetic Resonance Studies and Conformational Analysis of Bicyclic Inhibitors of Angiotensin-converting Enzyme. Part 2. The Octahydro-6H-pyridazo[1,2-a]diazepines," *J. Chem. Soc. Perkin Trans. II*(5): 747-755, 1986.

Wyvratt and Patchett, "Recent Developments in the Design of Angiotensin-Converting Enzyme Inhibitors," *Medicinal Research Reviews* 5(4): 483-531, 1985.

Wyvratt et al., "Bicyclic Inhibitors Of Angiotensin-Converting Enzyme," in *Peptides Structure and Function*, Proceedings of the Eighth American Peptide Symposium, Hruby and Rich (eds.), Pierce Chemical Company, Rockford, Illinois, 1983, pp. 551-554.

Kahn, M. et al., "β-Sheet Mimetics and Use Thereof as Inhibitors of Biologically Active Peptides or Proteins," U.S. Appl. No. 09/561,107, filed Apr. 28, 2000.

Qabar, M. et al., "β-Sheet Mimetics and Methods Relating to the Use Thereof," U.S. Appl. No. 09/960,864, filed Sep. 21, 2001.

Benvegnu et al., "Diels-Alder Reactions on Linear Polyenes, Selectively Protected as Their Tricarbonyl-Iron Complexes", Tetrahedron Letters, 1990, 31(22):3145-3148.

Fersht, "Enzyme Structure and Mechanism", MRC Laboratory of Molecular Biology, WH Freeman & Co., 1977, pp. 18-28 and 302-324.

Krishnan et al., "Structure of thrombin complexed with selective non-electrophillic inhibitors having cyclohexyl moieties at P1", Acta Crystallographica, 2000, D56:294-303.

Mathew et al., "Asymmetric synthesis and conformational analysis of the two enantiomers of the saturated analog of the potent thrombin inhibitorMOL-376", Tetrahedron Letters, 2002, volume date 2003, 44(3):583-586.

Oh et al., Tryptase Inhibition Blocks Airway Inflammation in a Mouse Asthma Model, The Journal of Immunology, 2002, 168(4):1992-2000.

Storer et al., "Recent insights into cysteine protease specificity: Lessons for drug design", Perspectives in Drug Discovery and Design, 1996, 6:33-46.

Thompson et al., Section VI. Topics In Drug Design and Discovery, Chapter 24. Pharmacokinetics and Design of Aspartyl Protease Inhibitors, Annual Reports in Medicinal Chemistry, 2001, 36:247-256.

* cited by examiner

β-SHEET MIMETICS AND COMPOSITION AND METHODS RELATING THERETO

CROSS-REFERENCE TO RELATED APPLICATION

This application claims the benefit of U.S. Provisional Patent Application No. 60/357,261, filed Feb. 14, 2002, where this provisional application is incorporated herein by reference in its entirety.

BACKGROUND OF THE INVENTION

1. Field of the Invention

The present invention relates generally to β-sheet mimetics, including inhibitors of tryptase in treating inflammation and several other disorders as well as to a chemical library of β-sheet mimetics.

2. Description of the Related Art

The β-sheet conformation (also referred to as a β-strand conformation) is a secondary structure present in many polypeptides. The β-sheet conformation is nearly fully extended, with axial distances between adjacent amino acids of approximately 3.5 Å. The β-sheet is stabilized by hydrogen bonds between NH and CO groups in different polypeptides sheets. Additionally, the dipoles of the peptide bonds alternate along the sheets, which imparts intrinsic stability to the β-sheet. The adjacent sheets in the β-sheet can run in the same direction (i.e., a parallel β-sheet) or in opposite directions (i.e., an antiparallel β-sheet). Although the two forms differ slightly in dihedral angles, both are sterically favorable. The extended conformation of the β-sheet conformation results in the amino acid side chains protruding on alternating faces of the β-sheet.

The importance of β-sheets in peptides and proteins is well established (e.g., Richardson, *Nature* 268:495–499, 1977; Halverson et al., *J. Am. Chem Soc.* 113:6701–6704, 1991; Zhang, *J. Biol. Chem.* 266:15591–15596, 1991; Madden et al., *Nature* 353:321–325, 1991). The β-sheet is important in a number of biological protein-protein recognition events, including interactions between proteases and their substrates.

Inhibitors that mimic the β-sheet structure of biologically active proteins or peptides would have utility in the treatment of a wide variety of conditions. For example, trypsin-like serine proteases form a large and highly selective family of enzymes involved in hemostasis/coagulation (Davie, E. W. and K. Fujikawa, "Basic mechanisms in blood coagulation," *Ann. Rev.* 799–829, 1975) and complement activation (Muller-Eberhard, H. J., "Complement," *Ann. Rev. Biochem.* 44:697–724, 1975). Sequencing of these proteases has shown the presence of a homologous trypsin-like core with amino acid insertions that modify specificity and which are generally responsible for interactions with other macromolecular components (Magnusson et al., "Proteolysis and Physiological Regulation," *Miami Winter Symposia* 11:203–239, 1976).

Tryptase, a trypsin-like serine protease found exclusively in mast cells, has attracted much interest due to its potential role as a mediator of inflammation. For example, in the lung, tryptase is released along with other mediators of inflammation in response to binding of an inhaled antigen to cell-surface IgE receptors (Ishizaka and Ishizaka, *Prog. Allergy* 34:188–235, 1984). Tryptase has also been shown to cleave vasoactive intestinal peptide in vitro (Caughey et al., *J. Pharmacol. Exp. Ther.* 244:133–137, 1988; Tam and Caughey, *Am. J. Respir. Cell Mol. Biol.* 3:27–32, 1990). These results suggest that tryptase may increase bronchoconstriction via proteolysis of bronchodilating peptides in asthma patients. Consistent with this hypothesis is the recent finding that synthetic tryptase inhibitors blocked airway responses in allergic sheep (Clark et al., *Am. J. Respir. Crit. Care Med.* 152:2076–2083, 1995).

Tryptase activates extracellular matrix-degrading proteins prostromelysin (pro-MMP-3) and procollagenase (pro-MMP-1) via MMP-3, suggesting a role for the enzyme in tissue remodeling and inflammation (Gruber et al., *J. Clin. Invest.* 84:8154–8158, 1989) and, therefore, possibly in rheumatoid arthritis. Additionally, prostromelysin, when activated, has been shown to degrade the extracellular matrix around atherosclerotic plaques. Since abnormally high levels of tryptase-containing mast cells have been found in coronary atheromas, tryptase may play a role in atheromatous rupture (release of the thrombus), the final event of coronary atherosclerosis (Kaartinen et al., *Circulation* 90:1669–1678, 1994).

Other activities of tryptase include the following. Tryptase cleaves fibrinogen but is not inactivated in the presence of endogenous proteinase inhibitors (Schwartz et al., *J. Immunol.* 135:2762–2767, 1985; Ren et al., *J. Immunol.* 159:3540–3548, 1997), and may function as a local anticoagulant. It has been demonstrated to be a potent mitogen for fibroblasts and may be involved in pulmonary fibrosis and interstitial lung disease (Ruoss et al., *J. Clin. Invest.* 88:493–499, 1991). Tryptase may also be responsible for the activation of PAR-2 (proteinase activated receptor-2) on endothelial cells and keratinocytes (Molino et al., *J. Biol. Chem.* 272:4043–4049, 1997).

Inhibition of intestinal motility, especially colonic motility, is a major complication of abdominal surgery. The condition, termed post-operative ileus, delays the normal resumption of food intake after surgery and often leads to prolonged hospitalization. Mast cells are pro-inflammatory cells that are normally present in the wall of the intestine. Manipulation of intestine and intestinal inflammation are accompanied by influx and degranulation of mast cells in the wall of the intestine. Mast cell tryptase and chymase are proteases that account for 25% of the total protein of mast cells (Schwartz et al., *J. Immunol.* 138:2611–2615, 1987). They are released from mast cell upon degranulation within the wall of the colon. A method of treating or preventing post-operative ileus was discovered based on the observation that PAR-2 is expressed in colonic muscle cells, and that activation of PAR-2 inhibits colonic motility. Since the PAR-2 receptor is activated, at least in part, by tryptase, inhibition of tryptase could be an effective method of treating post-operative ileus (U.S. Pat. Nos. 5,958,407 and 5,888,529).

Given the central role of mast cells in allergic and inflammatory responses, inhibition of tryptase may result in significant therapeutic effects. Inhibitors of tryptase may be useful for preventing or treating asthma, pulmonary fibrosis and interstitial pneumonia, nephritis, hepatic fibrosis, hepatitis, hepatic cirrhosis, scleroderma, psoriasis, atopic dermatitis, chronic rheumatoid arthritis, influenza, Crohn's disease, ulcerative colitis, inflammatory bowel disease, nasal allergy, and atherosclerosis.

While significant advances have been made in the synthesis and identification of conformationally constrained, β-sheet mimetics (U.S. Pat. Nos. 6,245,764, 6,117,896 and 6,020,331 and published PCT WO00/11005 and WO99/41276), there is still a need in the art for small molecules that mimic the secondary structure of peptides. There is also a need in the art for libraries containing such members, particularly those small templates capable of supporting a high diversity of substituents. In addition, there is a need in the art for techniques for synthesizing these libraries and screening the library members against biological targets to identify bioactive library members. Further, there is a need in the art for small, orally available inhibitors of tryptase, for use in treating inflammatory diseases, central nervous system disorders, as well as several other disorders. In particular, there is a need for inhibitors of tryptase for use in the treatment or prevention of various mammalian disease states, for example asthma, cough, chronic obstructive pulmonary disease (COPD), bronchospasm, emesis, neurodegenerative disease, ocular disease, inflammatory diseases such as arthritis, central nervous system conditions such as anxiety, migraine and epilepsy, nociception, psychosis, and various gastrointestinal disorders such as Crohn's disease.

The present invention fulfills these needs and provides further related advantages.

SUMMARY OF THE INVENTION

In brief, the present invention is directed to conformationally constrained compounds, which mimic the secondary structure of β-strand regions of biologically active peptides and proteins. It is also directed towards use of these compounds for the prevention and treatment of inflammatory and several other disorders. The compounds of the present invention have the following general structure (I):

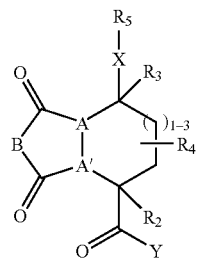

(I)

and pharmaceutically acceptable salts and stereoisomers thereof, wherein A, A', B, X, Y, $R_2$, $R_3$, $R_4$ and $R_5$ are as defined below.

The present invention is also directed to libraries containing compounds of structure (I), as well as methods for synthesizing such libraries and methods for screening the same to identify biologically active compounds. In addition, compositions containing a compound of this invention in combination with a pharmaceutically acceptable carrier are disclosed. Methods of use for treating cell-adhesion-mediated disease with the compounds of this invention and compositions comprising them are also disclosed. Further, methods of use for treatment and prevention of inflammatory disorders, as well as several other disorders with the compounds of this invention and compositions comprising them are also disclosed.

These and other aspects of this invention will be apparent upon reference to the following detailed description. To this end, various references are set forth herein which describe in more detail certain procedures, compounds and/or compositions, and are incorporated by reference in their entirety.

DETAILED DESCRIPTION OF THE INVENTION

The present invention is directed to β-strand mimetics and chemical libraries containing β-strand mimetics. The β-strand mimetics of the present invention are useful as bioactive agents, including (but not limited to) use as diagnostic, prophylactic and/or therapeutic agents, especially as anti-inflammatory agents, for central nervous system disorders, and as well as several other disorders. The β-strand mimetic libraries of this invention are useful in the identification of such bioactive agents. In the practice of the present invention, the libraries may contain from tens to hundreds to thousands (or greater) of individual β-strand mimetics (also referred to herein as "members").

In one aspect of the present invention, a β-strand mimetic is disclosed having the following structure (I):

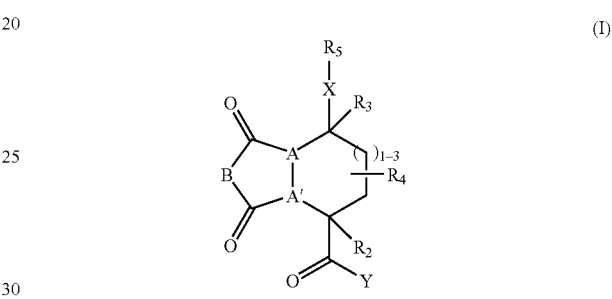

(I)

or a pharmaceutically acceptable salt or stereoisomer thereof, wherein

A and A' are the same or different and independently N or CH;

B is —C($R_1$)(NHZ)-, —N(Z)- or —C($R_1$)(Z)-;

X is a substituted or unsubstituted divalent heterocycle;

Y and Z represent the remainder of the molecule;

$R_1$, $R_2$, $R_3$, $R_4$ and $R_5$ are the same or different and independently an amino acid side chain moiety or an amino acid side chain derivative; and any two adjacent CH groups (i.e., CH—CH) or adjacent NH and CH groups (i.e., NH—CH) of the fused bicyclo compound optionally form a double bond (i.e., C═C or N═C, respectively).

As used herein, an "amino acid side chain moiety" refers to any amino acid side chain moiety present in naturally occurring alpha-amino acids and other "non-protein" amino acids commonly utilized by those in the peptide chemistry arts when preparing synthetic analogues of naturally occurring peptides, including D and L forms. The "non-protein" amino acids refer to unnatural alpha-amino acids, beta-amino acids and gamma-amino acids commonly utilized by those in the peptide chemistry arts when preparing synthetic analogues of naturally occurring peptides, including D and L forms. An "amino acid side chain moiety" as used herein, including (but not limited to) the naturally occurring amino acid side chain moieties are identified in Table I below. Other naturally occurring amino acid side chain moieties of this invention include (but are not limited to) the side chain moieties of 3,5-dibromotyrosine, 3,5-diiodotyrosine, hydroxylysine, γ-carboxyglutamate, phosphotyrosine, phosphothreonine and phosphoserine. In addition, glycosylated amino acid side chains may also be used in the practice of this invention, including (but not limited to) glycosylated threonine, serine, glutamine and asparagine.

TABLE 1

AMINO ACID SIDE CHAIN MOIETIES

| Amino Acid Side Chain Moiety | Amino Acid |
|---|---|
| —H | Glycine |
| —CH₃ | Alanine |
| —CH(CH₃)₂ | Valine |
| —CH₂CH(CH₃)₂ | Leucine |
| —CH(CH₃)CH₂CH₃ | Isoleucine |
| —(CH₂)₄NH₂ | Lysine |
| —(CH₂)₃NHC(NH₂)NH₂ | Arginine |
| 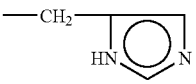 | Histidine |
| —CH₂COOH | Aspartic acid |
| —CH₂CH₂COOH | Glutamic acid |
| —CH₂CONH₂ | Asparagine |
| —CH₂CH₂CONH₂ | Glutamine |
| 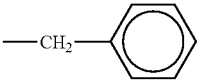 | Phenylalanine |
| 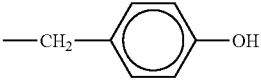 | Tyrosine |
| 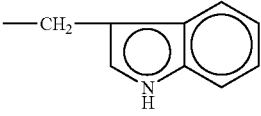 | Tryptophan |
| —CH₂SH | Cysteine |
| —CH₂CH₂SCH₃ | Methionine |
| —CH₂OH | Serine |
| —CH(OH)CH₃ | Threonine |
|  | Proline |
| 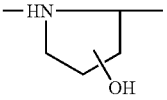 | Hydroxyproline |

In addition, as used herein, an "amino acid side chain derivative" represents modifications and/or variations to amino acid side chain moieties, including hydroxyl (—OH). For example, the amino acid side chain moieties of alanine, valine, leucine, isoleucine and phenylalanine may generally be classified as alkyl, aryl, or arylalkyl moieties, optionally substituted with one or more substituents as defined below. Similarly, the amino acid side chain moieties of histidine, tryptophan, proline and hydroxyproline may generally be classified as heterocyclic or heterocyclicalkyl moieties, optionally substituted with one or more substituents as defined below. Accordingly, representative amino acid side chain derivatives include substituted or unsubstituted alkyl, aryl, arylalkyl, heterocycle, heterocyclealkyl, heteroaryl and heteroarylalkyl moieties.

Amino acid side chain derivatives also include, but are not limited to, the amino acid side chains of hydroxylysine, homoserine, homotyrosine, homophenylalanine, citrulline, kynurenine, 4-aminophenylalanine, 3-(2-naphthyl)-alanine, 3-(1-naphthyl)alanine, methionine sulfone, t-butyl-alanine, t-butylglycine, 4-hydroxyphenylglycine, aminoalanine, phenylglycine, vinylalanine, prop argyl-glycine, 1,2,4-triazolo-3-alanine, 4,4,4-trifluoro-threonine, thyronine, 6-hydroxytryptophan, 5-hydro-xytryptophan, 3-hydroxykynurenine, 3-aminotyrosine, trifuoromethyl-alanine, 2-thienylalanine, (2-(4-pyridyl)ethyl)cysteine, 3,4-dimethoxy-phenylalanine, 3,5-bistrifluoro-phenylalanine,3-(2-thiazolyl)-alanine, ibotenic acid, 1-amino-1cyclopentane-carboxylic acid, 1-amino-1cyclohexanecarboxylic acid, quisqualic acid, 3-trifiuoromethylphenylalanine, 4-trifiuoromethylphenylalanine, cyclohexylalanine, cyclohexylglycine, thiohistidine, 3-methoxytyrosine, elastatinal, norleucine, norvaline, alloisoleucine, homoarginine, thioproline, dehydroproline, hydroxy-proline, isonipectotic acid, homoproline, cyclohexyl-glycine, α-amino-n-butyric acid, cyclohexylalanine, aminophenylbutyric acid, phenylalanines substituted at the ortho, meta, or para position of the phenyl moiety with one or two of lower alkyl, lower alkoxy, halogen or nitro group, or substituted with a methylenedioxy group; β-2- and 3-thienylalanine, β-2- and 3-furanylalanine, β-2-, 3- and 4-pyridylalanine, β-(benzothienyl-2- and 3-yl)alanine, β-(1 and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-sulfo-tyrosine, 3-carboxy-tyrosine, 3-phosphotyrosine, 4-methane sulfonic acid ester of tyrosine, 4-methane phosphonic acid ester of tyrosine, 3,5-diiodotyrosine, 3-nitro-tyrosine, ε-alkyl lysine and δ-alkyl ornithine, and the like. Any of these "amino acid side chain derivatives" may be substituted with a methyl group at the alpha, beta or gamma positions, a halogen at any aromatic residue on the amino side chain, or an appropriate protective group at the O, N, or S atoms of the side chain moities. Appropriate protective groups are disclosed in "Protective Groups In Organic Synthesis," T. W. Greene and P. G. M. Wuts, J. Wiley & Sons, NY, MY, 1991.

As used herein, "alkyl" is a straight chain or branched, cyclic or noncyclic, saturated or unsaturated alkyl containing from 1 to 12 carbon atoms (also referred to herein as "$C_{1-12}$alkyl"). Similarly, a "lower alkyl" is as defined above, but contains from 1 to 4 carbon atoms (also referred to herein as a "$C_{1-4}$alkyl"). Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like. Unsaturated alkyls contain at least one double or triple bond between adjacent carbon atoms (referred to as an "alkenyl" or "alkynyl," respectively). Representative straight chain and branched alkenyls include ethylenyl, propylenyl, 1-butenyl, 2-butenyl, isobutenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. Representative unsaturated cyclic alkyls include cyclopentenyl and cyclohexenyl, and the like. Alkyls include "alkoxy" as defined below.

"Alkoxy" is an alkyl having at least one alkyl hydrogen atom replaced with an oxygen atom, such as methoxy, ethoxy, n-propoxy, n-butoxy, n-pentoxy, isopropoxy, sec-butoxy and the like. "Lower alkoxy" has same meaning, but utilizing lower alkyl in place of alkyl.

"Aminoalkyl" is a straight chain or branched, cyclic or noncyclic, saturated or unsaturated alkyl containing from 1 to 12 carbon atoms with at least one alkyl hydrogen atom or carbon atom replaced with —NH$_2$ or —NH—, respectively (also referred to herein as "C$_{1-12}$aminoalkyl").

"Aryl" is an aromatic carbocyclic moiety contain from 6 to 12 carbon atoms (also referred to herein as a "C$_{6-12}$aryl"), such as phenyl and naphthyl. Aryls include aryloxy, as defined below.

"Aryloxy" is an aryl having at least one aryl hydrogen atom replaced with an oxygen atom, such as phenoxy and the like.

"Arylalkyl" is an alkyl having at least one alkyl hydrogen atom replaced with an aryl moiety, such as benzyl, —(CH$_2$)$_2$phenyl, —(CH$_2$)$_3$phenyl, —CH(phenyl)$_2$, and the like. Arylalkyls include arylalkoxy as defined below.

"Arylalkoxy" is an arylalkyl having at least one alkyl hydrogen replaced with an oxygen atom, such as benzoxy and the like. "Alkylaryloxy" is an arylalkyl having at least one aryl hydrogen replaced with and oxygen atom, such as hydroxy benzyl and the like.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Thus, in addition to the heteroaryls listed below, heterocycles also include morpholinyl, pyrrolidinonyl, pyrrolidinyl, piperidinyl, hydantoinyl, valerolactamyl, oxiranyl, oxetanyl, aziridinyl, azetidinyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl and the like.

In the context of X of structure (I) above, "divalent heterocycle" means a heterocycle moiety covalently bonded to both an R$_5$ moiety and the carbon atom of the fused bicyclic ring system of structure (I).

"Heterocyclealkyl" means an alkyl having at least one alkyl hydrogen atom replaced with a heterocycle moiety, such as —CH$_2$(heterocycle), —(CH$_2$)$_2$(heterocycle) and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl and the like.

"Heteroarylalkyl" means an alkyl having at least one alkyl hydrogen atom replaced with a heteroaryl moiety, such as —CH$_2$pyridinyl, —CH$_2$pyrimidinyl, and the like.

The term "substituted" as used herein means any of the above groups—that is, alkyl, aryl, arylalkyl, heterocycle, divalent heterocycle, heterocyclealkyl, heteroaryl or heteroarylalkyl—wherein at least one hydrogen atom is replaced with a substituent. In the case of an oxo substituent ("=O"), two hydrogen atoms are replaced. A "substituent" in this regard is halogen (such as F, Cl, Br and I), oxo, hydroxy, haloalkyl (such as trifluoromethyl), —R, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —NRSO$_2$R, —Si(R)$_3$, or —OP(OR)$_3$, wherein each occurrence of R is the same or different and independently hydrogen, alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocycle or a substituted heterocycle.

A "peptide" means at least two naturally or unnaturally occurring alpha-amino acids joined via a peptide bond. Depending upon the number of amino acids joined via peptide bonds, the resulting peptide may also be referred to as a "polypeptide" or "protein." Similarly, a "peptide derivative" means a peptide which has been covalently modified and/or which contains amino acids other than alpha-amino acids. Representative peptide derivatives include peptides which are N-alkylated, N-acylated or N-sulfonylated at the amino termini, with, for example, methyl, benzyl, acetyl, benzoyl, methanesulfonyl, phenylsulfonyl, allyloxycarbonyl, t-butyloxycarbonyl, benzyloxycarbonyl, or fluorenyloxycarbonyl moieties; peptides in which the carboxy termini are esterified (methyl, ethyl, benzyl) or reduced to a hydroxy or aldehyde; peptides which are N-alkylated at peptide bonds with, for example, methyl or 2-hydroxy-4-methoxybenzyl; and peptides which incorporate beta- or gamma-amino acids such as beta-alanine or gamma-aminobutyric acid.

A "linker" is any covalent bridging moiety that facilitates linkage of a compound of structure (I), through the respective R$_1$, R$_2$, R$_3$ and/or R$_4$ moiety, to another moiety, agent, compound, solid support, molecule, amino acid, peptide or protein. For example, the compounds of this invention may be linked to one or more known compounds, such as biotin, for use in diagnostic or screening assays. Furthermore, one (or more) of R$_1$, R$_2$, R$_3$ or R$_4$ may be a linker joining the compound of structure (I) to a solid support (such as a support used in solid phase peptide synthesis). Examples of such linkers include p-alkoxybenzyl alcohol, phenylacetamidomethyl, and 2-chlorotrityl chloride.

A "solid support" means any composition of matter to which another compound is attached directly or attached through a linker, and that is insoluble in at least one solvent in which the attached compound is soluble. Alternatively, a "solid support" may be a composition of matter with similar solubility characteristics to the attached compound, but which may be readily precipitated from solution and filtered off as a solid. Representative examples include polystyrene, polyethylene glycol, polystyrene grafted with polyethylene glycol, polyacrylamide, polyamide-polyethylene glycol copolymer, controlled-pore glass, and silica.

The phrase "remainder of the molecule" means any moiety, agent, compound, solid support, molecule, linker, amino acid, peptide or protein covalently attached to the β-strand mimetic at Y and Z positions, including amino acid side chain moieties, amino acid side chain derivatives and peptide derivatives, as defined above. Accordingly, in an alternative depiction of structure (I), the corresponding Y and Z moieties may be left undefined, as represented by the following structures (I'), (I") and (I''')

(I')

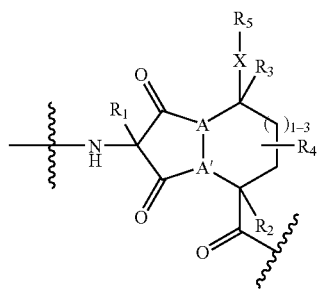

(I'')

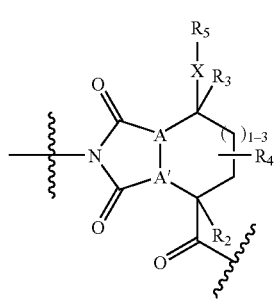

(I''')

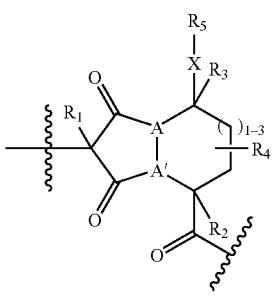

wherein "∼∼∼" represents the remainder of the molecule and A, A', R₁, R₂, R₃, R₄ and R₅ are as defined above.

In a further embodiment of structure (I), the compounds of this invention have the following structure (II):

(II)

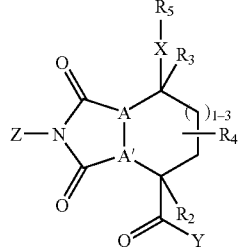

or pharmaceutically acceptable salts and stereoisomers thereof, wherein A, A', X, Y, Z, R₂, R₃, R₄ and R₅ are as defined above.

In a further embodiment of structure (II), the compounds of this invention have the following structure (III):

(III)

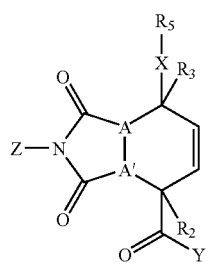

or pharmaceutically acceptable salts and stereoisomers thereof, wherein A, A', X, Y, Z, R₂, R₃ and R₅ are as defined above.

In still a further embodiment of structure (II), R₂ and R₃ are hydrogen, and the compounds of this invention have the following structure (IV):

(IV)

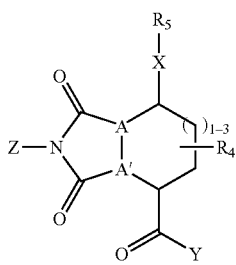

or pharmaceutically acceptable salts and stereoisomers thereof, wherein A, A', X, Y, Z, R₄ and R₅ are as defined above.

In still a further embodiment of structure (IV), A and A' are both N, and the compounds of this invention have the following structure (V):

(V)

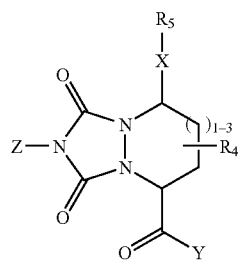

or pharmaceutically acceptable salts and stereoisomers thereof, wherein X, Y, Z, R₄ and R₅ are as defined above.

In still a further embodiment of structure (V), R₄ is hydrogen, and the compounds of this invention have the following structure (VI):

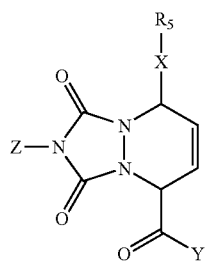

(VI)

or pharmaceutically acceptable salts and stereoisomers thereof, wherein X, Y, Z and $R_5$ are as defined above.

In still a further embodiment of structure (VI), X is a nitrogen containing divalent heterocycle, and the compounds of this invention have the following structure (VII):

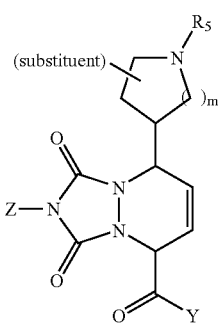

(VII)

or pharmaceutically acceptable salts and stereoisomers thereof, wherein Y, Z, $R_5$ and "substituent" are as defined above and m is 1, 2, 3 or 4, and wherein $R_5$, taken together with the substitutent, may optionally form a substituted or unsubstituted heterocycle.

In still a further embodiment of structure (VII), the compounds of this invention have the following structure (VIII):

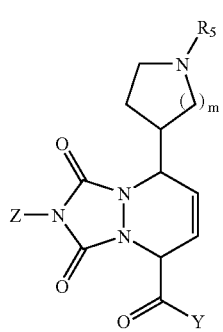

(VIII)

or pharmaceutically acceptable salts and stereoisomers thereof, wherein Y, Z, m and $R_5$ are as defined above.

In still a further embodiment of structure (VIII), m is 2 and the compounds of this invention have the following structure (IX):

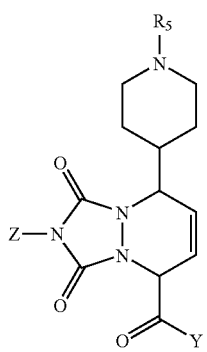

(IX)

or pharmaceutically acceptable salts and stereoisomers thereof, wherein Y, Z and $R_5$ are as defined above. In a more specific embodiment of structure (IX), Y and Z are each an amino acid side chain moiety or an amino acid side chain derivative.

In still a further embodiment of structure (IX), Y is —$NHR_6$, and the compounds of this invention have the following structure (X):

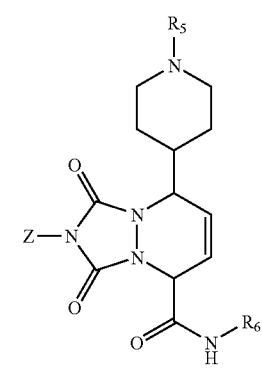

(X)

or pharmaceutically acceptable salts and stereoisomers thereof,
  wherein
  Z is
    1) alkyl,
    2) alkoxy,
    3) phenyl,
    4) benzyl,
    5) phenethyl,
    6) 1-napthylmethyl,
    7) 2-napthylmethyl,
    8) phenylbenzyl,
    9) biphenyl,
    10) aminoalkyl,
    11) aryl,
    12) arylalkyl,
    13) Het,
    14) a group selected from $R_{7d}$,
    15) —$(CH_2)_o$—$N(R_dR_{d'})$,
    16) —$(CH_2)_m$-aryl-$NHR_t$,
    17) —$(CH_2)_m$-aryl-$NR_dR_{d'}$,
    18) —$(CH_2)_o$—$CO_2R_e$,
    19) —$(CH_2)_o$—$C(=O)$—$NR_eR_{e'}$, 20) —(CH$_2$)$_o$—O—R$_f$,
21) —(CH$_2$)$_o$—SO$_2$-aryl,
22) —(CH$_2$)$_o$-Het, or
23) hydrogen,
wherein alkyl, phenyl, benzyl, phenethyl, 1-napthylmethyl, 2-napthylmethyl, phenylbenzyl, biphenyl, aminoalkyl, aryl, arylalky and Het are optionally and independently substituted with but not limited to one or more substituents independently selected from R$_s$;

R$_d$ and R$_{d'}$ are the same or different and independently selected from
1) hydrogen,
2) —C(=O)-alkyl,
3) —C(=O)-alkenyl,
4) —C(=O)-alkynyl,
5) —C(=O)-aryl,
6) —C(=O)-alylalkyl,
7) —C(=O)-Het,
8) a group selected from R$_5$,
9) —C(=O)-alkyl-NH$_2$,
10) —C(=O)(CH$_2$)$_m$-aryl-(CH$_2$)$_n$—NH$_2$,
11) —C(=O)(CH$_2$)$_m$-aryl-(CH$_2$)$_n$-Het,
12) —C(=O)(CH$_2$)$_m$-1,4 cyclohexyl-(CH$_2$)$_n$—NH$_2$,
13) —C(=O)(CH$_2$)$_m$-aryl-OH,
14) —C(=O)(CH$_2$)$_m$-aryl-SO$_2$—NH$_2$,
15) —C(=O)(CH$_2$)$_m$-aryl-(CH$_2$)$_n$—NHC(=O)-alkyl,
16) —C(=O)(CH$_2$)$_m$-Het,
17) —C(=O)(CH$_2$)$_m$—S-Het,
18) —SO$_2$-aryl,
19) —SO$_2$-aryloxy, and
20) —SO$_2$-arylalkyl,
wherein alkyl, alkenyl, alkynyl, aryl, arylalkyl, aryloxy and Het are optionally and independently substituted with but not limited to one or more substituents independently selected from R$_s$;

R$_e$ and R$_{e'}$ are the same or different and independently selected from
1) hydrogen,
2) alkyl,
3) alkenyl,
4) alkynyl,
5) aryl,
6) arylalkyl,
7) Het,
8) -alkylaryl,
9) —(CH$_2$)$_o$-aryl-(CH$_2$)$_m$—NH$_2$,
10) —(CH$_2$)$_o$—NH-aryl,
11) —(CH$_2$)$_o$-1,4 cyclohexyl-(CH$_2$)$_m$—NH$_2$,
12) —(CH$_2$)$_o$-aryloxy,
13) —(CH$_2$)$_o$-aryl-NH$_2$,

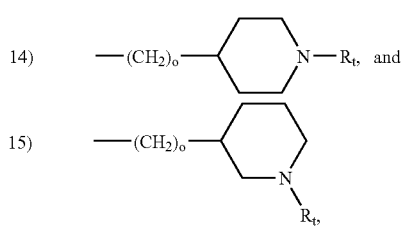

wherein alkyl, alkenyl, alkynyl, aryl, arylalkyl and Het are optionally and independently substituted with but not limited to one or more substituents independently selected from R$_s$;

R$_f$ is selected from
1) hydrogen,
2) alkyl,
3) alkenyl,
4) alkynyl,
5) aryl,
6) arylalkyl,
7) Het,
8) alkylaryl,
9) —C(=O)-alkyl,
10) —C(=O)-aryl,
11) —C(=O)-arylalkyl,
12) —C(=O)-Het,
13) —C(=O)-alkylaryl,
14) —C(=O)—NH-alkyl,
15) —C(=O)—NH-aryl,
16) —C(=O)—NH-arylalkyl,
17) —C(=O)—NH-Het, and
18) —C(=O)—NH-alkylaryl,
wherein alkyl, alkenyl, alkynyl, aryl, arylalkyl and Het are optionally and independently substituted with but not limited to one or more substituents independently selected from R$_s$;

R$_s$ is
1) halogen,
2) hydrogen,
3) lower alkyl
4) —CN,
5) —CF$_3$,
6) —C(=O)OR$_e$,
7) —C(=O)R$_e$,
8) —C(=NH)—NH$_2$,
9) —C(=NR$_d$)(NR$_d$R$_{d'}$),
10) —NR$_d$R$_{d'}$,
11) —NR$_e$C(O)R$_e$,
12) —NR$_e$C(=O)OR$_e$,
13) —NR$_e$C(=O)NR$_e$R$_{e'}$,
14) —NH—C(=NH)NH$_2$,
15) —NO$_2$,
16) —OCF$_3$,
17) —OH,
18) —OR$_e$,
19) —OC(=O)R$_e$,
20) —OC(=O)NR$_e$R$_{e'}$,
21) —SR$_e$,
22) —S(O)$_k$R$_e$,
23) —S(O)$_2$OR$_e$,
24) —S(O)$_k$NR$_e$R$_{e'}$, or
25) a group selected from R$_5$;

R$_t$ is
1) hydrogen,
2) —C(=NH)—NH$_2$, or
3) a group selected from R$_5$;

R$_5$ is
1) —C(=O)O—R$_7$,
2) —C(=O)NH—R$_7$,
3) —S(O$_2$)—R$_7$,
4) —C(=O)—R$_7$, or
5) hydrogen,
wherein
R$_7$ is R$_{7a}$, R$_{7b}$, R$_{7c}$ or R$_{7d}$;
R$_{7a}$ is alkyl or aminoalkyl optionally and independently substituted with but not limited to one or more substituents independently selected from R$_s$;
R$_{7b}$ is aryl, arylalkyl or Het optionally and independently substituted with but not limited to one or more substituents independently selected from R$_s$;

$R_{7c}$ is phenyl, benzyl or phenethyl optionally and independently substituted with but not limited to one or more substituents independently selected from $R_s$;

$R_{7d}$ is
1) $-(CH_2)_l-NR_dR_{d'}$,
2) $-(CH_2)_l-CO_2R_e$,
3) $-(CH_2)_m$-aryl-$(CH_2)_n-NR_dR_{d'}$,
4) $-CH(NR_dR_{d'})-(CH_2)-NR_dR_{d'}$,
5) $-(CH_2)_m$-1,4 cyclohexyl-$(CH_2)_n-NR_dR_{d'}$,
6) $-(CH=CH)_k-(CH_2)_p-NR_dR_{d'}$, 7) 

8) 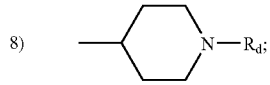

$R_6$ is
1) $-(CH_2)_l-NHR_t$,
2) $-(CH_2)_l$-Het-$NHR_t$,
3) $-(CH_2)_o$-aryl-$(CH_2)_n-R_t$,
4) $-(CH_2)_o$-aryl-$(CH_2)_m-NHR_t$,
5) $-(CH_2)_o$-cyclohexyl-$(CH_2)_m-NHR_t$,
6) $-(CH=CH)_k-(CH_2)_p-NHR_t$, 7) 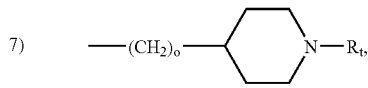

8) 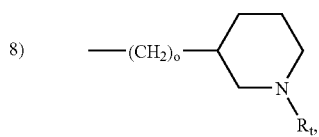

9) 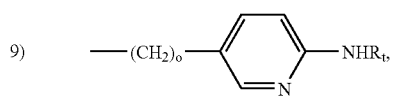

10) 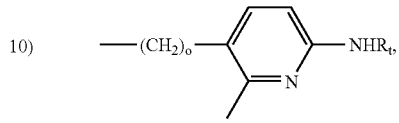

11) 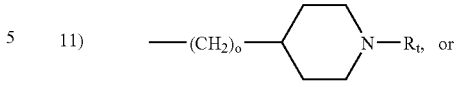

12) 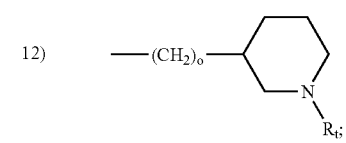

$R_d$ and $R_{d'}$ taken together with the atoms to which they are attached form a mono- or bi-cyclic heterocyclic ring of 3 to 7 members each containing 0–3 additional heteroatoms each independently selected from nitrogen, oxygen and sulfur;

$R_e$ and $R_{e'}$ taken together with the atoms to which they are attached form a mono- or bi-cyclic heterocyclic ring of 3 to 7 members each containing 0–3 additional heteroatoms each independently selected from nitrogen, oxygen and sulfur;

k is an integer from 1 to 2;
l is an integer from 1 to 10;
m is a number from 0 to 4;
n is a number from 0 to 4;
o is an integer from 1 to 4;
p is an integer from 1 to 2; and Het is heterocycle, heterocyclealkyl, heteroaryl or heteroarylalkyl.

In structure (I) above, a solid line designation for attachment of the various R groups to a carbon atom on the fused bicyclic ring indicates that these R groups may lie either above or below the plane of the page. If a β-strand mimetic of this invention is intended to mimic a β-strand of naturally occurring amino acids (i.e., "L-amino acids"), the R groups would generally lie below the plane of the page (i.e., "⫶⫶⫶R") in structure (I). However, if the β-strand mimetic of this invention is intended to mimic a β-strand containing one or more D-amino acids, then the corresponding R group or groups would lie above the plane of the page (i.e., "◼R") in structure (I).

In still a more specific embodiment of structure (I), the compound of this invention have the following conformation (XI):

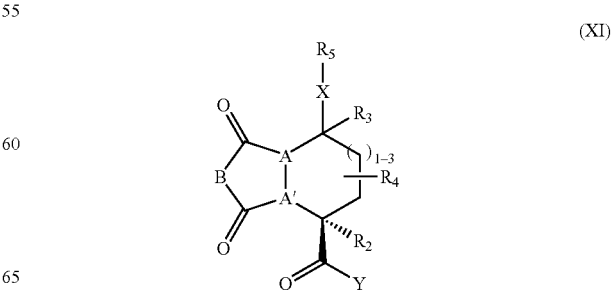

(XI)

In still a more specific embodiment of structure (I), the compound of this invention have the following conformation (XII):

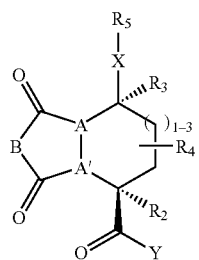

(XII)

In still a more specific embodiment of structure (I), the compound of this invention has the following conformation (XIII):

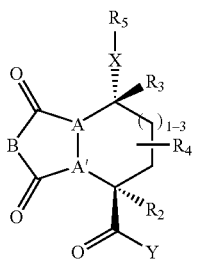

(XIII)

In still a more specific embodiment of structure (I), the compound of this invention has the following conformation (XIV):

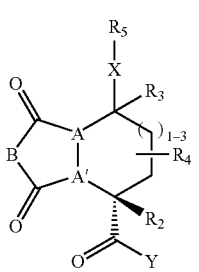

(XIV)

In still a more specific embodiment of structure (I), the compound of this invention has the following conformation (XV):

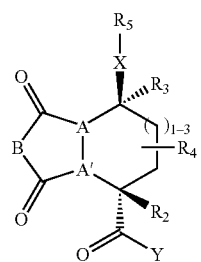

(XV)

In still a more specific embodiment of structure (I), the compound of this invention has the following conformation (XVI):

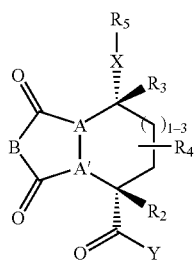

(XVI)

The compounds of the present invention may generally be prepared by sequential coupling of the individual component pieces, either stepwise in solution or by solid phase synthesis, as commonly practiced in solid phase peptide synthesis. To this end, the compounds may be synthesized on a solid support (such as polystyrene utilizing 4-hydroxymethylphenoxybutyrate as a linker) by known techniques (see, e.g., John M. Stewart and Janis D. Young, *Solid Phase Peptide Synthesis*, 1984, Pierce Chemical Comp., Rockford, Ill.; Atherton, E., Shepard, R. C. *Solid Phase Peptide Synthesis: A Practical Approach*; IRL: Oxford, 1989) or on a silyl-linked resin by alcohol attachment (Randolph et al., *J. Am. Chem. Soc.* 117.5712–14, 1995). The utility and ease of synthesis of the present invention is further exemplified by the applicability of a wide variety of commercially available resins. To this end, a core of either polystyrene or ArgoGel (polyethyleneglycol grafted polystyrene; Argonaut, San Carlos, Calif.) utilizing aminomethyl polystyrene, benzhydrylamine (BHA) methylbenzhydrylamine (MBHA) (Matsueda et al., *Peptides* 2:45, 1981), phenoxybenzylalcohol (Wang resin) (Wang *J. Am. Chem. Soc.* 95:1328, 1973), 2-clorotrityl (Barlos et al., *Tetrahedron Lett.* 30:3943, 1989, *ibid* 30:3947, 1989), and PAL (Albericio et al., *J. Org. Chem.* 55:3730 1990) resins and other resins could be used in the synthesis of the present invention.

In addition, a combination of both solution and solid phase synthesis techniques may be utilized to synthesize the compounds of this invention. For example, a solid support may be utilized to synthesize a linear peptide sequence up to the point that the compound of this invention is added to the sequence. A suitable compound that has been previously synthesized by solution synthesis techniques may then be added as the next "amino acid" to the solid phase synthesis (i.e., the compound, which has at least two reactive sites, may be utilized as the next residue to be added to the linear peptide). Upon incorporation of the compound into the sequence, additional amino acids may then be added to complete the peptide bound to the solid support. Alternatively, the linear N-terminus and C-terminus protected peptide sequences may be synthesized on a solid support, removed from the support, and then coupled to the compound in solution using known solution coupling techniques.

In another aspect of this invention, methods for constructing libraries are disclosed. Traditional combinatorial chemistry (e.g., *The Combinatorial Index* Bunin, Academic Press, New York, 1998; Gallop et al., *J. Med. Chem.* 37:1233–1251, 1994) and parallel synthesis techniques permit a vast number of compounds to be rapidly prepared by the sequential combination of reagents to a basic molecular scaffold. For example, the above-disclosed synthesis may be carried out using the directed sorting technique of Nicolaou and coworkers. (Nicolaou et al., *Angew. Chem. Int'l. Ed.* 34:2289–2291, 1995). Presently, equipment for this technique is commercially available from IRORI (La Jolla, Calif.). Alternatively, the above disclosed synthesis may be carried out by parallel synthesis using a 48- or 96-well plate format wherein each well contains a fritted outlet for draining solvents and reagents (*A Practical Guide to Combinatorial Chemistry* Czarnik and DeWitt, Eds., American Chemical Society, Washington, D.C., 1997). Robbins (Sunnyvale, Calif.), Charybdis (Carlsbad, Calif.) and Bohdan (Chicago, Ill.) presently offer suitable equipment for this technique.

In a further aspect of this invention, methods for screening libraries for bioactivity and isolating bioactive library members are disclosed. The libraries of the present invention may be screened for bioactivity by a variety of techniques and methods. Generally, the screening assay may be performed by (1) contacting a library with a biological target of interest, such as a receptor, and allowing binding to occur between the mimetics of the library and the target, and (2) detecting the binding event by an appropriate assay, such as by the calorimetric assay disclosed by Lam et al. (*Nature* 354: 82–84, 1991) or Griminski et al. (*Biotechnology* 12:1008–1011, 1994). In a preferred embodiment, the library members are in solution and the target is immobilized on a solid phase. Alternatively, the library may be immobilized on a solid phase and may be probed by contacting it with the target in solution.

In another aspect, the present invention encompasses pharmaceutical compositions prepared for storage or administration, which comprise a therapeutically effective amount of a compound of the present invention in a pharmaceutically acceptable carrier or diluent. Therapy with inhibitors of cell adhesion is indicated for the treatment and prevention of a variety of inflammatory conditions, particularly rheumatoid arthritis, inflammatory bowel disease and asthma. Those experienced in this field are readily aware of the circumstances requiring anti-inflammatory therapy.

The "therapeutically effective amount" of a compound of the present invention will depend on the route of administration, the type of warm-blooded animal being treated, and the physical characteristics of the specific animal under consideration. These factors and their relationship to determining this amount are well known to skilled practitioners in the medical arts. This amount and the method of administration can be tailored to achieve optimal efficacy, but will depend on such factors as weight, diet, concurrent medication and other factors that, as noted, those skilled in the medical arts will recognize. Typically, dosages will be between about 0.01 mg/kg and 100 mg/kg body weight, preferably between about 0.01 and 10 mg/kg, body weight.

"Pharmaceutically acceptable carriers" for therapeutic use, including diluents, are well known in the pharmaceutical art, and are described, for example, in *Remingtons Pharmaceutical Sciences*, Mack Publishing Co. (Gennaro Ed. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

The compounds of this invention may be administered by inhalation, and thus may be delivered in the form of an aerosol spray from pressurized packs or nebulizers. The compounds may also be delivered as powders, which may be formulated, and the powder composition may be inhaled with the aid of an insufflation powder inhaler device. A preferred delivery system for inhalation is the metered dose inhalation aerosol, which may be formulated as a suspension or solution of a compound of the invention in suitable propellants, such as fluorocarbons or hydrocarbons. Another preferred delivery system is the dry powder inhalation aerosol, which may be formulated as a dry powder of a compound of this invention with or without additional excipients.

The compounds of the invention can be administered in the form of a depot injection or implant preparation, which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of this invention may also be delivered by the use of monoclonal antibodies as individual carriers to which the compound molecules are coupled. The tryptase inhibitors may also be coupled with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the tryptase inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The pharmaceutical compositions of this invention may be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and, in addition, auxiliary, stabilizing, thickening and coloring agents and perfumes may be used. The active object compounds is included in the pharmaceutical composition in an amount sufficient to produce the desired effect upon the process or condition of the disease.

For the treatment of the clinical conditions and diseases noted above, the compounds of this invention may be administered orally, topically, parenterally, by inhalation spray, or rectally in dosage unit formulations containing conventional non-toxic pharmaceutically acceptable carriers, adjuvants and vehicles. The term parenteral, as used herein, includes subcutaneous injections, intravenous, intramuscular, intrasternal injection or infusion techniques.

For the treatment of certain conditions it may be desirable to employ a compound of the present invention in conjunction with another pharmacologically active agent. For example, a compound of the present invention may be presented together with another therapeutic agent as a combined preparation for simultaneous, separate, or sequential use for the relief of emesis. Such combined preparations may be, for example, in the form of a twin pack. A preferred combination comprises a compound of the present invention with a chemotherapeutic agent such as an alkylating agent, antimetabolite, mitotic inhibitor, or cytotoxic antibiotic, as described above. In general, the currently available dosage forms of the known therapeutic agents for use in such combinations will be suitable.

In the treatment of a condition associated with tryptase, an appropriate dosage level will generally be about 0.001 to 50 mg per kg of patient body weight per day, which may be administered in single or multiple doses. Preferably, the dosage level will be about 0.01 to about 25 mg/kg per day; more preferably about 0.05 to about 10 mg/kg per day. The dose and method of administration can be tailored to achieve optimal efficacy but will depend on such factors as weight, diet, concurrent medication and other factors, which those skilled in the medical arts will recognize. When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions.

The following examples are provided for purposes of illustration, not limitation. These examples illustrate the syntheses of β-strand mimetics of this invention. Specifically, the preparation of β-strand mimetics was carried out on solid phase. The solid phase syntheses of these β-strand mimetics demonstrate that libraries containing such members may be readily prepared.

TABLE 2

| ABBREVIATIONS USED IN EXAMPLES | |
|---|---|
| Reagents: | |
| AcOH | acetic acid |
| Ac$_2$O | acetic anhydride |
| BOP | benzotriazol-l-yloxy-tris(dimethylamino)phosphonium hexafluorophosphate |
| DIAD | diisoproppyl azodicarboxylate |
| DIC | diisopropyl carbonyl diimide |
| DIEA | N,N-diisopropylethylamine |
| HATU | O-(7-azabenzotriazol-l-yl)-1,1,3,3-tetramethyluronium hexafluorophosphate |
| HOAt | 1-hydroxy-7-azabenzotriazole |
| HOBt | 1-hydroxybenzotriazole hydrate |
| MCPBA | meta-chloroperoxybenzoic acid |
| PyBOP | benzotriazol-l-yloxy-tris(pyrrolidino)phosphonium hexafluorophosphate |
| TFA | trifluoroacetic acid |
| TPP | triphenylphosphine |
| Solvents: | |
| CAN | acetonitrile |
| DCM | dichloromethane |
| DMF | dimethylformamide |
| DMSO | dimethylsulfoxide |
| Et$_2$O | diethyl ether |
| MeOH | methanol |
| THF | tetrahydrofuran |
| Protecting Groups: | |
| All | allyl |
| Alloc | allyloxy carbonyl |
| Fmoc | 9-fluorenylmethoxy carbonyl |
| tButyl | tertiary-Butyl |
| Trt | triphenylmethyl |

TABLE 2-continued

ABBREVIATIONS USED IN EXAMPLES

Others:

| | |
|---|---|
| RT | room temperature |
| equiv | equivalent |
| g | gram |
| h | hour |
| min | minute |

EXAMPLES

The following examples are provided for purposes of illustration, not limitation. These examples illustrate the syntheses of β-strand mimetics of this invention.

Materials and Methods

Chemical Syntheses: Reagents, starting materials and solvents were purchased from Aldrich, Maybridge, Advanced ChemTech, ICI, Fluka Lancaster or any other source of fine chemicals where applicable. Wang polystyrene resin (loading 1.0 mmol OH/g) was purchased from Advanced ChemTech.

Analytical: $^1$H NMR spectra were recorded at 500 MHz on a Varian Unity 500 Spectrometer and are referenced to the residual protons from $CDCl_3$ or $CD_3OD$ signal (δ 7.26 ppm and δ 3.31 ppm respectively). Compound QC analyses were performed by applying the following conditions: LCMS (method A) and purification by HPLC (method B). LCMS analyses (method A) were performed on a system consisting of mass Spectrometer Micromass-Platform LCZ system and an HPLC Hewlett Packard (series 1100) equipped with Gilson 215 liquid handler as an autosampler with the following detectors: DAD 210–350 mm, ELSD (evaporative light scattering detector) and MS (ESI +/−).

Chromatographic conditions: Solvent systems; A-water (0.1% TFA), B-acetonitrile (0.1% TFA); gradients (5–95% over 3 min) at a flow rate of 0.9 mL/min. Column: Zorbax $C_{18}$ column (2.1×30 mm). Chromatographic peaks were determined by ELSD and DAD detectors and the corresponding mass spectra obtained in both positive and negative ion modes by averaging mass spectra over a 0.1 minute time-window around the top of the chromatographic peak. Chromatographic purity was established by ELSD. Preparative and Semi-prep HPLC—were employed for sample purification and the purity determined by Analytical HPLC (method B) column 5 uM 4.6×50 mm, A-water (0.1% TFA), B-acetonitrile (0.1% TFA); gradients 5–90% B in 15 min, flow rate of 1.5 ml/min.

Example 1

Synthesis of Representative β-Strand Mimetic

These examples illustrate the synthesis of representative compounds of this invention. Specifically, the preparation of compounds was carried out in solid phase. The solid phase syntheses of these compounds demonstrate that libraries containing such members may be readily prepared. Structures of representative compounds are given in Tables 3 and 4.

Reactions were carried out in, but not limited to, the following: plastic disposable syringes of the approprate size, each fitted with a polypropylene frit to retain the resin, 1–10 ml reaction vessel compatible with Symphony Automated Peptide Synthesizer (Protein Technologies), ACT 90 Synthesizer (Advanced ChemTech), Robbins block, or IRORI system.

Solid Phase Synthesis of Representative Compounds

General Reaction Scheme:
Method A1:

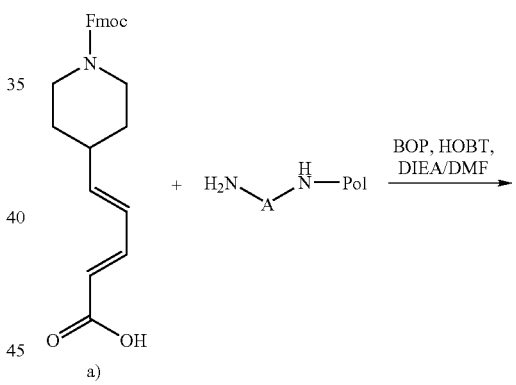

a)

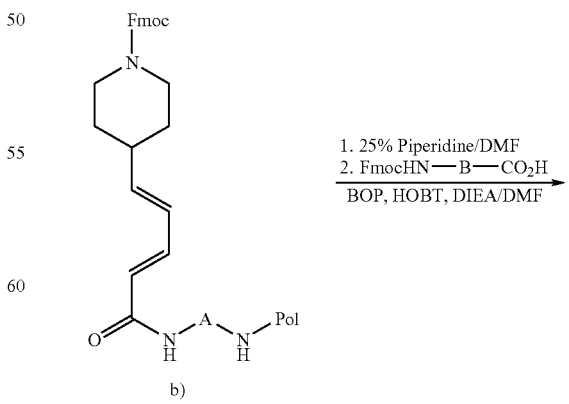

b)

-continued

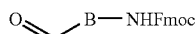

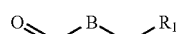

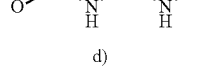

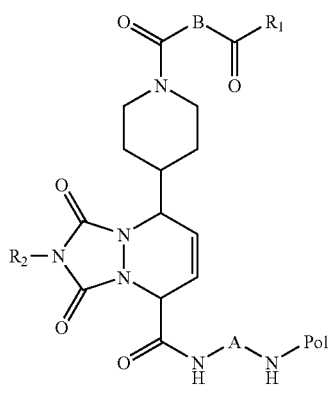

c)

d)

e)

-continued

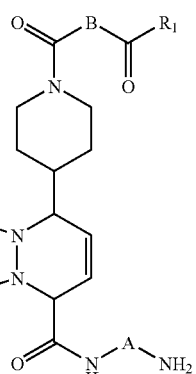

f)

In the above General Reaction Scheme, the following reaction sequence was well suited for the solid-phase synthesis. Thus, when the resin-bound amine, prepared by reacting $H_2N$-A-$NH_2$ with the commercially available Wang resin (1.0 mmol/g), was coupled to the requisite Fmoc-diene acid (a) (3.0 equiv) in the presence of BOP (3 equiv), HOBT (3 equiv) in DMF at room temperature for 4 h, the corresponding polymer-bound Fmoc-diene (b) was generated. Deprotection of the Fmoc with 25% piperidine/DMF followed by coupling with Fmoc-acid linker (FmocHN—B—$CO_2H$) employing the above conditions provided the intermediate Fmoc-diene-linker. Final Fmoc removal and subsequent coupling with Boc-protected aromatic amino acids or an equivalent thereof ($R_1$—$CO_2H$), completes the chain length and sets the stage for the penultimate Diels-Alder reaction step. Exposing this extended diene unit to the appropriate urazole (3 equiv) in the presence of [bis(trifluoroacetoxy)iodo]benzene (3 equiv) for 3 h at room temperature efficiently yielded the resin-bound compound inhibitor. The desired inhibitor was then cleaved from the resin in concert with the Boc-protecting group on treatment with 95% TFA/$H_2O$ for 90 minutes. After this time, the supernatant was collected and combined with washes (2×1 mL 95% aq TFA). The residue obtained after evaporation of the solution was redissolved in either glacial acetic acid or 50:50 acetonitrile-water, frozen and lyophilized to provide the desired crude adduct (TFA salt).

Method A2:

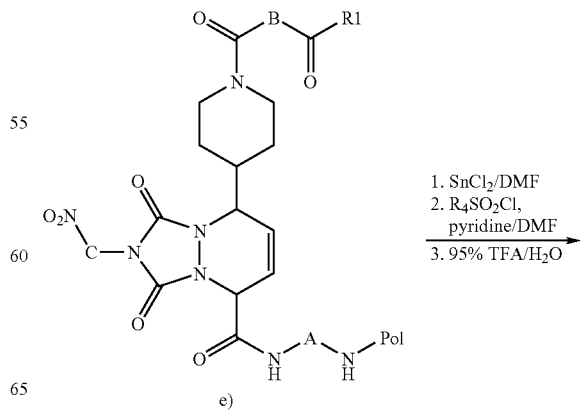

e)

-continued

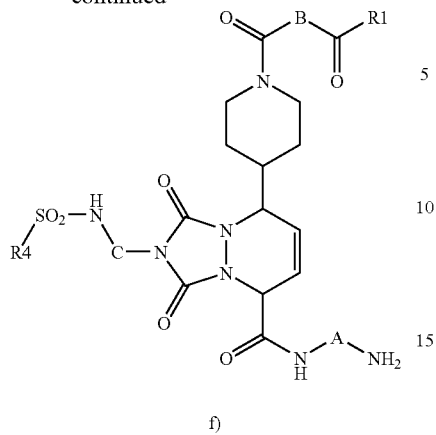

f)

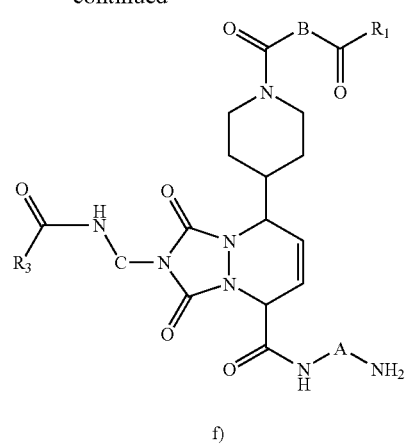

f)

In the above General Reaction Scheme, the following reaction sequence was well suited for the solid-phase synthesis. Thus, when the resin-bound amine, prepared by reacting $H_2N$-A-$NH_2$ with the commercially available Wang resin (1.0 mmol/g), was coupled to the requisite Fmoc-diene acid (a) (3.0 equiv) in the presence of BOP (3 equiv), HOBT (3 equiv) in DMF at room temperature for 4 h, the corresponding polymer-bound Fmoc-diene (b) was generated. Exposing this Fmoc-piperidine-diene unit to the Diels-Alder reaction conditions with the appropriate urazole (3 equiv) in the presence of [bis(trifluoroacetoxy)iodo]benzene (3 equiv) for 3 h at room temperature, efficiently yielded the resin-bound bicyclic compound (c). Deprotection of the Fmoc with 25% piperidine/DMF followed by coupling with Fmoc-acid linker (FmocHN—B—$C_{O2}$H) employing the above coupling conditions provided the intermediate Fmoc-diene-linker. Final Fmoc removal and subsequent coupling with Boc-protected aromatic amino acids or an equivalent thereof ($R_1$—$CO_2$H), completes the chain length and sets the stage for the cleavage step. The desired inhibitor was then cleaved from the resin in concert with the Boc-protecting group on treatment with 95% TFA/$H_2O$ for 90 minutes. After this time, the supernatant was collected and combined with washes (2×1 mL 95% aq TFA). The residue obtained after evaporation of the solution was redissolved in either glacial acetic acid or 50:50 acetonitrile-water, frozen and lyophilized to provide the desired crude adduct (TFA salt).

The general synthetic procedure is the same as given above (Method A1) except that after the Diels-Alder reaction the nitro group on the resin-bound $O_2N$—C-Urazole (e) was reduced to the aniline employing the following conditions. Stannous chloride dihydrate treatment (21 equiv, 2N solution in DMF) for 3 h at room temperature gave the intermediate aniline. The resulting aniline was acylated with aryl acid ($R_3CO_2H$) (10 equiv) in the presence of DIEA (21 equiv), PyBOP and HOBt (10 equiv each) in DMF at room temperature overnight. The desired product was then cleaved from the resin in concert with the t-boc protecting group on treatment with 95% TFA/$H_2O$ for 90 minutes. The supernatant was collected and combined with washes (2×1 mL 95% aq TFA). The residue obtained after evaporation of the solution was redissolved in either glacial acetic acid or 50:50 acetonitrile-water, frozen and lyophilized to provide the desired crude adduct (TFA salt).

Method B:

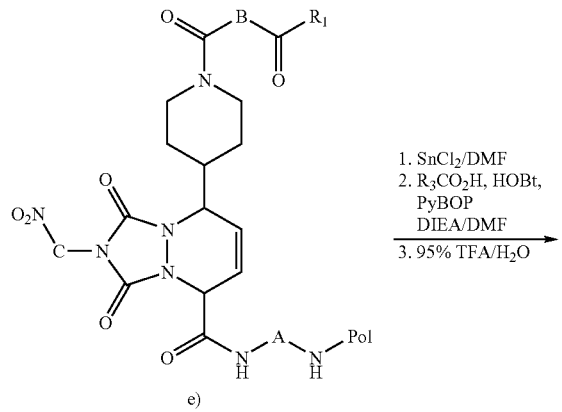

e)

Method C:

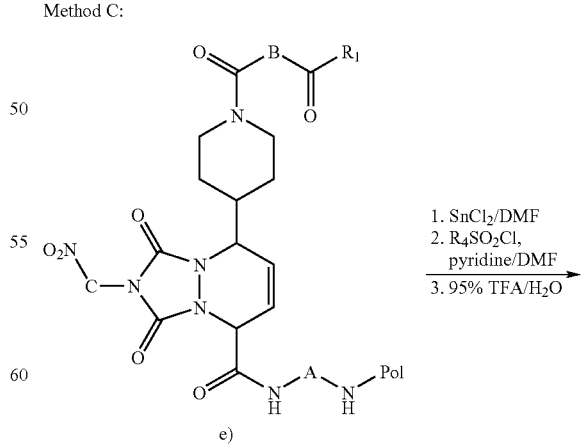

e)

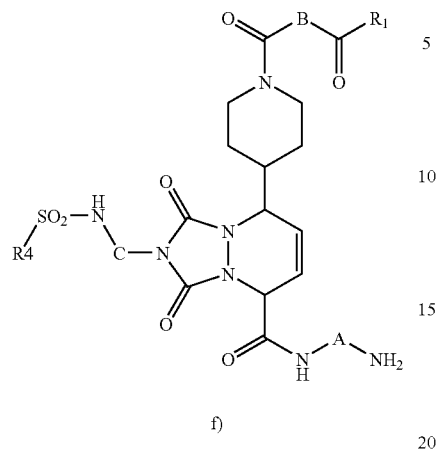

f)

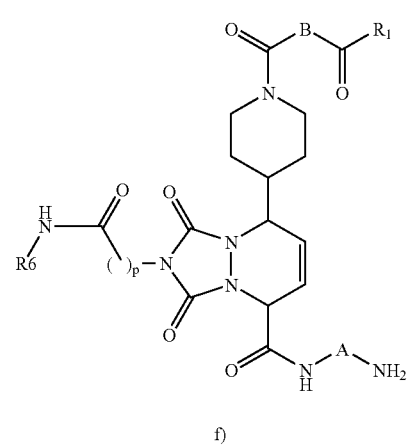

f)

The general synthetic procedure is the same as given above (Method A1) except that, after the Diels-Alder reaction, the nitro group on the resin-bound $O_2N$—C-Urazole (e) was reduced to the aniline, employing the following conditions. Stannous chloride dihydrate (21 equiv, 2N solution in DMF) for 3 h at room temperature gave the intermediate aniline. The resulting aniline was reacted with sulfonyl chloride ($R_4SO_2Cl$) (2.5 equiv) in the presence of pyridine (4 equiv) in DMF at room temperature overnight. The desired product was then cleaved from the resin in concert with the Boc-protecting group on treatment with 95% TFA/$H_2O$ for 90 minutes. The supernatant was collected and combined with washes (2×1 mL 95% aq TFA). The residue obtained after evaporation of the solution was redissolved in either glacial acetic acid or 50:50 acetonitrile-water, frozen and lyophilized to provide the desired crude adduct (TFA salt).

The general synthetic procedure is the same as given above (Method A1) except that, after the Diels-Alder reaction, the free acid (e) was reacted with amine ($H_2N$—$R_6$) (4 equiv) in the presence of DIEA (5 equiv), PyBOP and HOBt (4 equiv each) in DMF at room temperature overnight. The desired product was then cleaved from the resin in concert with the t-boc protecting group on treatment with 95% TFA/$H_2O$ for 90 minutes. The supernatant was collected and combined with washes (2×1 mL 95% aq TFA). The residue obtained after evaporation of the solution was redissolved in either glacial acetic acid or 50:50 acetonitrile-water, frozen and lyophilized to provide the desired crude adduct (TFA salt).

Method D:

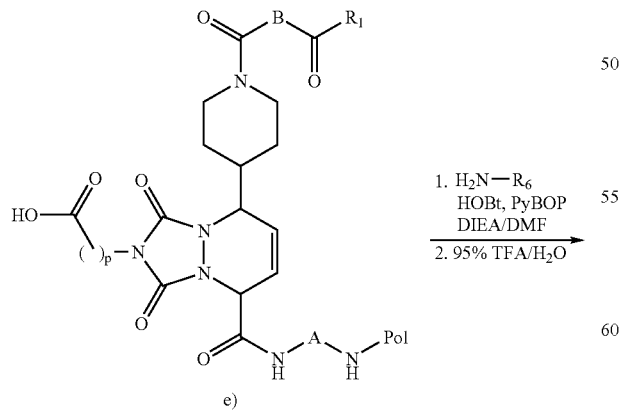

e)

1. $H_2N$—$R_6$
HOBt, PyBOP
DIEA/DMF
2. 95% TFA/$H_2O$

Method E:

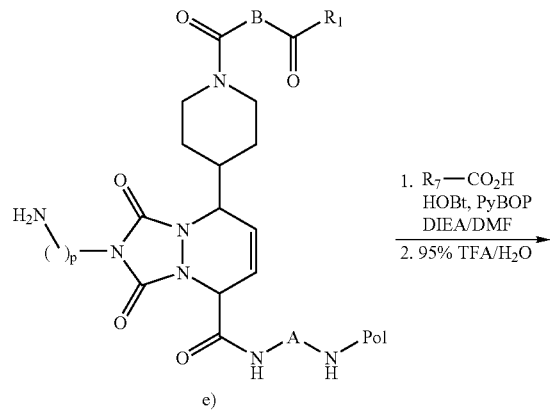

e)

1. $R_7$—$CO_2H$
HOBt, PyBOP
DIEA/DMF
2. 95% TFA/$H_2O$

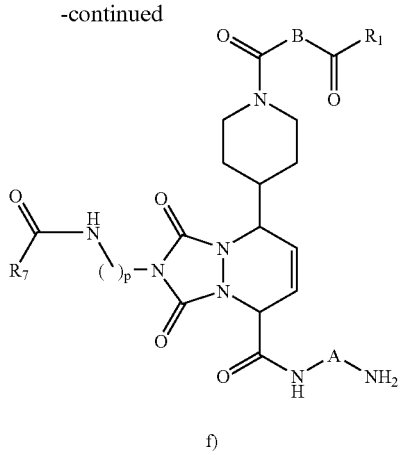

f)

The general synthetic procedure is the same as given above (Method A1) except that, after the Diels-Alder reaction, the free amine (e) was reacted with acid ($R_7$—$CO_2H$) (4 equiv) in the presence of DILA (5 equiv), PyBOP and HOBt (4 equiv each) in DMF at room temperature overnight. The desired product was then cleaved from the resin in concert with the Boc-protecting group on treatment with 95% TFA/$H_2O$ for 90 minutes. The supernatant was collected and combined with washes (2×1 mL 95% aq TFA). The residue obtained after evaporation of the solution was redissolved in either glacial acetic acid or 50:50 acetonitrile-water, frozen and lyophilized to provide the desired crude adduct (TFA salt).

Example 2

Synthesis of Representative β-Strand Mimetic

Activation of the Hydroxy Resin

Commercially available 4-hydroxymethylphenoxy resin (Wang-Resin) purchased from Advanced ChemTech was first activated with 4-nitrophenylchloroformate (5 equiv) and pyridine (4 equiv) in DCM for about an hour at −20° C., then allowed to reach room temperature and stirred overnight. The resin was filtered, washed (5× each) with DMF, DCM and $Et_2O$ and left to dry.

Coupling of the Activated Hydroxy-Resin with Diamines

The resin is treated with (10–15 equiv) of a 2M solution of the appropriate diamine in DMF at room temperature for 15 h after which, the resin was filtered and washed repeatedly with DMF until the wash became colorless. Additional washings carried out with DCM and $Et_2O$ (5× each) provided the clean amine-resin. After drying, the loading was determined by measuring the UV absorbance on a small portion via Fmoc protection and cleavage protocol.

General Diene Extension Via Coupling to the Amine on Resin

The amine-bound resin was coupled to Fmoc-protected diene acid (3 equiv) in the presence of BOP (3 equiv), HOBT (3 equiv) and DIEA (4.5 equiv) in DMF for 3 h at which time a negative Kaiser test was obtained. Then Fmoc group was cleaved with 25% (v/v) piperidine/DMF for 10 minutes giving a positive chloranil test. Treatment of the newly unmasked amine functionality with 3 equiv of the appropriate acid linker in the presence of BOP (3 equiv), HOBT (3 equiv) and DIEA (4.5 equiv) in DMF gave a negative chloranil test within 5 h of reaction time. Removal of the Fmoc group from the linker, as described above, was confirmed by a positive Kaiser analysis. The chain was capped by reacting the freed amino group with Boc-amino acid derivative (3 equiv) employing the above coupling conditions and washing cycles.

General Diels-Alder Reaction Procedure

With the desired chain length assembled, the Diels-Alder chemistry was carried out by reacting the diene-resin with 3 equiv each of the appropriate urazole and [bis(trifluoroacetoxy)iodo]benzene in DMF for 3.5 h at room temperature, yielding the bicyclic compound after the usual washings.

Method F:

The dried resin was reswollen in DCM and drained. The product was then cleaved from the resin by treatment with 95% (v/v) TFA/$H_2O$ at room temperature for 1.5 h. The supernatant was collected and combined with washes and evaporated in a speed vac. The residue obtained after evaporation of the solution was redissolved in either glacial acetic acid or 50:50 acetonitrile-water, frozen and lyophilized to provide the desired product.

Method G:

The dried resin was preswollen in DCM and drained. The product was then cleaved from the resin by treatment with 4N HCl in dioxane at room temperature for 3 h. The supernatant was collected and combined with washes (acetonitrile-$H_2O$, 1:1, 4×5 mL) and evaporated. The residue obtained after evaporation of the solution was redissolved in either glacial acetic acid or 50:50 acetonitrile-water, frozen and lyophilized to provide the desired product.

Example 3

Synthesis of Representative β-Strand Mimetic

Synthesis of Component Pieces

Synthesis of Aminomethyl Cyclohexane Amine Resin (3)

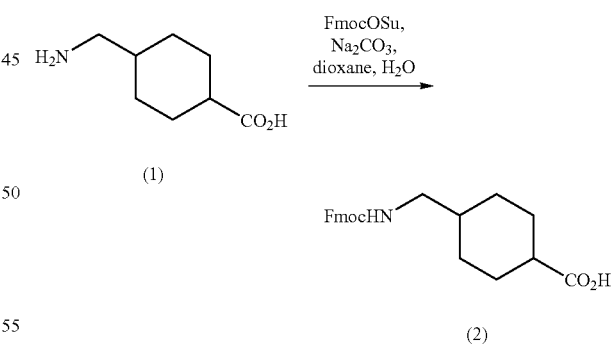

Aminomethylcyclohexane carboxylic acid (1) (20 g, 127 mmol) and sodium carbonate (13.6 g, 128 mmol) were dissolved in 600 mL of water, then a solution of FmocOSu (40 g, 118 mmol) was added over a period of 30 min with stirring. The mixture was stirred overnight, during which a large amount of white precipitate formed. The mixture was acidified to pH=3 with 1N HCl, then diluted with 2 L of ethyl acetate. The organic layer was separated, washed with 5% aqueous citric acid, water and brine. The organic layer was dried over anhydrous sodium sulfate, filtered and cooled in a freezer overnight. The solid was filtered off, then the filtrate was concentrated to ca. 1 L and cooled overnight. The solid was filtered and combined with the previously collected solid (2) then dried in a desiccator.

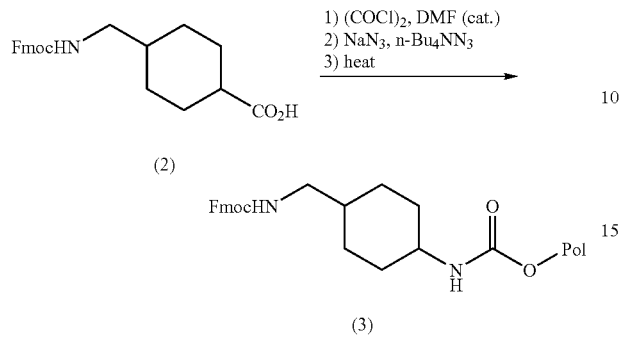

The Fmoc aminomethylcyclohexyl carboxylic acid (2) was taken up in 1 L of dichloromethane. Oxalyl chloride (39 mL, 450 mmol) was added, followed by DMF (10 drops) and the mixture was stirred for 1 h. The mixture was concentrated under vacuum and the residue was dissolved in 1 L of toluene, and a solution of sodium azide (18.4 g, 280 mmol) in 30 mL of water was added along with 3.4 g (12 mmol) of tetrabutylammonium azide. Due to low solubility, an additional 2 L of toluene was added, and the mixture was stirred vigorously until the IR spectrum of an aliquot showed a peak for the acyl azide (2120 cm$^{-1}$). The mixture was filtered, and the solid set aside (unreacted acid chloride). The filtrate was extracted with 5% aqueous citric acid (2×200 mL) and brine (200 mL) then the toluene solution was dried over anhydrous sodium sulfate and filtered. The solution was heated to reflux until the IR spectrum of an aliquot of the solution showed an isocyanate peak (2230 cm$^{-1}$) and loss of the acyl azide peak. The solution was evaporated to give 31 g of solid. The solid was dissolved in dichloromethane (800 mL) and stirred with Wang resin (57 g, 54 mmol) and 4N HCl in dioxane (1.5 mL) was added. The mixture was stirred overnight then filtered. The resin (3) was washed with DMF (3×800 mL), dichloromethane (3×800 mL) and diethyl ether (3×800 mL) then dried in a vacuum desiccator.

Synthesis of 4-({[Benzyloxy)carbonyl]amino}methyl)benzoic acid (4)

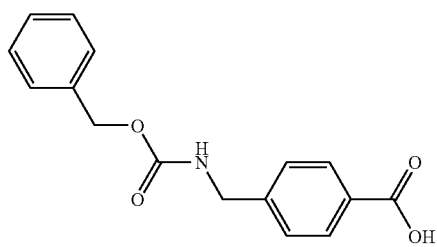

Aminomethyl benzoic acid (6.0 g, 39.7 mmol) and Na$_2$CO$_3$ (8.41 g, 79.4 mmol) were dissolved in H$_2$O (40 mL). To this mixture was added a solution Cbz-Osu (10.4 g, 41.7 mmol) in THF (40 mL). The resulting solution was stirred at room temperature overnight, then concentrated. The residue was acidified with 2N HCl to pH=2, which led to a solid precipitate. The product was collected by filtration and dried in vacuum overnight to give 9.6 g, 85% of a white solid (4).

Synthesis of Benzyl 4-(aminocarbonyl)benzylcarbamate (5)

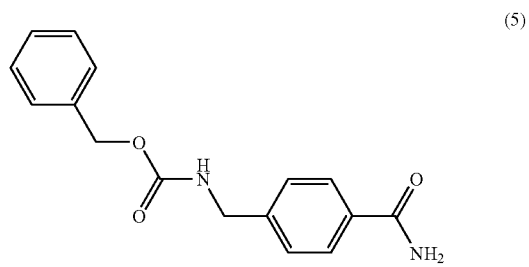

To the above solid (4) (2.0 g, 7.0 mmol) in DCM (20 mL) was added oxalyl chloride (2.0 mL) at room temperature and then DMF (40 μL) was added slowly to the solution. After the reaction mixture was stirred for 2 h, the solution was concentrated. The residue was redissolved in DCM (10 mL) and treated with 28% aqueous ammonia solution (20 mL) at 0° C. and stirred for 1 h at this temperature. The solid product formed was collected by filtration, washed with water and dried in vacuum overnight to provide a white solid (5) (1.95 g, 98%).

Synthesis of Benzyl 4-(aminocarbothionyl)benzylcarbamate (6)

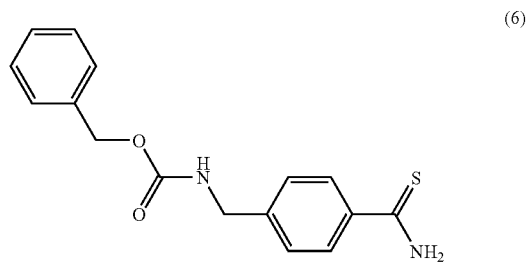

To the amide (5) (2.0 g, 7.0 mmol) in THF (20 mL) was added Lawesson's reagent (1.42 g, 3.5 mmol). The mixture was heated at reflux for 3 h and concentrated to dryness before a slow addition of DCM (10 mL). After stirring for 2 h, the yellow solid produced was collected by filtration, washed with cold DCM and dried under vacuum to afford 1.68 g, 80% of the desired product (6).

Synthesis of Benzyl 4-[[tert-butoxycarbonyl)amino](imino)methyl]benzylcarbamate (7)

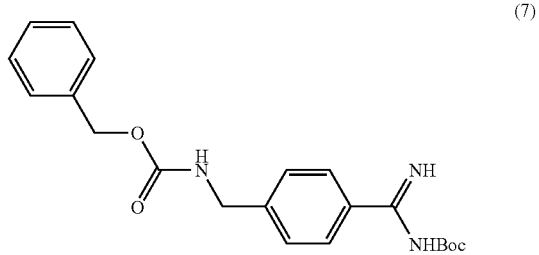

A suspension of the thioamide (6) (1.0 g, 3.3 mmol) in DCM/CH$_3$Cl mixture (4/1, 10 mL) was heated at reflux for 3 h until completely dissolved. The solution was concentrated to give a thick oil. The oil was dissolved in MeOH (5.0 mL) and added to a solution of ammonium formate (0.8 g, 10.0 mmol) in MeOH (10 mL) and stirred at room temperature overnight. This led to the formation of a white solid that was filtered and washed with cold MeOH. The solid was dissolved in THF/water (5:1, 20 mL) and TEA (1.4 mL, 10.0 mmol) was added. The mixture was stirred for 30 min at 0° C., then treated with a solution of Boc$_2$O (0.8 g, 3.4 mmol) in THF (2.0 mL). After stirring for 24 h, the product was extracted with ethyl acetate (3×50 mL). The combined organic layers were washed with brine, dried with magnesium sulfate and concentrated. The residue was slurried with ether for 1 h, then filtered to provide an off-white solid product, benzyl 4-[[tert-butoxycarbonyl)amino](imino)methyl]benzylcarbamate (7) (1.1 g, 88%). $^1$H NMR (300 MHz, CDCl$_3$) δ 7.79 (d, J=8.3 Hz, 2H), 7.33 (m, 7H), 5.19 (bs, 1H), 5.16 (s, 2H), 4.42 (d, J=6.0 Hz, 2H), 1.56 (s, 9H).

Synthesis of tert-Butyl [4-(aminomethyl)phenyl(imino)methylcarbamate (8)

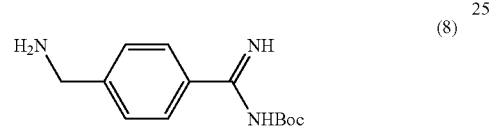

Benzyl 4-[[tert-butoxycarbonyl)amino](imino)methyl]benzylcarbamate (7) (2.5 g, 6.5 mmol) in 80 mL of methanol was stirred with 1.3 g of Pd—C (5 wt % Degussa type E101 NO/W, 50% H$_2$O) under hydrogen atmosphere for 1.5 h. The catalyst was removed by filtration and the solvent evaporated in vacuo yielding 1.51 g (93%) of the free amine (8). $^1$H NMR (500 MHz, CDCl$_3$) δ 7.79 (br s, 2H), 7.36 (br s, 2H), 3.92 (br s, 2H), 1.54 (s, 9H); MS (ES+) m/z 250.44 (M+H$^+$).

Synthesis of 9H-Fluoren-9-ylmethyl4-[[(tert-butoxycarbonyl)amino(imino)methyl]benzyl carbamate (9)

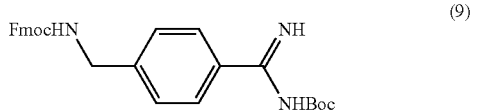

To the Boc-amidine (8) (4.71 g, 18.9 mmol) in THF (100 mL) was added 15 mL saturated NaHCO$_3$ solution, then followed by (6.4 g, 19 mmol) of Fmoc-Osu. The mixture was stirred at room temperature overnight. Ethyl acetate/water (1:1, 50 mL) was added and the layers separated. The aqueous layer was further extracted with ethyl acetate (3×100 mL). The combined organic layers were washed with brine, dried over MgSO$_4$ and evaporated in vacuo. Purification by column chromatography on silica gel with DCM/MeOH (95:5) yielded (6.72 g, 76%) of the product (9). $^1$H NMR (500 MHz, CDCl$_3$) δ 7.83 (d, J=8.0 Hz, 2H), 7.76 (d, J=7.5 Hz, 2H), 7.59 (d, J=7.0 Hz, 2H), 7.40 (t, J=7.5 Hz, 3H), 7.31 (t, J=7.5 Hz, 3H), 4.44 (d, J=7.0 Hz, 2H), 4.38 (d, J=6.0 Hz, 2H), 4.22 (t, J=6.0 Hz, 1H), 1.57 (s, 9H); MS (ES+) m/z 472.45 (M+H$^+$).

Synthesis of 9H-Fluoren-9-ylmethyl 4-[amino(imino)methyl]benzylcarbamate (10)

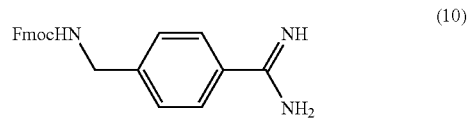

To Fmoc-Boc-amidine (9) (6.72 g, 14.2 mmol) was added 4N HCl in Dioxane (50 mL). After stirring at room temperature for 2 h, the solvent was removed in vacuo to give the HCl salt (10) that was used as is in the next step. MS (ES+) m/z 372.41 (M+H$^+$).

Synthesis of the resin-bound 9H-Fluoren-9-ylmethyl 4-[amino(imino)methyl]benzyl carbamate (11):

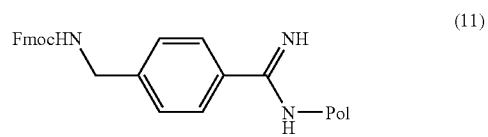

For loading onto the resin, 14.2 mmol of the crude free amidine (10) was premixed with DIEA (6.2 mL, 35 mmol) in 40 mL of DMF and added to (4.2 g, 7.1 mmol) of p-nitrophenyl Wang resin in DMF. The mixture was shaken for 5.5 h, and the resin filtered and washed with DCM, MeOH, DMF, MeOH and Ether (2× each) to yield 5.8 g of resin (11) (loading=0.71 mmol/g).

Synthesis of tert-Butyl 3-[methoxy(methyl)amino]-3-ocopropylcarbate (13)

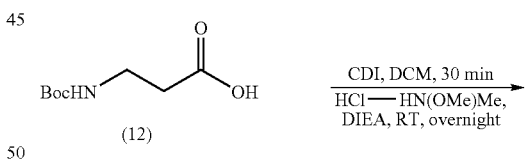

To a solution of Boc-β-alanine (12) (1.0 g, 5.28 mmol) in DCM (30 mL) was added N,N'-carbonyldiimidazole (856 mg, 5.81 mmol), followed by stirring at room temperature for 30 min. Diisopropylethylamine (1.0 mL, 5.81 mmol) and Weinreb amine (567 mg, 5.81 mmol) were added and the mixture stirred overnight. The solution was diluted with DCM (100 mL), washed with 5% citric acid (30 mL) and brine (30 mL), dried (MgSO$_4$) and concentrated to obtain a colorless oil (13) (1.21 g, 99%). $^1$H NMR (400 MHz, CDCL$_3$) δ 5.22 (br s, 1H), 3.68 (s, 3H), 3.41 (m, 2H), 3.18 (s, 3H), 2.63 (m, 2H), 1.42 (s, 9H); MS (ESI+) m/z 133.29 (M+H$^+$-boc).

Synthesis of tert-Butyl 3-oxopropylcarbate (14)

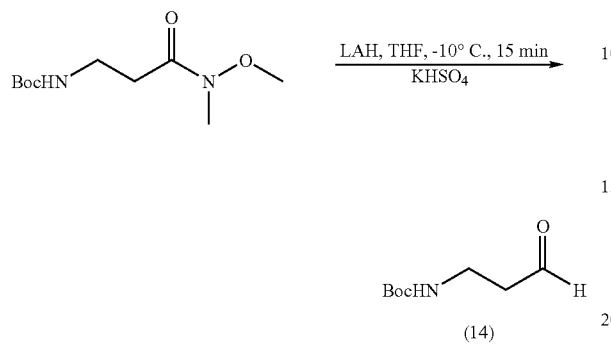

(14)

To a stirred solution of the above Weinreb amide (13) (930 mg, 4.01 mmol) in THF (20 mL), at –10° C., was added LiAlH$_4$ (2.1 ml, 2.1 mmol, 1M in ether). After the starting material was consumed completely (10–20 min), a saturated solution of KHSO$_4$ in H$_2$O (30 mL) was added slowly. The mixture was diluted with ether, stirred for 15 minutes and extracted with EtOAc (3×50 mL). The combined organic extracts were washed with saturated NaHCO$_3$ (50 mL), brine (50 mL), dried (MgSO$_4$), and concentrated to give an oil (14) (670 mg, 97%). $^1$H NMR (400 MHz, CDCL$_3$) δ 9.80 (s, 1H), 4.89 (br s, 1H), 3.41 (m, 2H), 2.70 (m, 2H), 1.42 (s, 9H); MS (ESI+) m/z 118.31 (M+H$^+$-isobutylene).

Synthesis of Ethyl (2E, 4E)-7-[(tert-Butoxycarbonyl)amino]-2,4-heptadienoate (15)

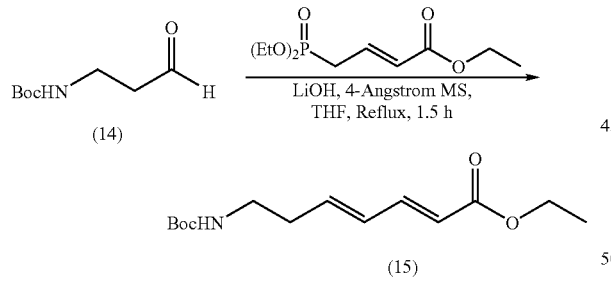

(15)

A mixture of the above aldehyde (14) (400 mg, 2.31 mmol), triethyl trans-4-phosphono-2-butenoate (760 mg, 2.77 mmol), LiOH—H$_2$O (116 mg, 2.77 mmol) and 4A molecular sieve (1.2 g) in THF (20 mL) was heated at reflux 1.5 hours. The molecular sieve was filtered through a short pad of Celite and washed with EtOAc (100 mL) and the filtrate concentrated to give sticky brown oil. The oily residue was diluted with 5% citric acid and extracted thrice with 100 mL of EtOAc. The combined extracts were washed with NaHCO$_3$, brine, then dried over Na$_2$SO$_4$ and concentrated. Purification by flash chromatography (EtOAc:Hexanes=1:5) gave a colorless oil (15) (315 mg, 50%) of the desired compound. $^1$H NMR (400 MHz, CDCL$_3$) δ 7.24 (dd, J=15.2, 10.8 Hz, 1H), 6.22 (dd, J=15.2, 10.8 Hz, 1H), 6.04 (quintet, J=7.2 Hz, 1H), 5.81 (d, J=15.2 Hz, 1H), 4.55 (br s, 1H), 4.19 (q, J=7.0 Hz, 2H), 3.23 (m, 2H), 2.36 (m, 2H), 1.43 (s, 9H), 1.29 (t, J=7.0 Hz, 3H); MS (ESI+) m/z 170.29 (M+H$^+$-boc).

Synthesis of (2E, 4E)-7-[(tert-Butoxycarbonyl)amino]-2,4-heptadienoic acid (16)

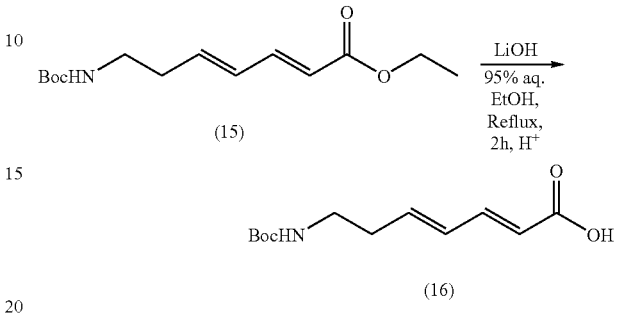

(16)

To a solution of the above ethyl ester (15) (140 mg, 0.52 mmol) in absolute EtOH (4 mL) was added LiOH—H$_2$O (0.75 mL, 1.5 mmol, 2N solution in water). The reaction was heated at 50° C. for 1 h, then concentrated to remove excess EtOH. After acidification with 5% citric acid (20 mL), the product was extracted with EtOAc (2×50 mL). The combined organic extracts were washed with brine (30 mL), dried (MgSO$_4$) and concentrated to give a white solid (16) (110 mg, 88%). $^1$H NMR (400 MHz, CDCL$_3$) δ 7.31 (dd, J=15.2, 10.8 Hz, 1H), 6.25 (dd, J=15.2, 10.8 Hz, 1H), 6.11 (quintet, J=7.2 Hz, 1H), 5.81 (d, J=15.2 Hz, 1H), 4.58 (br s, 1H), 3.24 (m, 2H), 2.37 (m, 2H), 1.44 (s, 9H); MS (ESI–) m/z 240.11 (M–H$^+$).

Synthesis of (2E,4E)-7-{[(9H-Fluoren-9-ylmethoxy)carbonyl]amino}-2,4-heptadienoic acid (17)

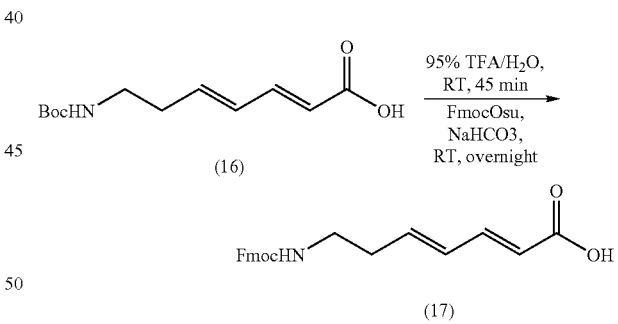

(17)

To the above Boc-compound (16) (1.50 g, 6.2 mmol) in DCM (10 mL) was added 5 mL of TFA. The mixture was stirred at room temperature for 1 h and concentrated to give a yellow solid. The above solid was taken up in sat NaHCO$_3$ (50 mL)/THF (50 mL). To this was added Fmoc-Osu (2.14 g, 6.3 mmol) at room temperature. The suspension became clear within 30 min. After stirring at room temperature overnight, the solution was concentrated to remove organic solvent, and the resulting white suspension was acidified with 1 N HCl (50 mL) and extracted with EtOAc (3×100 mL). The combined organic extracts were dried (MgSO$_4$) and concentrated to give a white solid (17) (2.2 g, 98%). MS (ES+) m/z 386.19 (M+Na$^+$).

Synthesis of 1-(tert-Butoxycarbonyl)-4-piperidinecarboxylic acid (19)

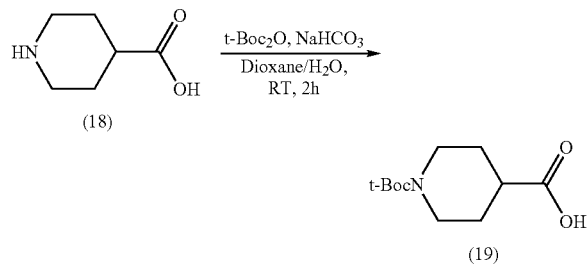

A solution of isonipecotic acid (18) (2.6 g, 20 mmol) in 1,4-dioxane/H$_2$O (3:2, 100 mL) was treated with NaHCO$_3$ (8.4 g, 100 mmol, 20 mL H$_2$O), followed by t-Boc$_2$O (4.8 g, 22 mmol) at room temperature. After stirring for 3 h, the solution was acidified with 1 N HCl (50 mL), extracted with EtOAc (3×100 mL). The combined organic extracts were washed with saturated solution of NaHCO$_3$ (50 mL), brine (50 mL), dried over MgSO$_4$ and concentrated to give a white solid (19) (4.16 g, 91%). $^1$H NMR (500 MHz, CDCl$_3$) δ 4.02 (br s, 2H), 2.86 (t, J=12.0 Hz, 2H), 2.50 (tt, J=11.0, 4.0 Hz, 1H), 1.91 (dd, J=13.0, 2.5 Hz, 2H), 1.65 (m, 2H), 1.46 (s, 9H), MS (ESI−) m/z 228.65 (M−H$^-$).

Synthesis of tert-Butyl-4-{[methoxy(methyl)amino]carbonyl}-4-piperidinecarboxylate (20)

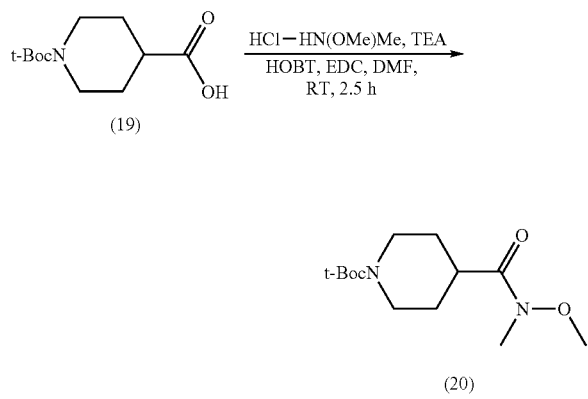

To a stirring suspension of t-Boc-isonipecotic acid (19) (2.34 g, 10.2 mmol) and the Weinreb amine (1.5 g, 15 mmol) in DMF (50 mL), was added triethylamine (2.8 mL, 20 mmol) at room temperature. After stirring for 10 min, HOBt (1.62 g, 12 mmol) was added, followed by EDCI (2.3 g, 12 mmol). The resulting solution was stirred overnight and concentrated. The residue was taken up in 1 N HCl (100 mL) and extracted with EtOAc (3×100 mL). The combined organic extracts were washed with sat NaHCO$_3$ (50 mL), brine (50 mL), dried (MgSO$_4$) and concentrated to obtain a colorless oil (20) (2.79 g, >100%). $^1$H NMR (500 MHz, CDCL$_3$) δ 4.14 (m, 2H), 3.71 (s, 3H), 3.19 (s, 3H), 2.78 (m, 3H), 1.68 (m, 4H), 1.46 (s, 9H); MS (ESI+) m/z 217.72 (M+H$^+$-isobutylene).

Synthesis of tert-Butyl 4-formyl-1-piperidinecarboxylate (21)

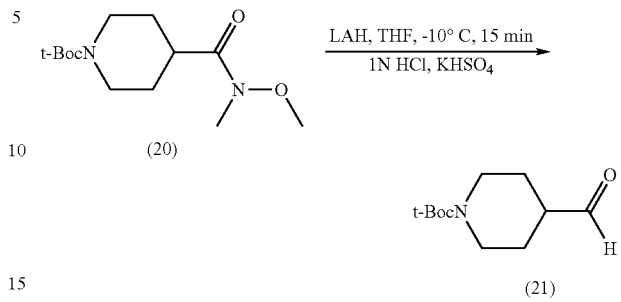

To a stirred solution of the above Weinreb amide (20) (2.70 g, 10 mmol) in THF (100 mL) at −10° C. was added LiAlH$_4$ (460 mg, 12 mmol). After the starting material was consumed completely (10–20 min), a solution of KHSO$_4$ (2.8 g) in H$_2$O (100 mL) was added slowly, then followed by 1 N HCl (50 mL). The mixture was stirred for 15 minutes and extracted with EtOAc (3×100 mL). The combined organic extracts were washed with sat NaHCO$_3$ (50 mL), brine (50 mL), dried (MgSO$_4$), and concentrated to give an oil (21) (2.14 g, 100%). $^1$H NMR (500 MHz, CDCL$_3$) δ 9.66 (s, 1H), 3.98 (br d, J=11.5 Hz, 2H), 2.93 (m, 2H), 2.41 (m, 1H), 1.90 (m, 2H), 1.55 (m, 2H), 1.46 (s, 9H); MS (ESI+) m/z 158.67 (M+H$^+$-isobutylene).

Synthesis of tert-Butyl 4-[(1E,3E)-5-ethoxy-5-oxo-1,3-pentadienyl]-1-piperidine-carboxylate (22)

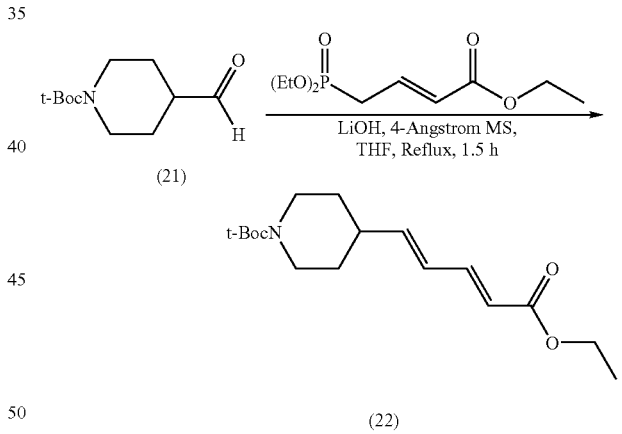

A mixture of the above aldehyde (21) (2.10 g, 10 mmol), triethyl trans-4-phosphono-2-butenoate (3.0 g, 12 mmol), LiOH—H$_2$O (510 mg, 12 mmol) and 4A molecular sieve (5 g) in THF (100 mL) was heated at reflux 1.5 hours. The molecular sieve was filtered through a short pad of Celite and washed with EtOAc (100 mL) and the filtrate concentrated to give sticky brown oil. The oily residue was diluted with 5% citric acid and extracted thrice with 100 mL of EtOAc. The combined extracts were washed with NaHCO$_3$, brine, then dried over Na$_2$SO$_4$ and concentrated. Purification by flash chromatography (EtOAc:Hexanes=1:5) gave a white solid (22) (2.95 g, 95%) of the desired compound. $^1$H NMR (500 MHz, CDCL$_3$) δ 7.24 (dd, J=15.5, 10.5 Hz, 1H), 6.16 (dd, J=15.5, 10.5 Hz, 1H), 6.04 (dd, J=15.5, 7.0 Hz, 1H), 5.82 (d, J=15.5 Hz, 1H), 4.20 (q, J=7.0 Hz, 2H), 4.10

(m, 2H), 2.75 (m, 2H), 2.25 (m, 1H), 1.71 (m, 2H), 1.46 (s, 9H), 1.34 (m, 2H), 1.29 (t, J=7.0 Hz, 3H); MS (ESI+) m/z 210.75 (M+H+-boc).

Synthesis of (2E,4E)-5-[1-(tert-Butoxycarbonyl)-4-piperidinyl]-2,4-pentadienoic acid (23)

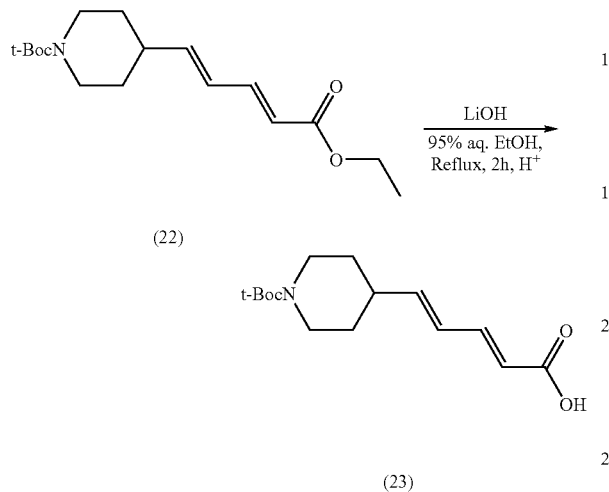

A solution of the above ethyl ester (22) (2.60 g, 8.4 mmol) in absolute EtOH (30 mL) was added LiOH—H₂O (720 mg, 17 mmol, in 10 mL of water). The reaction was heated to 50° C. for 1 h, then concentrated to remove excess EtOH. After acidification with 5% citric acid (50 mL), the product was extracted with EtOAc (2×100 mL). The combined organic extracts were washed with brine (100 mL), dried (MgSO₄) and concentrated to give a white solid (23) (2.32 g, 98%). ¹H NMR (500 MHz, CDCL₃) δ 7.31 (dd, J=15.5, 11.0 Hz, 1H), 6.18 (dd, J=15.5, 11.0 Hz, 1H), 6.08 (dd, J=15.5, 7.0 Hz, 1H), 5.80 (d, J=15.5 Hz, 1H), 4.10 (m, 2H), 2.75 (m, 2H), 2.25 (m, 1H), 1.70 (m, 2H) 1.44 (s, 9H), 1.33 (m, 2H); MS (ESI–) m/z 280.74 (M–H+).

Synthesis of (2E,4E)-5-(4-piperidinyl)-2,4-pentadienoic acid (24)

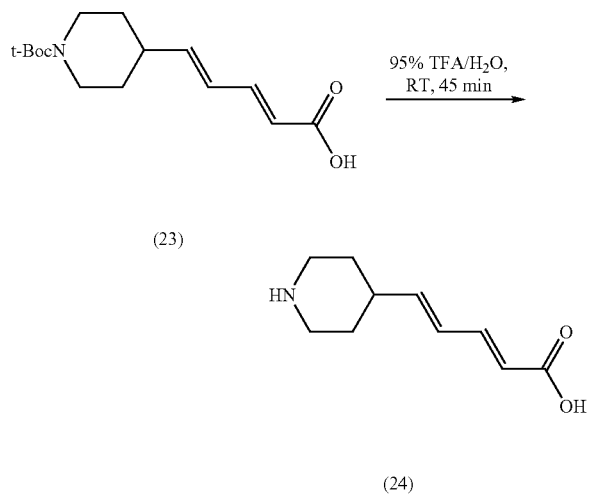

To the above Boc-compound (23) (2.50 g, 8.4 mmol) in DCM (20 mL) was added 10 mL of TFA. The mixture was stirred at room temperature for 1 h and concentrated to give a yellow solid (24). ¹H NMR (500 MHz, CD₃OD) δ 7.25 (dd, J=15.5, 11.0 Hz, 1H), 6.34 (dd, J=15.5, 11.0 Hz, 1H), 6.12 (dd, J=15.5, 7.0 Hz, 1H), 5.87 (d, J=15.5 Hz, 1H), 3.41 (m, 2H), 3.04 (dd, J=12.5, 2.5 Hz, 2H), 2.50 (m, 1H), 2.00 (m, 2H), 1.62 (m, 2H); MS (ESI–) m/z 182.73 (M–H+).

Synthesis of (2E,4E)-5-{1-[(9H-fluoren-9-ylmethoxy)carbonyl]-4-piperidinyl}-2,4-pentadienoic acid (25)

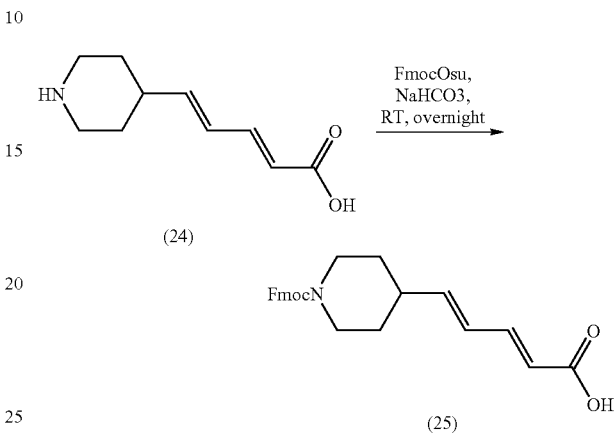

The above solid (24) was taken up in saturated NaHCO₃ (50 mL)/THF (50 mL). To this was added Fmoc-Osu (3.0 g, 9.0 mmol) at room temperature. The suspension became clear within 30 min. After stirring at room temperature overnight, the solution was concentrated to remove organic solvent, the resulting white suspension was acidified with 1 N HCl (50 mL) and extracted with EtOAc (3×100 mL). The combined organic extracts were dried (MgSO₄) and concentrated to give a white solid (25) (3.63 g, >100%). ¹H NMR (500 MHz, CDCL₃) δ 7.77 (d, J=7.5 Hz, 2H), 7.58 (d, J=8.0 Hz, 2H), 7.40 (t, J=7.5 Hz, 2H), 7.34 (dd, J=15.0, 11.0 Hz, 1H), 7.32 (t, J=7.5 Hz, 2H), 6.21 (dd J=15.0, 11.0 Hz, 1H), 6.09 (dd, J=15.0, 7.0 Hz, 1H), 5.85 (d, J=15.5 Hz, 1H), 4.45 (br s, 2H), 4.18 (m, 3H), 2.83 (br s, 2H), 2.31 (m, 1H), 1.72 (m, 2H), 1.26 (m, 2H); MS (ES+) m/z 404.81 (M+H+).

Synthesis of 4-(4{[(9H-Fluoren-9-ylmethoxy)carbonyl]amino}phenyl)butanoic acid (26)

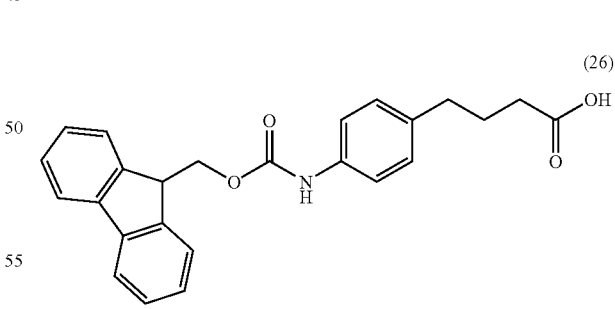

To a suspension of 4-(4-aminophenyl)butyric acid (3.0 g, 16.7 mmol) in 30 mL of saturated NaHCO₃ was added Fmoc-Osu and 20 mL of THF. The mixture was stirred at room temperature overnight. After dilution with 1 N HCl, the product was extracted with ethyl acetate (3×100 mL). The combined extracts were washed with dilute HCl, brine, dried (Na₂SO₄) and concentrated to give a white solid 6.6 g (26) (98%). ¹H NMR (500 MHz, CD₃OD) δ 7.80 (m, 2H), 7.70 (m, 2H), 7.39 (m, 3H), 7.32 (m, 4H), 7.90 (m, 2H), 4.46

(m, 2H), 4.27 (t, J=7.0 Hz, 1H), 2.60 (t, J=8.0 Hz, 2H), 2.28 (t, J=7.0 Hz, 2H), 1.87 (m, 2H); MS (ESI+) m/z 424.19 (M+Na+).

Synthesis of tert-Butyl 4-(aminomethyl)benzylcarbamate (27)

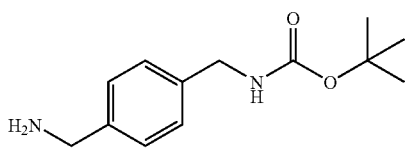
(27)

A solution of t-Boc$_2$O (1.6 g, 7.34 mmol) in DCM (30 mL) was added dropwise over 45 minutes to a stirring solution of 1,4-bis(aminomethyl)xylene (2.0 g, 14.7 mmol) and TEA (5 mL, 36.7 mmol) in 50 mL of DCM. After stirring for 4 h, the reaction was diluted with water and extracted thrice with 75 mL each of DCM. The combined extracts were washed with water, 5% citric acid, brine, dried (Na$_2$SO$_4$) and concentrated, to give a white solid 0.73 g (27) (42%). $^1$H NMR (500 MHz, CD$_3$OD) δ 7.26 (m, 5H), 4.83 (br s, 1H), 4.29 (m, 2H), 3.85 (s, 2H), 1.46 (s, 9H); MS (AP+) m/z 237.4 (M+H+).

Synthesis of 4-[(4-{[(tert-Butoxycarbonyl)amino]methyl}benzyl)amino]-4-oxobutanoic acid (28)

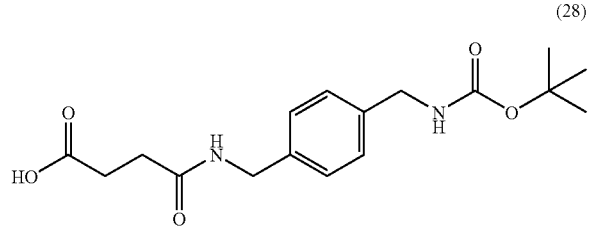
(28)

A mixture of the above compound (27) (2.0 g, 8.5 mmol) and succinic anhydride (0.85 g, 8.5 mmol) in DCM (50 mL) were stirred at 36° C. for several hours. The product was diluted with 5% citric acid and extracted with DCM (3×50 mL). The combined extracts were washed with brine and dried over MgSO$_4$ to give 2.1 g (28) (72%) of the desired compound. MS (ESI−) m/z 335.23 (M−H+).

The Synthesis of 4-(1-Naphthylmethyl)-1,2,4-triazolidine-3,5-dione (30)

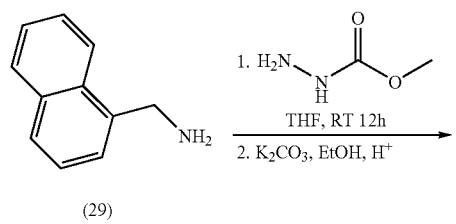
(29)

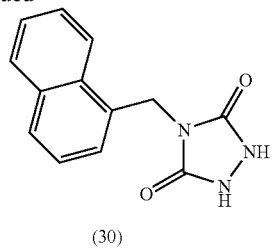
(30)

Methyl hydrazinocarboxylate (14.3 g, 159.0 mmol) was dissolved in THF (500 mL) under argon. 1,1-carbonyldiimidazole (25.8 g, 159.0 mmol) was added and the mixture stirred for 15 min at room temperature. 1-Aminomethylnaphthalene (25.0 g, 159.0 mmol) was added and the mixture stirred overnight. The reaction was evaporated to dryness. DCM (200 mL) was added and the solution cooled at −20° C. for 2 h, to this was added 100 mL of Et$_2$O. The product was collected by filtration, washed with Et$_2$O (2×150 mL) and dried to give 30.2 g (69%) of the product as an off-white solid. The crude product was heated at reflux for 6 h with K$_2$CO$_3$ (30.5 g, 220.6 mmol) in 400 mL of MeOH, then, concentrated to dryness. The residue was redissolved in water (250 mL) and washed with 300 mL of ethyl acetate. The aqueous layer was acidified with conc. HCl (pH=1–2), which led to product precipitation. After filtration, the product was washed with water (2×200 mL) and vacuum-dried overnight to give 17.1 g (64%) of an off-white solid (30). $^1$H NMR (500 MHz, DMSOD$_6$) δ 10.27 (s, 2H), 8.27 (d, J=8.5 Hz, 1H), 7.95 (d, J=8.5 Hz, 1H), 7.86 (d, J=8.5 Hz, 1H), 7.55 (m, 2H), 7.46 (t, J=(d, J=8.0 Hz, 1H), 7.32 (d, J=7.0 Hz, 1H), 5.00 (s, 2H); MS (ESI+) m/z 242.22 (M+H+).

Example 4

Synthesis of Representative Compounds

Synthesis of N-[4-(aminomethyl)benzyl]-8-[1-(4-{[4-aminophenyl)acetyl]amino}butanoyl)-4-piperidinyl]-2-(1-naphthylmethyl)-1,3-dioxo-2,3,5,8-tetrahydo-1H-[1,2,4]triazolo[1,2-a]pyridazine-5-carboxamide (31):

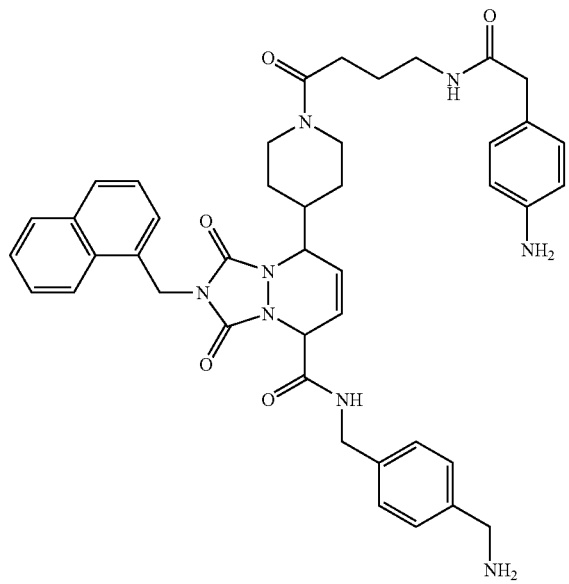
(31)

Resin bound 1,4-bis(aminomethyl)-benzene (500 mg, 0.35 mmol, 0.69 mmol/g loading) was coupled to the Fmoc-piperidine dienoic acid (3.0 equiv) in the presence of BOP (3 equiv), HOBT (3 equiv) in N,N-dimethylformamide (DMF, 8 mL) at room temperature for 4 h to give the corresponding polymer-bound Fmoc-diene. Kaiser test was negative. Deprotection of the Fmoc with 25% piperidine/DMF (positive chloranil), followed by coupling with Fmoc-4-aminobutyric acid (3 equiv), employing the above conditions and reagent equivalents, provided the intermediate Fmoc-butyric acid diene amide. Final Fmoc removal and subsequent coupling with 2-[4-[(tert-butoxycarbonyl)amino]phenyl]acetic acid (3 equiv) under the above conditions and reagent equivalents completed the chain length and set the stage for the penultimate Diels-Alder reaction step. Exposing this extended dienyl unit to 4-(1-Naphthylmethyl)-1,2,4-triazolidine-3,5-dione (3 equiv) in the presence of [bis(trifluoroacetoxy)iodo]benzene (3 equiv) for 3 h at room temperature efficiently yielded the resin-bound compound inhibitor. The desired product was cleaved from the resin in concert with the t-boc protecting group on treatment with 95% TFA/H$_2$O for 90 minutes. The supernatant was collected and combined with washes (2×1 mL 95% aq TFA). The residue obtained after evaporation of the solution was redissolved in TFA (250 µL) and triturated with Et$_2$O. After centrifugation (3000 rpm), the solid product was collected, dried and use as is in the following step. MS (ESI+) m/z 757.50 (M+H$^+$).

Synthesis of N-{4-[(acetoxyamino)methyl]benzyl}-8-{1-[4-({[4-(acetylamino)phenyl]acetyl}amino)butanoyl]-4-piperidinyl}-2-(1-naphthylmethyl)-1,3-dioxo-2,3,5,8-tetrahydo-1H-[1,2,4]triazolo[1,2-a]pyridazine-5-carboxamide (32)

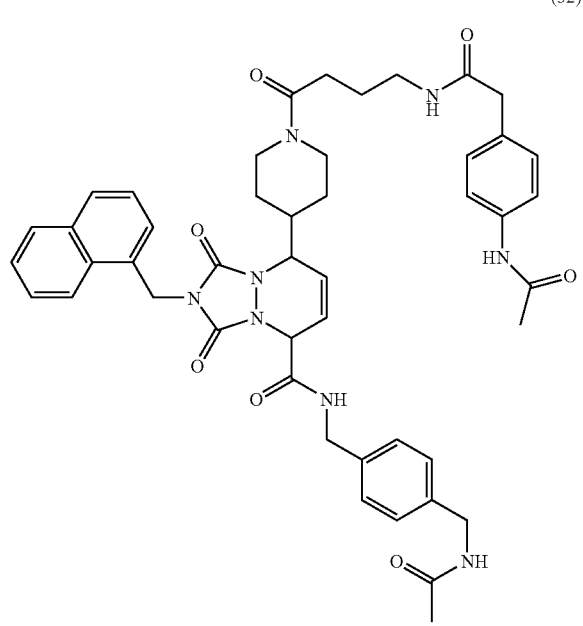

(32)

The crude adduct (31) was treated with a saturated solution of NaHCO$_3$ (5 mL) and stirred at room temperature for 20 minutes. The mixture was concentrated to dryness resulting in a white powder. The solid was re-suspended in dry methanol (10 mL), centrifuged at 3000 rpm, filtered and concentrated. The resulting oily residue was stirred with excess acetic anhydride in DCM for 12 h and concentrated. Purification by HPLC afforded the desired bis-acetylated compound (32) in a 1:1 isomeric ratio in quantitative yield. MS (ESI+) m/z 841.20 (M+H$^+$).

Synthesis of N-[4-(aminomethyl)benzyl]-8-[1-(4-{[4-aminophenyl)acetyl]amino}butanoyl)-4-piperidinyl]-2-(1-naphthylmethyl)-1,3-dioxohexahydro-1H-[1,2,4]triazolo[1,2-a]pyridazine-5-carboxamide (33)

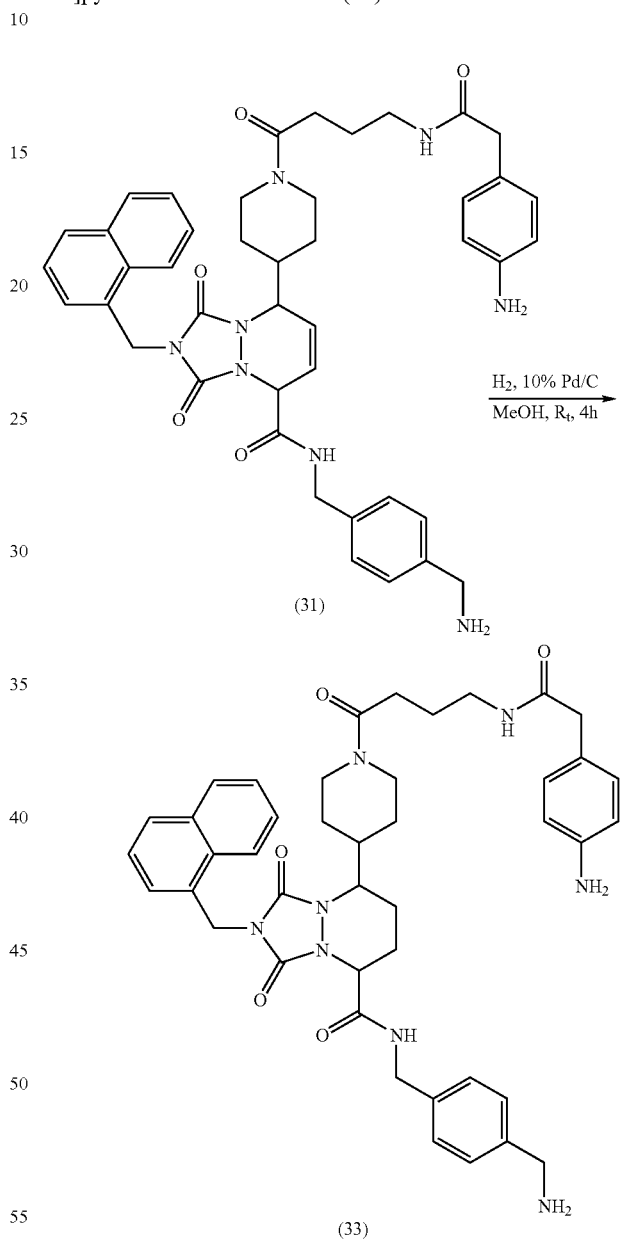

A solution of 31 (150 mg) in MeOH (5 mL) was subjected to catalytic hydrogenation with 10% Pd/C for 2 h. After removal of the catalyst by filtration, the solvent was evaporated and the desired product purified by HPLC (33). MS (ESI+) m/z 759.70 (M+H$^+$).

Synthesis of N-[4-(aminomethyl)benzyl]-8-[1-(4-{[4-aminophenyl)acetyl]amino}butanoyl)-4-piperidinyl]-2-(1-naphthylmethyl)-1,3-dioxo-2,3,7,8-tetrahydo-1H-[1,2,4]triazolo[1,2-a]pyridazine-5-carboxamide (34)

(34)

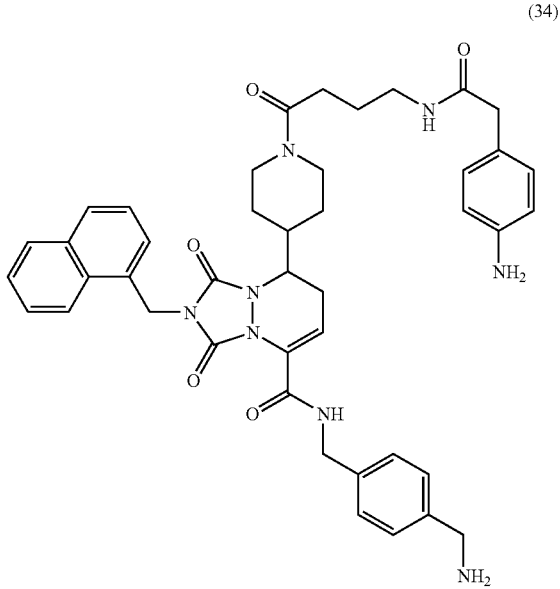

Resin bound 1,4-bis(aminomethyl)-benzene (200 mg, 0.14 mmol, 0.69 mmol/g loading) was coupled to the Fmoc-piperidine dienoic acid (3.0 equiv) in the presence of BOP (3 equiv), HOBT (3 equiv) in N,N-dimethylformamide (DMF, 8 mL) at room temperature for 4 h to give the corresponding polymer-bound Fmoc-diene. Kaiser test was negative. Deprotection of the Fmoc with 25% piperidine/DMF (positive chloranil), followed by coupling with Fmoc-4-aminobutyric acid (3 equiv), employing the above conditions and reagent equivalents, provided the intermediate Fmoc-butyric acid diene amide. Final Fmoc removal and subsequent coupling with 2-[4-[(tert-butoxycarbonyl)amino]phenyl]acetic acid (3 equiv) under the above conditions and reagent equivalents completed the chain length and set the stage for the Diels-Alder reaction step. Exposing this extended dienyl unit to 4-(1-Naphthylmethyl)-1,2,4-triazolidine-3,5-dione (3 equiv) in the presence of [bis(trifluoroacetoxy)iodo]benzene (3 equiv) for 3 h at room temperature efficiently yielded the resin-bound bicyclic compound. Following the Diels-Alder reaction, the resin-bound β-strand mimetic was treated with DBU (3 equiv) in DCM for 2 h at room temperature. The desired product was cleaved from the resin in concert with the t-boc protecting group on treatment with 95% TFA/$H_2O$ for 90 minutes. The supernatant was collected and combined with washes (2×1 mL 95% aq TFA). The residue obtained after evaporation of the solution was redissolved in TFA (250 μL) and triturated with $Et_2O$. After centrifugation (3000 rpm), the solid product was collected and dried (34). MS (ESI+) m/z 757.50 (M+H$^+$) and tR 12.78(B) min.

Example 5

TABLE 3

REPRESENTATIVE COMPOUNDS

| Cpd # | Z (point of attachment at X₁) | R₅ (point of attachment at X₃) | R₆ (point of attachment at X₅) | [M + H]⁺ | RT | Method |
|---|---|---|---|---|---|---|
| 1 | 1-naphthylmethyl (X₁-CH₂-naphthalene) | 4-aminophenylacetyl-NH-(CH₂)₃-C(=O)-X₃ | 4-(aminomethyl)benzyl-X₅ | 757.5 | 18.07(B) | A2 |
| 2 | 3-guanidinobenzyl | 4-(aminomethyl)benzoyl-NH-(CH₂)₃-C(=O)-X₃ | 4-(aminomethyl)benzyl-X₅ | 764.5 | 10.41(B) | A1 |

TABLE 3-continued

REPRESENTATIVE COMPOUNDS

| Cpd# | Z (point of attachment at $X_1$) | $R_5$ (point of attachment at $X_3$) | $R_6$ (point of attachment at $X_5$) | $[M+H]^+$ | RT | Method |
|---|---|---|---|---|---|---|
| 3 | naphthyl-CH2-$X_1$ | cyclohexyl with $X_3$-C(O)- and -CH2-NH-C(O)-CH2-C6H4-NH2 | 4-(aminomethyl)benzyl-$X_5$ (NH2) | 811.9 | 22.43(B) | A2 |
| 4 | naphthyl-CH2-$X_1$ | $X_3$-C(O)-(CH2)3-NH-C(O)-CH2-C6H4-NH2 | 4-(aminomethyl)benzyl-$X_5$ (NH2) | 757.5 | 12.47(B) | A1 |

TABLE 3-continued
REPRESENTATIVE COMPOUNDS
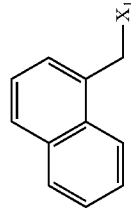
| Cpd# | Z (point of attachment at X₁) | R₅ (point of attachment at X₃) | R₆ (point of attachment at X₅) | [M + H]⁺ | RT | Method |
|---|---|---|---|---|---|---|
| 5 | 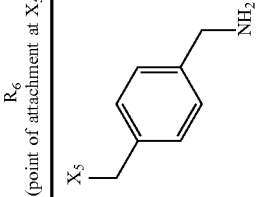 | 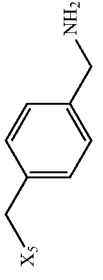 | 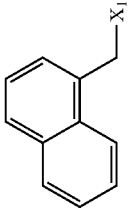 | 757.7 | 12.78(B) | A1 |
| 6 | 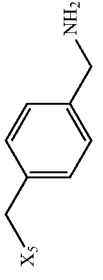 | 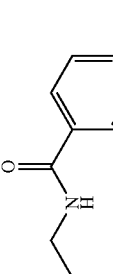 | | 757.9 | 6.54(B) | A2 |

TABLE 3-continued

REPRESENTATIVE COMPOUNDS

| Cpd# | Z (point of attachment at X₁) | R₅ (point of attachment at X₃) | R₆ (point of attachment at X₅) | [M + H]⁺ | RT | Method |
|---|---|---|---|---|---|---|
| 7 | 1-naphthylmethyl | benzamide-CH₂-C(O)-X₃ with 4-aminomethylphenyl | 4-aminomethylphenyl-CH₂-X₅ | 729.9 | 0.92(A) | A1 |
| 8 | 1-naphthylmethyl | benzamide-CH₂CH₂-C(O)-X₃ with 4-aminomethylphenyl | 4-aminomethylphenyl-CH₂-X₅ | 743.9 | 1.12(A) | A1 |
| 9 | 1-naphthylmethyl | 4-(aminomethyl)benzoyl-piperidine-4-C(O)-X₃ | 4-aminomethylphenyl-CH₂-X₅ | 783.5 | 19.74(B) | A2 |

TABLE 3-continued

REPRESENTATIVE COMPOUNDS

| Cpd # | Z (point of attachment at X₁) | R₅ (point of attachment at X₃) | R₆ (point of attachment at X₅) | [M + H]⁺ | RT | Method |
|---|---|---|---|---|---|---|
| 10 | 1-naphthylmethyl | 4-(aminomethyl)benzamide linked via cyclohexyl-CH₂-NH | 4-(aminomethyl)phenyl | 812.0 | 1.12(A) | A1 |
| 11 | 1-naphthylmethyl | 4-(aminomethyl)benzamide linked via phenyl-CH₂-NH | 4-(aminomethyl)phenyl | 806.0 | 1.12(A) | A1 |
| 12 | 1-naphthylmethyl | 2-(4-aminophenyl)acetamide linked via CH₂-C(O)-NH | 4-(aminomethyl)phenyl | 729.9 | 0.95(A) | A1 |

TABLE 3-continued

REPRESENTATIVE COMPOUNDS

| Cpd# | Z (point of attachment at X₁) | R₅ (point of attachment at X₃) | R₆ (point of attachment at X₅) | [M + H]⁺ | RT | Method |
|---|---|---|---|---|---|---|
| 13 | naphthylmethyl (X₁-CH₂-naphthalene) | X₃-C(O)-CH₂-C(O)-NH-CH₂-C₆H₄(4-NH₂) ... with 4-aminophenylacetamide linker | 4-(aminomethyl)benzyl (X₅-CH₂-C₆H₄-CH₂NH₂) | 743.9 | 0.95(A) | A1 |
| 14 | naphthylmethyl (X₁-CH₂-naphthalene) | X₃-C(O)-piperidin-4-yl-N-C(O)-CH₂-C₆H₄(4-NH₂) | 4-(aminomethyl)benzyl (X₅-CH₂-C₆H₄-CH₂NH₂) | 783.5 | 19.87(B) | A2 |

TABLE 3-continued

REPRESENTATIVE COMPOUNDS

| Cpd # | Z (point of attachment at X$_1$) | R$_5$ (point of attachment at X$_3$) | R$_6$ (point of attachment at X$_5$) | [M + H]$^+$ | RT | Method |
|---|---|---|---|---|---|---|
| 15 | naphthylmethyl | 4-(4-aminophenylacetamidomethyl)benzoyl | 4-(aminomethyl)benzyl | 806.0 | 1.38(A) | A1 |
| 16 | 3-guanidinobenzyl | 4-(aminomethyl)benzamido-propylcarbonyl | 4-(aminomethyl)benzyl | 736.9 | 0.59(A) | A1 |
| 17 | 3-guanidinobenzyl | 4-(aminomethyl)benzamido-ethylcarbonyl | 4-(aminomethyl)benzyl | 750.9 | 0.60(A) | A1 |

TABLE 3-continued

REPRESENTATIVE COMPOUNDS

| Cpd# | Z (point of attachment at X₁) | R₅ (point of attachment at X₃) | R₆ (point of attachment at X₅) | [M + H]⁺ | RT | Method |
|---|---|---|---|---|---|---|
| 18 | 3-aminomethyl-phenyl-guanidine | 4-(aminomethyl)cyclohexyl-carbonylamino-methyl-benzoyl | 4-(aminomethyl)benzyl | 819.0 | 0.92(A) | A1 |
| 19 | 3-aminomethyl-phenyl-guanidine | 4-(aminomethyl)phenyl-carbonylamino-methyl-benzoyl | 4-(aminomethyl)benzyl | 812.9 | 0.73(A) | A1 |
| 20 | 3-aminomethyl-phenyl-guanidine | 4-aminophenyl-acetylamino-acetyl | 4-(aminomethyl)benzyl | 736.9 | 0.67(A) | A1 |

TABLE 3-continued

REPRESENTATIVE COMPOUNDS

| Cpd# | Z (point of attachment at $X_1$) | $R_5$ (point of attachment at $X_3$) | $R_6$ (point of attachment at $X_5$) | [M + H]$^+$ | RT | Method |
|---|---|---|---|---|---|---|
| 21 | 3-guanidinobenzyl | | | 750.9 | 0.69(A) | A1 |
| 22 | 3-guanidinobenzyl | | | 764.9 | 0.62(A) | A1 |
| 23 | 3-guanidinobenzyl | | | 819.0 | 0.80(A) | A1 |

TABLE 3-continued

REPRESENTATIVE COMPOUNDS

| Cpd # | Z (point of attachment at X₁) | R₅ (point of attachment at X₃) | R₆ (point of attachment at X₅) | [M + H]⁺ | RT | Method |
|---|---|---|---|---|---|---|
| 24 | 3-guanidino-benzyl (X₁) | 4-[(4-aminobenzyl)carbamoyl]benzoyl (X₃) | 4-(aminomethyl)benzyl (X₅) | 812.9 | 0.96(A) | A1 |
| 25 | H₃C—X₁ | 4-(4-aminophenyl)acetamido-butanoyl (X₃) | 4-(aminomethyl)benzyl (X₅) | 631.0 | 1.17(A) | A1 |

TABLE 3-continued

REPRESENTATIVE COMPOUNDS

| Cpd# | Z (point of attachment at $X_1$) | $R_5$ (point of attachment at $X_3$) | $R_6$ (point of attachment at $X_5$) | $[M+H]^+$ | RT | Method |
|---|---|---|---|---|---|---|
| 26 | phenyl-$X_1$ | 4-aminophenyl-CH$_2$-C(O)-NH-(CH$_2$)$_3$-C(O)-$X_3$ | 1,4-phenylene-bis(CH$_2$) with $X_5$ and NH$_2$ | 693.0 | 0.87(A) | A1 |
| 27 | benzyl-$X_1$ | 4-aminophenyl-CH$_2$-C(O)-NH-(CH$_2$)$_3$-C(O)-$X_3$ | 1,4-phenylene-bis(CH$_2$) with $X_5$ and NH$_2$ | 707.6 | 8.60(B) | A2 |
| 28 | 3-bromobenzyl-$X_1$ | 4-aminophenyl-CH$_2$-C(O)-NH-(CH$_2$)$_3$-C(O)-$X_3$ | 1,4-phenylene-bis(CH$_2$) with $X_5$ and NH$_2$ | 786.7 | 0.88(A) | A1 |

TABLE 3-continued
REPRESENTATIVE COMPOUNDS
| Cpd# | Z (point of attachment at X₁) | R₅ (point of attachment at X₃) | R₆ (point of attachment at X₅) | [M + H]⁺ | RT | Method |
|---|---|---|---|---|---|---|
| 29 | 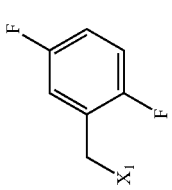 |  | 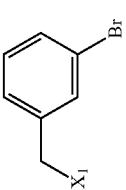 | 814.8 | 0.93(A) | A1 |
| 30 | 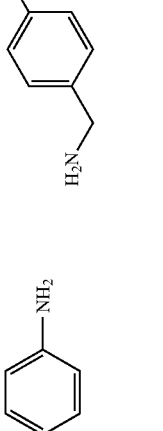 | 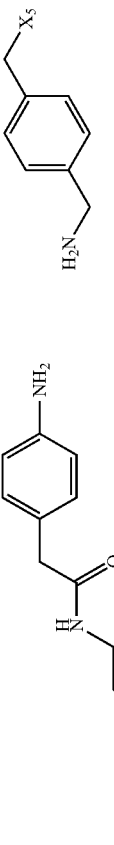 | | 771.9 | 1.10(A) | A1 |

TABLE 3-continued
REPRESENTATIVE COMPOUNDS
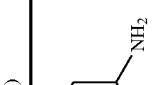
| Cpd# | Z (point of attachment at $X_1$) | $R_5$ (point of attachment at $X_3$) | $R_6$ (point of attachment at $X_5$) | [M + H]$^+$ | RT | Method |
|---|---|---|---|---|---|---|
| 31 |  | 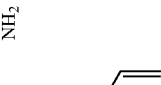 | 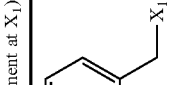 | 700.4 | 1.22(A) | A2 |
| 32 | 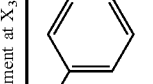 |  |  | 757.4 | 1.14(A) | A2 |

TABLE 3-continued
REPRESENTATIVE COMPOUNDS
| Cpd# | Z (point of attachment at X₁) | R₅ (point of attachment at X₃) | R₆ (point of attachment at X₅) | [M + H]⁺ | RT | Method |
|---|---|---|---|---|---|---|
| 33 | 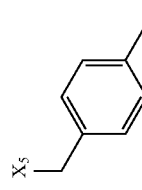 | 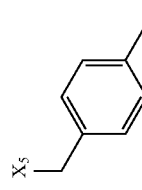 | 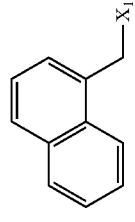 | 771.4 | 1.16(A) | A2 |
| 34 | 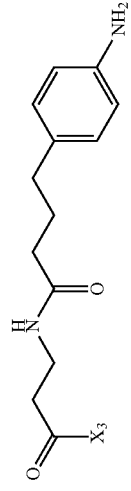 | 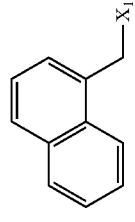 | 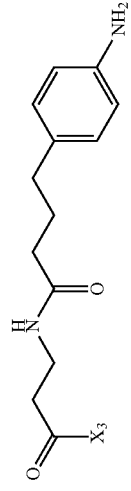 | 785.4 | 1.14(A) | A2 |

TABLE 3-continued
REPRESENTATIVE COMPOUNDS
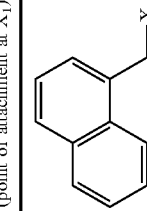
| Cpd# | Z (point of attachment at $X_1$) | $R_5$ (point of attachment at $X_3$) | $R_6$ (point of attachment at $X_5$) | $[M + H]^+$ | RT | Method |
|---|---|---|---|---|---|---|
| 35 |  | 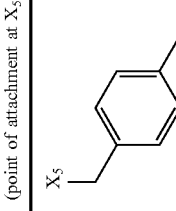 | 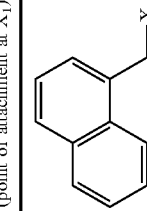 | 799.4 | 1.40(A) | A2 |
| 36 | 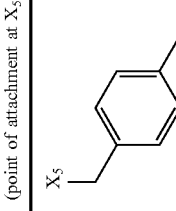 |  | | 813.4 | 1.38(A) | A2 |

TABLE 3-continued
REPRESENTATIVE COMPOUNDS
| Cpd# | Z (point of attachment at X₁) | R₅ (point of attachment at X₃) | R₆ (point of attachment at X₅) | [M + H]⁺ | RT | Method |
|---|---|---|---|---|---|---|
| 37 | 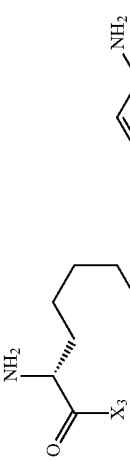 | 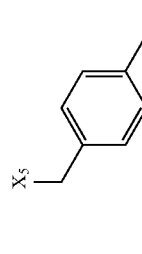 | 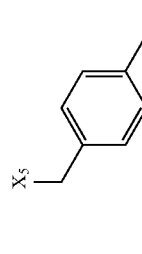 | 823.4 | 1.19(A) | A2 |
| 38 | 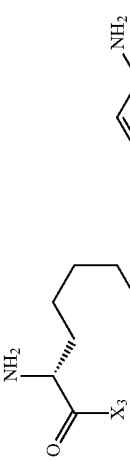 | 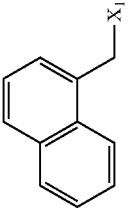 | 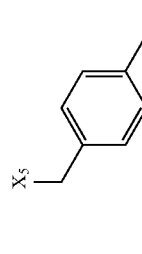 | 828.5 | 0.96(A) | A2 |

TABLE 3-continued

REPRESENTATIVE COMPOUNDS

| Cpd# | Z (point of attachment at X₁) | R₅ (point of attachment at X₃) | R₆ (point of attachment at X₅) | [M + H]⁺ | RT | Method |
|---|---|---|---|---|---|---|
| 39 | naphthalenylmethyl | 4-aminophenylacetamido-CH₂-C(O)-X₃ | 4-(amidino)benzyl-X₅ | 742.8 | 1.10(A) | A2 |
| 40 | naphthalenylmethyl | 4-aminophenylacetamido-(CH₂)₂-C(O)-X₃ | 4-(amidino)benzyl-X₅ | 756.3 | 1.10(A) | A2 |

TABLE 3-continued
REPRESENTATIVE COMPOUNDS
| Cpd# | Z (point of attachment at $X_1$) | $R_5$ (point of attachment at $X_3$) | $R_6$ (point of attachment at $X_5$) | [M + H]$^+$ | RT | Method |
|---|---|---|---|---|---|---|
| 41 | 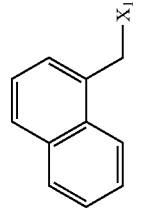 | 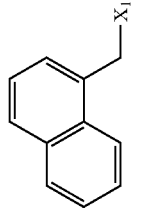 | 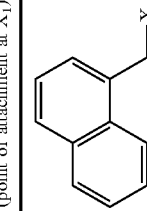 | 713.3 | 1.10(A) | A2 |
| 42 | 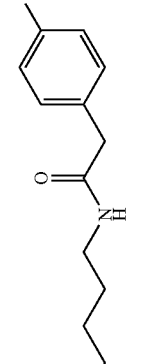 | 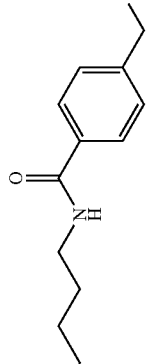 | 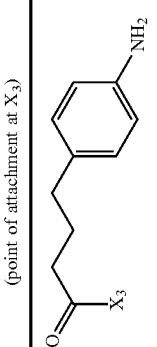 | 771.9 | 0.92(A) | A1 |
| 43 | 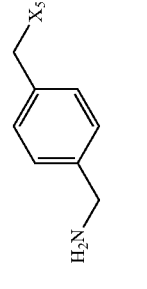 | 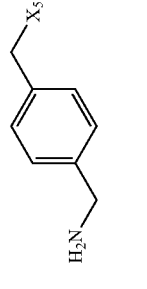 | 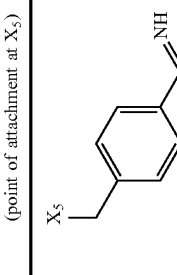 | 771.9 | 0.95(A) | A1 |

TABLE 3-continued

REPRESENTATIVE COMPOUNDS

| Cpd# | Z (point of attachment at $X_1$) | $R_5$ (point of attachment at $X_3$) | $R_6$ (point of attachment at $X_5$) | $[M+H]^+$ | RT | Method |
|---|---|---|---|---|---|---|
| 44 | 1-naphthylmethyl | 4-(aminomethyl)benzamide-hexanoyl | 4-(aminomethyl)benzyl | 785.0 | 0.92(A) | A1 |
| 45 | 1-naphthylmethyl | 4-aminophenylacetamide-hexanoyl | 4-(aminomethyl)benzyl | 786.0 | 1.80(A) | A1 |
| 46 | 1-naphthylmethyl | lysine-4-(aminomethyl)benzamide | 4-(aminomethyl)benzyl | 801.0 | 0.78(A) | A1 |

TABLE 3-continued

REPRESENTATIVE COMPOUNDS

| Cpd# | Z (point of attachment at X₁) | R₅ (point of attachment at X₃) | R₆ (point of attachment at X₅) | [M + H]⁺ | RT | Method |
|---|---|---|---|---|---|---|
| 47 | 1-naphthylmethyl | lysine-derived with 4-aminophenylacetamide | 4-(aminomethyl)benzyl | 801.0 | .82(A) | A1 |
| 48 | 1-naphthylmethyl | lysine with 4-(aminomethyl)benzamide | 4-(aminomethyl)benzyl | 786.9 | .77(A) | A1 |
| 49 | 1-naphthylmethyl | lysine with 4-(aminomethyl)phenylacetamide | 4-(aminomethyl)benzyl | 786.9 | 0.92(A) | A1 |

TABLE 3-continued

REPRESENTATIVE COMPOUNDS

| Cpd# | Z (point of attachment at $X_1$) | $R_5$ (point of attachment at $X_3$) | $R_6$ (point of attachment at $X_5$) | $[M+H]^+$ | RT | Method |
|---|---|---|---|---|---|---|
| 50 | naphthalen-1-ylmethyl | 2-amino-6-(4-(aminomethyl)benzamido)hexanoyl | 4-(aminomethyl)benzyl | 786.9 | 0.84(A) | A1 |
| 51 | naphthalen-1-ylmethyl | 2-amino-6-(2-(4-aminophenyl)acetamido)hexanoyl | 4-(aminomethyl)benzyl | 786.9 | 0.81(A) | A1 |

TABLE 3-continued

REPRESENTATIVE COMPOUNDS

| Cpd# | Z (point of attachment at $X_1$) | $R_5$ (point of attachment at $X_3$) | $R_6$ (point of attachment at $X_5$) | $[M + H]^+$ | RT | Method |
|---|---|---|---|---|---|---|
| 52 | 1-naphthylmethyl | | | 781.9 | 0.93(A) | A1 |
| 53 | 1-naphthylmethyl | | | 781.9 | 0.97(A) | A1 |
| 54 | 1-naphthylmethyl | | | 822.0 | 0.96(A) | A1 |

TABLE 3-continued
REPRESENTATIVE COMPOUNDS
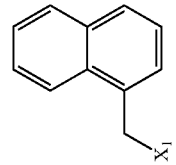
| Cpd# | Z (point of attachment at X₁) | R₅ (point of attachment at X₃) | R₆ (point of attachment at X₅) | [M + H]⁺ | RT | Method |
|---|---|---|---|---|---|---|
| 55 | 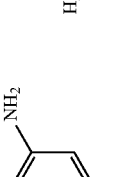 | 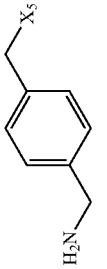 | 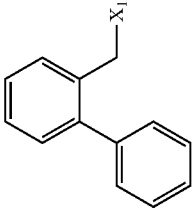 | 822.0 | 1.00(A) | A1 |
| 56 | 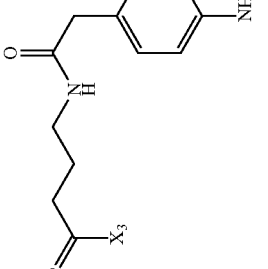 | 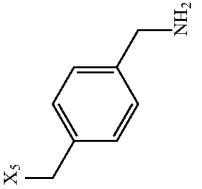 | | 783.7 | 18.00(B) | A2 |

TABLE 3-continued

REPRESENTATIVE COMPOUNDS

| Cpd# | Z (point of attachment at $X_1$) | $R_5$ (point of attachment at $X_3$) | $R_6$ (point of attachment at $X_5$) | [M + H]$^+$ | RT | Method |
|---|---|---|---|---|---|---|
| 57 | 3-guanidino-benzyl | 4-aminophenylacetamido-butanoyl | 4-(aminomethyl)benzyl | 764.7 | 6.57(B) | A2 |
| 58 | 3-guanidino-benzyl | succinyl (HOOC-CH$_2$CH$_2$-C(O)-) | | 659.6 | 12.48(B) | A2 |

TABLE 3-continued

REPRESENTATIVE COMPOUNDS

| Cpd # | Z (point of attachment at $X_1$) | $R_5$ (point of attachment at $X_3$) | $R_6$ (point of attachment at $X_5$) | [M + H]$^+$ | RT | Method |
|---|---|---|---|---|---|---|
| 59 | phenylsulfonyl-ethyl-$X_1$ | 4-aminophenylacetamido-butanoyl-$X_3$ | 4-(aminomethyl)benzyl-$X_5$ | 785.8 | 7.50(B) | A2 |
| 60 | phenylsulfonyl-ethyl-$X_1$ | 4-aminophenylacetamido-butanoyl-$X_3$ | 4-amidinobenzyl-$X_5$ | 798.8 | 7.63(B) | A2 |

TABLE 3-continued
REPRESENTATIVE COMPOUNDS
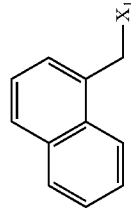
| Cpd# | Z (point of attachment at $X_1$) | $R_5$ (point of attachment at $X_3$) | $R_6$ (point of attachment at $X_5$) | $[M + H]^+$ | RT | Method |
|---|---|---|---|---|---|---|
| 61 | 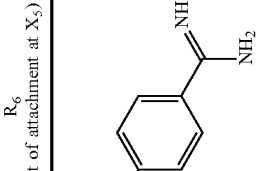 | 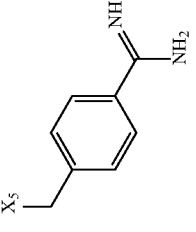 | 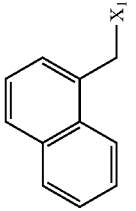 | 770.8 | 18.48(B) | A2 |
| 62 | 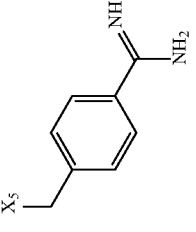 | 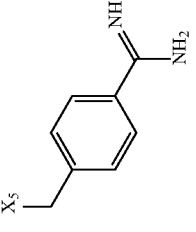 | | 784.9 | 15.5(B) | A2 |

TABLE 3-continued
REPRESENTATIVE COMPOUNDS
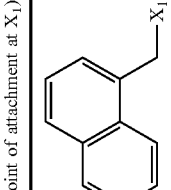
| Cpd# | Z (point of attachment at X₁) | R₅ (point of attachment at X₃) | R₆ (point of attachment at X₅) | [M + H]⁺ | RT | Method |
|---|---|---|---|---|---|---|
| 63 | 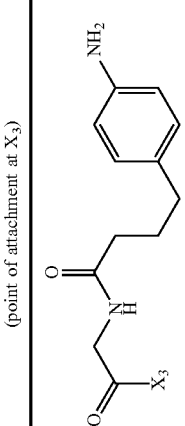 | 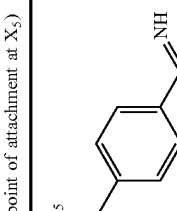 | 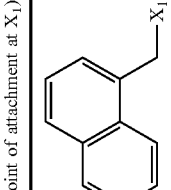 | 770.9 | 19.27(B) | A2 |
| 64 | 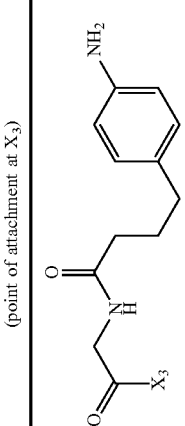 | 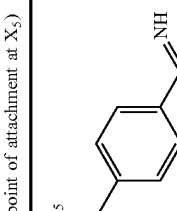 | | 777.9 | 11.16(B) | A2 |

TABLE 3-continued
REPRESENTATIVE COMPOUNDS
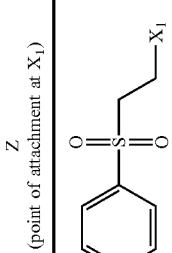
| Cpd# | Z (point of attachment at X₁) | R₅ (point of attachment at X₃) | R₆ (point of attachment at X₅) | [M + H]⁺ | RT | Method |
|---|---|---|---|---|---|---|
| 65 | 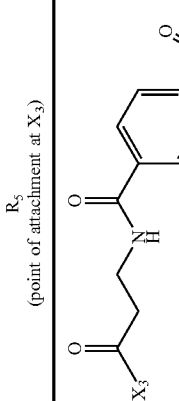 | 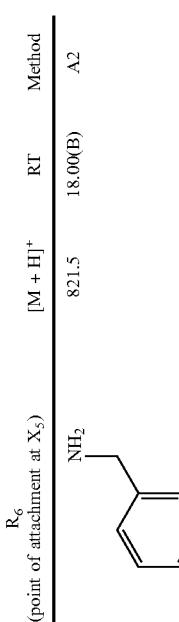 | 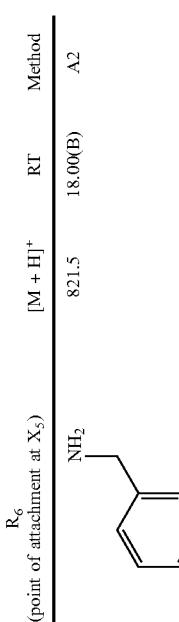 | 821.5 | 18.00(B) | A2 |
| 66 | 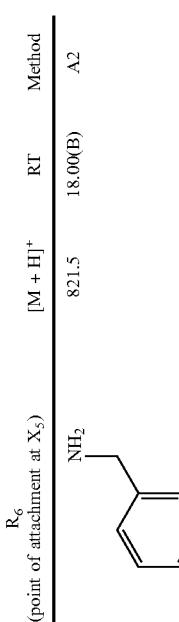 | 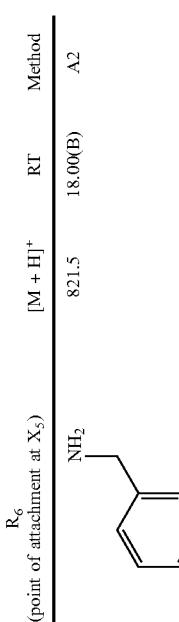 | 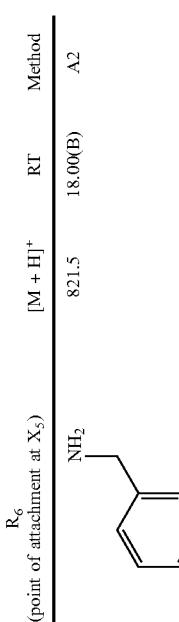 | 693.8 | 1.25(A) | A2 |

TABLE 3-continued

REPRESENTATIVE COMPOUNDS

| Cpd# | Z (point of attachment at $X_1$) | $R_5$ (point of attachment at $X_3$) | $R_6$ (point of attachment at $X_5$) | $[M + H]^+$ | RT | Method |
|---|---|---|---|---|---|---|
| 67 | 5-methyl-pyrazinyl-CH2-X1 | 4-hydroxyphenyl-CH2-C(O)NH-(CH2)3-C(O)-X3 | 4-(aminomethyl)benzyl-X5 | 724.5 | 7.00(B) | A2 |
| 68 | X1-CH2-pyrazinyl-CH3 | 4-(aminomethyl)phenyl-C(O)NH-(CH2)3-C(O)-X3 | 4-(aminomethyl)benzyl-X5 | 723.9 | 1.38(A) | A2 |

TABLE 3-continued

REPRESENTATIVE COMPOUNDS

| Cpd # | Z (point of attachment at $X_1$) | $R_5$ (point of attachment at $X_3$) | $R_6$ (point of attachment at $X_5$) | $[M+H]^+$ | RT | Method |
|---|---|---|---|---|---|---|
| 69 | PhSO$_2$CH$_2$CH$_2$-$X_1$ | 4-HO-C$_6$H$_4$-CH$_2$-C(O)-NH-(CH$_2$)$_3$-C(O)-$X_3$ | 4-(H$_2$N-CH$_2$)-C$_6$H$_4$-CH$_2$-$X_5$ | 786.5 | 21.61(B) | A2 |
| 70 | PhSO$_2$CH$_2$CH$_2$-$X_1$ | 4-(H$_2$NSO$_2$)-C$_6$H$_4$-C(O)-NH-(CH$_2$)$_3$-C(O)-$X_3$ | 4-(H$_2$N-CH$_2$)-C$_6$H$_4$-CH$_2$-$X_5$ | 836.0 | 1.25(A) | A2 |

TABLE 3-continued
REPRESENTATIVE COMPOUNDS
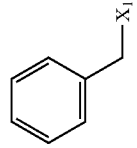
| Cpd# | Z (point of attachment at $X_1$) | $R_5$ (point of attachment at $X_3$) | $R_6$ (point of attachment at $X_5$) | [M + H]$^+$ | RT | Method |
|---|---|---|---|---|---|---|
| 71 | 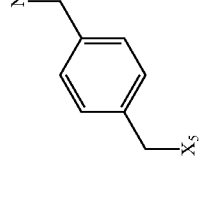 | 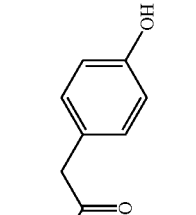 | 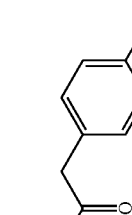 | 708.8 | 1.03(A) | A2 |
| 72 | 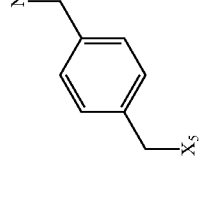 | 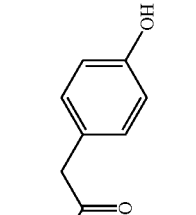 | | 707.8 | 1.25(A) | A2 |

TABLE 3-continued

REPRESENTATIVE COMPOUNDS

| Cpd# | Z (point of attachment at X₁) | R₅ (point of attachment at X₃) | R₆ (point of attachment at X₅) | [M + H]⁺ | RT | Method |
|---|---|---|---|---|---|---|
| 73 | 1-naphthylmethyl | 4-hydroxyphenylacetamido-propyl-C(O)-X₃ | 4-aminomethylbenzyl-X₅ | 758.9 | 1.13(A) | A2 |
| 74 | 6-methylpyrazin-2-ylmethyl | 4-hydroxyphenylacetamido-butyl-C(O)-X₃ | 4-aminomethylbenzyl-X₅ | 738.6 | 33.00(B) | A2 |

TABLE 3-continued

REPRESENTATIVE COMPOUNDS

| Cpd# | Z (point of attachment at $X_1$) | $R_5$ (point of attachment at $X_3$) | $R_6$ (point of attachment at $X_5$) | $[M + H]^+$ | RT | Method |
|---|---|---|---|---|---|---|
| 75 | 5-(methyl)-2-methylpyridine with $X_1$ | 4-(aminomethyl)benzamide linker with $X_3$ | 4-(aminomethyl)benzyl with $X_5$ | 737.9 | 12.2(B) | A2 |
| 76 | phenylsulfonylethyl with $X_1$ | 4-hydroxyphenylacetamide linker with $X_3$ | 4-hydroxybenzyl with $X_5$ | 800.6 | 10.00(B) | A2 |

TABLE 3-continued

REPRESENTATIVE COMPOUNDS

| Cpd# | Z (point of attachment at X₁) | R₅ (point of attachment at X₃) | R₆ (point of attachment at X₅) | [M + H]⁺ | RT | Method |
|---|---|---|---|---|---|---|
| 77 | phenylsulfonylethyl-X₁ | 4-sulfamoylbenzamido-pentanoyl-X₃ | 4-(aminomethyl)benzyl-X₅ | 850.0 | 1.00(A) | A2 |
| 78 | benzyl-X₁ | 4-hydroxyphenylacetamido-pentanoyl-X₃ | 4-(aminomethyl)benzyl-X₅ | 722.9 | 1.07(A) | A2 |

TABLE 3-continued

REPRESENTATIVE COMPOUNDS

| Cpd# | Z (point of attachment at X₁) | R₅ (point of attachment at X₃) | R₆ (point of attachment at X₅) | [M + H]⁺ | RT | Method |
|---|---|---|---|---|---|---|
| 79 | benzyl | 4-(aminomethyl)benzamido-pentanoyl | 4-(aminomethyl)benzyl | 721.9 | 8.01(B) | A2 |
| 80 | 1-naphthylmethyl | 4-hydroxyphenylacetamido-pentanoyl | 4-(aminomethyl)benzyl | 772.9 | 1.45(A) | A2 |
| 81 | 1-naphthylmethyl | 4-acetamidophenylacetamido-butanoyl | 4-(acetamidomethyl)benzyl | 841.4 | 32.00(B) | A2 |

TABLE 3-continued
REPRESENTATIVE COMPOUNDS
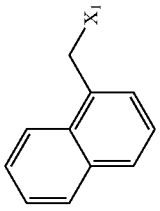
| Cpd# | Z (point of attachment at X₁) | R₅ (point of attachment at X₃) | R₆ (point of attachment at X₅) | [M + H]⁺ | RT | Method |
|---|---|---|---|---|---|---|
| 82 | 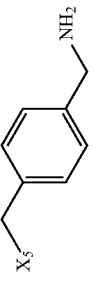 | 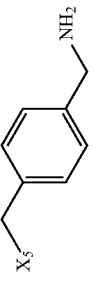 |  | 757.4 | 5.80(B) | A2 |
| 83 | 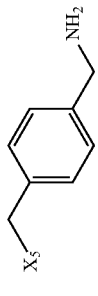 | 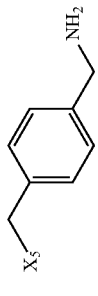 |  | 707.3 | 12.19(B) | A2 |

TABLE 3-continued
REPRESENTATIVE COMPOUNDS
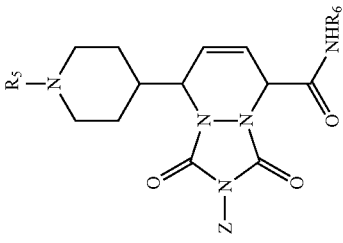
| Cpd # | Z (point of attachment at X₁) | R₅ (point of attachment at X₃) | R₆ (point of attachment at X₅) | [M + H]⁺ | RT | Method |
|---|---|---|---|---|---|---|
| 84 | 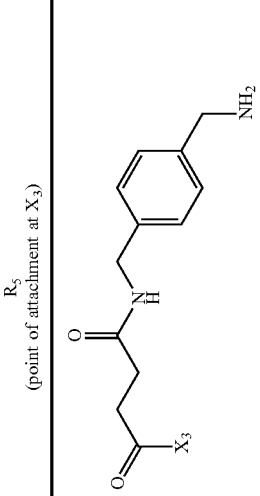 | 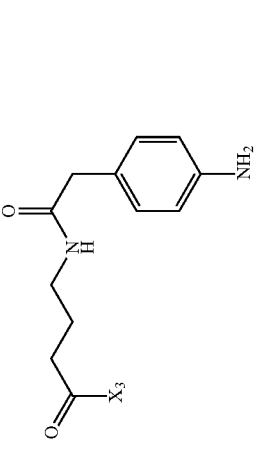 | 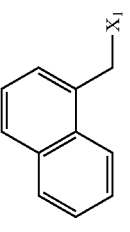 | 764.4 | 17.44(B) | A2 |
| 85 | 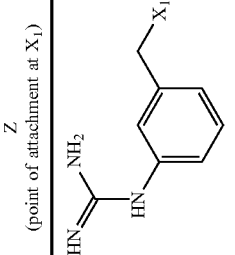 | 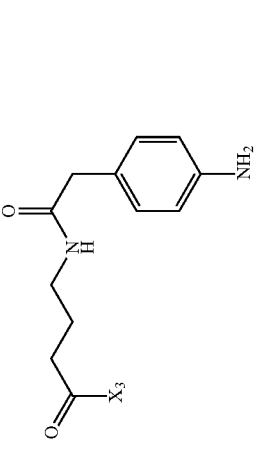 | | 759.4 | 17.77(B) | A2 |

TABLE 3-continued

REPRESENTATIVE COMPOUNDS

| Cpd# | Z (point of attachment at X₁) | R₅ (point of attachment at X₃) | R₆ (point of attachment at X₅) | [M + H]⁺ | RT | Method |
|---|---|---|---|---|---|---|
| 86 | 3-aminomethylphenyl guanidine | piperidine-benzamide | 4-aminomethylphenyl | 790.2 | 24.82(B) | A1 |
| 87 | 3-aminomethylphenyl guanidine | piperidine-phenylacetyl | 4-aminomethylphenyl | 790.2 | 16.13(B) | C |

Example 6

TABLE 4

REPRESENTATIVE COMPOUNDS

| Cpd# | Z (point of attachment at X₁) | R₆ (point of attachment at X₅) | [M + H]⁺ | RT | Method |
|---|---|---|---|---|---|
| 88 | | | 617.3 | 0.68(A) | E |
| 89 | | | 630.2 | 0.65(A) | E |
| 90 | | | 510.3 | 1.56(A) | C |
| 91 | | | 675.3 | 1.04(A) | C |
| 92 | | | 680.1 | 10.01(B) | C |

TABLE 4-continued

REPRESENTATIVE COMPOUNDS

| Cpd# | Z (point of attachment at $X_1$) | $R_6$ (point of attachment at $X_5$) | [M + H]$^+$ | RT | Method |
|---|---|---|---|---|---|
| 93 | 2,4-dinitrophenyl-SO$_2$-NH-(3-methylene)phenyl- | 4-(aminomethyl)benzyl- | 734.1 | 9.00(B) | C |
| 94 | 4-cyanophenyl-SO$_2$-NH-(3-methylene)phenyl- | 4-(aminomethyl)benzyl- | 669.3 | 0.92(A) | C |
| 95 | 4-methylphenyl-SO$_2$-NH-(3-methylene)phenyl- | 4-(aminomethyl)benzyl- | 658.3 | 0.85(A) | C |
| 96 | 4-methoxyphenyl-SO$_2$-NH-(3-methylene)phenyl- | 4-(aminomethyl)benzyl- | 674.3 | 0.88(A) | C |
| 97 | 4-aminophenyl-CH$_2$-C(O)-NH-(3-methylene)phenyl- | trans-4-(aminomethyl)cyclohexylmethyl- | 643.3 | 0.56(A) | B |
| 98 | 4-(aminomethyl)phenyl-C(O)-NH-(3-methylene)phenyl- | trans-4-(aminomethyl)cyclohexylmethyl- | 643.3 | 0.55(A) | B |

TABLE 4-continued
REPRESENTATIVE COMPOUNDS
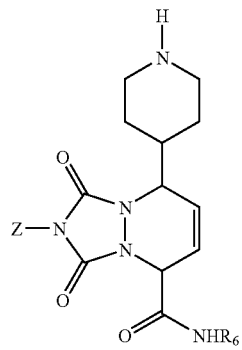
| Cpd# | Z (point of attachment at $X_1$) | $R_6$ (point of attachment at $X_5$) | $[M + H]^+$ | RT | Method |
|---|---|---|---|---|---|
| 99 | | | 775.4 | 9.50(B) | B |
| 100 | | | 639.2 | 11.9(B) | B |
| 101 | | | 696.2 | 0.92(A) | B |
| 102 | | | 696.7 | 0.91(A) | B |
| 103 | | | 682.2 | 9.95(B) | B |

TABLE 4-continued

REPRESENTATIVE COMPOUNDS

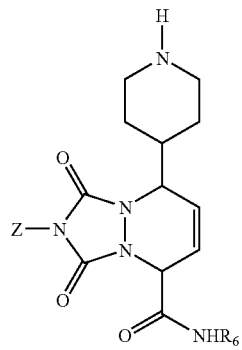

| Cpd# | Z (point of attachment at $X_1$) | $R_6$ (point of attachment at $X_5$) | $[M + H]^+$ | RT | Method |
|---|---|---|---|---|---|
| 104 | 3-fluorophenylacetamide-N-(3-methylphenyl) at $X_1$ | 4-(aminomethyl)cyclohexylmethyl at $X_5$ | 646.2 | 0.81(A) | B |
| 105 | 2-fluoro-5-nitrobenzamide-N-(3-methylphenyl) at $X_1$ | 4-(aminomethyl)cyclohexylmethyl at $X_5$ | 677.2 | 9.75(B) | B |
| 106 | 2-(pyrimidin-2-ylthio)acetamide-N-(3-methylphenyl) at $X_1$ | 4-(aminomethyl)cyclohexylmethyl at $X_5$ | 662.2 | 25.95(B) | B |
| 107 | 4-iodo-N-(3-methylphenyl)benzenesulfonamide at $X_1$ | 4-(aminomethyl)benzyl at $X_5$ | 770.1 | 8.83(B) | C |
| 108 | 4-(aminomethyl)-N-(3-methylphenyl)benzamide at $X_1$ | 4-(aminomethyl)benzyl at $X_5$ | 637.2 | 13.62(B) | B |
| 109 | 3-aminobenzyl at $X_1$ | 4-(aminomethyl)benzyl at $X_5$ | 504.2 | 1.52(B) | A2 |

TABLE 4-continued

REPRESENTATIVE COMPOUNDS

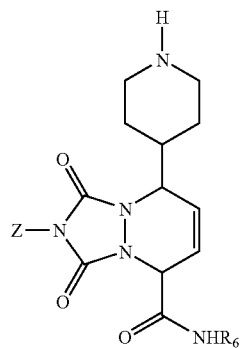

| Cpd# | Z (point of attachment at $X_1$) | $R_6$ (point of attachment at $X_5$) | $[M + H]^+$ | RT | Method |
|---|---|---|---|---|---|
| 110 | 4-aminophenyl-(CH$_2$)$_4$-$X_1$ | 4-(aminomethyl)benzyl-$X_5$ | 546.6 | 16.09(B) | A2 |
| 111 | 2-thienyl-CH$_2$-NH-C(O)-CH$_2$CH$_2$-$X_1$ | $X_5$-CH$_2$-cyclohexyl-CH$_2$NH$_2$ | 572.3 | 1.04(A) | D |
| 112 | 4-(H$_2$NO-)phenyl-CH$_2$CH$_2$-NH-C(O)-CH$_2$CH$_2$-$X_1$ | $X_5$-CH$_2$-cyclohexyl-CH$_2$NH$_2$ | 610.4 | 0.74(A) | D |
| 113 | 4-chlorobenzyl-NH-C(O)-CH$_2$CH$_2$-$X_1$ | $X_5$-CH$_2$-cyclohexyl-CH$_2$NH$_2$ | 600.3 | 0.82(A) | D |
| 114 | 4-(H$_2$NO-)benzyl-NH-C(O)-(CH$_2$)$_3$-$X_1$ | $X_5$-CH$_2$-cyclohexyl-CH$_2$NH$_2$ | 610.4 | 0.89(A) | D |
| 115 | 3,4-dimethoxyphenyl-CH$_2$CH$_2$-NH-C(O)-(CH$_2$)$_3$-$X_1$ | $X_5$-CH$_2$-cyclohexyl-CH$_2$NH$_2$ | 654.4 | 0.78(A) | D |

TABLE 4-continued

REPRESENTATIVE COMPOUNDS

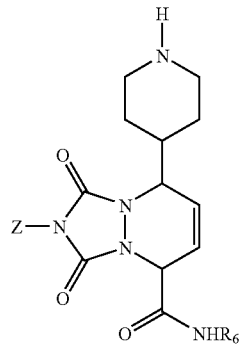

| Cpd# | Z (point of attachment at $X_1$) | $R_6$ (point of attachment at $X_5$) | $[M + H]^+$ | RT | Method |
|---|---|---|---|---|---|
| 116 | H₂N–C₆H₄–CH₂–NH–C(O)–(CH₂)₃–$X_1$ | $X_5$–cyclohexyl–CH₂–NH₂ | 595.4 | 0.14(A) | D |
| 117 | Ph–NH–CH₂CH₂–NH–C(O)–(CH₂)₃–$X_1$ | $X_5$–cyclohexyl–CH₂–NH₂ | 609.4 | 1.14(A) | D |
| 118 | 3,4-F₂–C₆H₃–CH₂–NH–C(O)–(CH₂)₄–$X_1$ | $X_5$–cyclohexyl–CH₂–NH₂ | 630.4 | 0.93(A) | D |
| 119 | H₂N–C(=NH)–C₆H₄–CH₂–NH–C(O)–(CH₂)₄–$X_1$ | $X_5$–cyclohexyl–CH₂–NH₂ | 636.4 | 0.14(A) | D |
| 120 | 2-thienyl–CH₂–NH–C(O)–(CH₂)₄–$X_1$ | $X_5$–cyclohexyl–CH₂–NH₂ | 600.3 | 0.78(A) | D |

TABLE 4-continued
REPRESENTATIVE COMPOUNDS
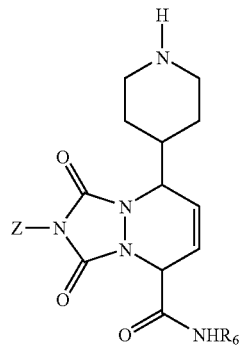
| Cpd# | Z (point of attachment at $X_1$) | $R_6$ (point of attachment at $X_5$) | $[M + H]^+$ | RT | Method |
|---|---|---|---|---|---|
| 121 | phenyl-NH-CH2CH2-NH-C(O)-(CH2)3-$X_1$ | $X_5$-CH2-cyclohexyl-CH2-NH2 | 623.4 | 0.68(A) | D |
| 122 | H2N-C(=NH)-N(piperidinyl)-CH2-NH-C(O)-CH2-$X_1$ | $X_5$-CH2-C6H4-CH2-NH2 | 609.4 | 0.19(A) | D |
| 123 | H2N-C(=NH)-C6H4-CH2-NH-C(O)-CH2-$X_1$ | $X_5$-CH2-C6H4-CH2-NH2 | 602.3 | 0.18(A) | D |
| 124 | H2N-C6H4-CH2-NH-C(O)-CH2-$X_1$ | $X_5$-CH2-C6H4-CH2-NH2 | 575.3 | 1.08(A) | D |
| 125 | HN-piperidinyl-CH2-NH-C(O)-CH2-$X_1$ | $X_5$-CH2-C6H4-CH2-NH2 | 567.3 | 1.29(A) | D |

TABLE 4-continued

REPRESENTATIVE COMPOUNDS

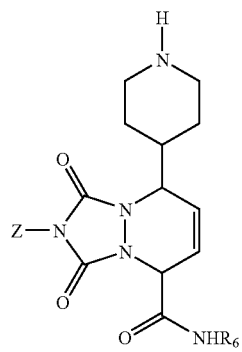

| Cpd# | Z (point of attachment at $X_1$) | $R_6$ (point of attachment at $X_5$) | $[M + H]^+$ | RT | Method |
|---|---|---|---|---|---|
| 126 | PhNH-CH2CH2-NH-C(O)-CH2CH2-$X_1$ | $X_5$-CH2-C6H4-CH2NH2 | 589.3 | 0.92(A) | D |
| 127 | 3-(H2NCH2)-C6H4-CH2-NH-C(O)-CH2CH2-$X_1$ | $X_5$-CH2-C6H4-CH2NH2 | 589.3 | 0.14(A) | D |
| 128 | 3-(H2N)-C6H4-CH2-NH-C(O)-CH2CH2-$X_1$ | $X_5$-CH2-C6H4-CH2NH2 | 575.3 | 1.89(A) | D |
| 129 | 4-(H2N)-C6H4-CH2-NH-C(O)-CH2CH2CH2-$X_1$ | $X_5$-CH2-C6H4-CH2NH2 | 589.3 | 1.06(A) | D |
| 130 | piperidin-4-yl-CH2-NH-C(O)-CH2CH2CH2-$X_1$ | $X_5$-CH2-C6H4-CH2NH2 | 581.4 | 0.14(A) | D |
| 131 | 3-(H2N)-C6H4-CH2-NH-C(O)-CH2CH2CH2-$X_1$ | $X_5$-CH2-C6H4-CH2NH2 | 589.3 | 0.14(A) | D |

TABLE 4-continued

REPRESENTATIVE COMPOUNDS

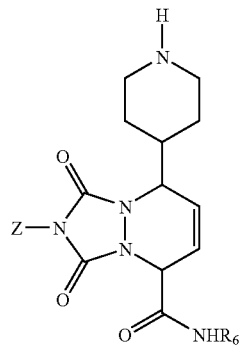

| Cpd# | Z (point of attachment at $X_1$) | $R_6$ (point of attachment at $X_5$) | $[M + H]^+$ | RT | Method |
|---|---|---|---|---|---|
| 132 | 4-amidinobenzyl-NH-C(O)-(CH$_2$)$_4$-$X_1$ | $X_5$-CH$_2$-C$_6$H$_4$-CH$_2$NH$_2$ | 630.3 | 0.47(A) | D |
| 133 | piperidin-4-yl-CH$_2$-NH-C(O)-(CH$_2$)$_4$-$X_1$ | $X_5$-CH$_2$-C$_6$H$_4$-CH$_2$NH$_2$ | 595.4 | 0.14(A) | D |
| 134 | 3-(aminomethyl)benzyl-NH-C(O)-(CH$_2$)$_4$-$X_1$ | $X_5$-CH$_2$-C$_6$H$_4$-CH$_2$NH$_2$ | 617.4 | 0.14(A) | D |
| 135 | 3-aminobenzyl-NH-C(O)-(CH$_2$)$_4$-$X_1$ | $X_5$-CH$_2$-C$_6$H$_4$-CH$_2$NH$_2$ | 603.3 | 0.50(A) | D |
| 136 | 3,4-dihydroxyphenethyl-NH-C(O)-(CH$_2$)$_2$-$X_1$ | $X_5$-CH$_2$-C$_6$H$_{10}$-NH$_2$ | 598.3 | 0.53(A) | D |

TABLE 4-continued

REPRESENTATIVE COMPOUNDS

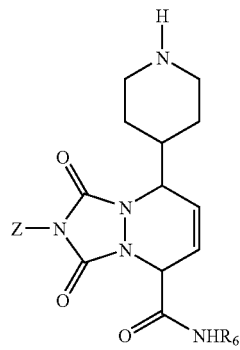

| Cpd# | Z (point of attachment at $X_1$) | $R_6$ (point of attachment at $X_5$) | $[M + H]^+$ | RT | Method |
|---|---|---|---|---|---|
| 137 | H₂N–(m-C₆H₄)–CH₂–NH–C(O)–CH₂CH₂CH₂–$X_1$ | $X_5$–CH₂–(p-C₆H₄)–CH₂–NH₂ | 595.4 | 0.13(A) | D |
| 138 | 4-F,3-CF₃–C₆H₃–CH₂–NH–C(O)–CH₂CH₂CH₂CH₂–$X_1$ | $X_5$–CH₂–(p-C₆H₄)–CH₂–NH₂ | 666.3 | 0.92(A) | D |

Example 7

Tryptase Antagonism Assay of Representative Compounds

Tryptase inhibition assay was performed at room temperature in 96-well microplates using a Bio-Rad Model 3550 (Bio-Rad Laboratories, Inc., Cambridge, Mass.), Spectro-Max (Molecular Devices, Model 250, Sunnyvale, Calif.) or Fluoroskan Ascent fluorescence (Labsystems, Inc., Helsinki, Finland) plate reader. Either 1 mM solutions of test compounds in water or 10 mM solutions of test compounds in DMSO served as the stock solutions for each inhibition assay. For this assay, the release of pNA from the chromogenic substrate S-2366, L-pyroGlu-Pro-Arg-pNA (Km=242 μM) (diaPharma, West Chester, Ohio) was monitored at 405 nm. The reaction progress curves were recorded by reading the plates, typically 80 times with 24 s intervals. The general format of the assays are as follows: 100 μl of an inhibitor solution and 50 μl of enzyme solution were placed in a microplate well, incubated at room temperature for 30 min, and then 100 μl of substrate solution was added to initiate the reaction. In the tryptase assay, 0.2 nM human lung tryptase (Elastin Products Company, Inc., Owensville, Mo.) and 200 μM S-2366 were used in Tris buffer, pH 8.0. Initial rates were determined by unweighted nonlinear least-squares fitting to a first-order reaction in either GraFit (Erithacus Software Ltd., London, UK) or GraphPad Prism (GraphPad Software, Inc., San Diego, Calif.). The determined initial velocities were then nonlinear least-squares fitted against the concentrations of a tested compound using either GraFit or GraphPad Prism to obtain Ki.

Preferably, the compounds of this invention have an inhibition value of greater than 70% at 400 ηM and/or less than Ki of 300 ηM in this assay. To this end, preferred compounds of this invention are compounds 1, 3, 6, 13, 14, 16, 20, 22, 27, 39–42, 44, 52, 57, 58, 60, 61, 64, 79, 82, 87, 123, 127, 132 and 134. As such, the compounds of this invention effectively inhibit tryptase and are effective in the treatment of inflammatory related diseases.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:
1. A compound having the structure:

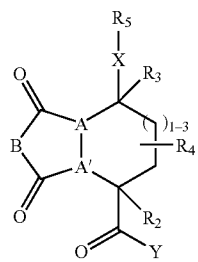

or a pharmaceutically acceptable salt or stereoisomer thereof,
wherein
A and A' are N;
B is —N(Z)-;
X is a substituted or unsubstituted divalent heterocycle,
  wherein a substituted moiety has at least one hydrogen atom replaced by halogen oxo, hydroxy, haloalkyl —R, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —NRSO$_2$R, —Si(R)$_3$, or —OP(OR)$_3$,
  wherein each occurrence of R is the same or different and independently hydrogen, alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocycle or a substituted heterocycle;
Y is selected from the group consisting of:
(i) any amino acid, peptide, protein, or amino acid side chain moiety;
(ii) any moiety selected from the group consisting of substituted or unsubstituted alkyl, aryl, arylalkyl, heterocycle, heterocyclealkyl, heteroaryl and heteroarylalkyl moieties
  wherein a substituted moiety has at least one hydrogen atom replaced by halogen oxo, hydroxy, haloalkyl —R, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —NRSO$_2$R, —Si(R)$_3$, or —OP(OR)$_3$,
  wherein each occurrence of R is the same or different and independently hydrogen, alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocycle or a substituted heterocycle;
(iii) the amino acid side chains of hydroxylysine, homoserine, homotyrosine, homophenylalanine, citrulline, kynurenine, 4-aminophenylalanine, 3-(2-naphthyl)-alanine, 3-(1-naphthyl) alanine, methionine sulfone, t-butyl-alanine, t-butylglycine, 4-hydroxyphenylglycine, aminoalanine, phenylglycine, vinylalanine, prop argyl-glycine, 1,2,4-triazolo-3-alanine, 4,4,4-trifluoro-threonine, thyronine, 6-hydroxytryptophan, 5-hydro-xytryptophan, 3-hydroxykynurenine, 3-aminotyrosine, trifuoromethylalanine, 2-thienylalanine, (2-(4-pyridyl)ethyl)cysteine, 3,4-dimethoxy-phenylalanine, 3,5-bistrifluoro-phenylalanine,3-(2-thiazolyl)-alanine, ibotenic acid, 1-amino-1cyclopentane-carboxylic acid, 1-amino-1cyclohexanecarboxylic acid, quisqualic acid, 3-trifluoromethylphenylalanine, 4-trifluoromethylphenylalanine, cyclohexylalanine, cyclohexylglycine, thiohistidine, 3-methoxytyrosine, elastatinal, norleucine, norvaline, alloisoleucine, homoarginine, thioproline, dehydroproline, hydroxy-proline, isonipectotic acid, homoproline, cyclohexyl-glycine, α-amino-n-butyric acid, cyclohexylalanine, aminophenylbutyric acid, phenylalanines substituted at the ortho, meta, or para position of the phenyl moiety with one or two of lower alkyl, lower alkoxy, halogen or nitro group, or substituted with a methylenedioxy group; β-2- and 3-thienylalanine, β-2- and 3-furanylalanine, β-2-, 3- and 4-pyridylalanine, β-(benzothienyl-2- and 3-yl)alanine, β-(1 and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-sulfo-tyrosine, 3-carboxy-tyrosine, 3-phospho-tyrosine, 4-methane sulfonic acid ester of tyrosine, 4-methane phosphonic acid ester of tyrosine, 3,5-diiodotyrosine, 3-nitro-tyrosine, ε-alkyl lysine and δ-alkyl ornithine;
  wherein any of these moieties may be substituted with a methyl group at the alpha, beta or gamma positions, a halogen at any aromatic residue on the amino side chain, or an appropriate protective group at the O, N, or S atoms of the side chain moieties;
(iv) peptides which are N-alkylated, N-acylated or N-sulfonylated at the amino termini, peptides in which the carboxy termini are esterified or reduced to a hydroxy or aldehyde, peptides which are N-alkylated at peptide bonds, and peptides which incorporate beta- or gamma-amino acids; and
(v) —NHR$_6$ wherein
R$_6$ is
1) —(CH$_2$)$_f$—NHR$_t$,
2) —(CH$_2$)$_f$-Het-NHR$_t$,
3) —(CH$_2$)$_o$-aryl-(CH$_2$)$_n$—R$_t$,
4) —(CH$_2$)$_o$-aryl-(CH$_2$)$_n$—NHR$_t$,
5) —(CH$_2$)$_o$-cyclohexyl-(CH$_2$)$_m$—NHR$_t$,
6) —(CH=CH)$_k$—(CH$_2$)$_p$—NHR$_t$,

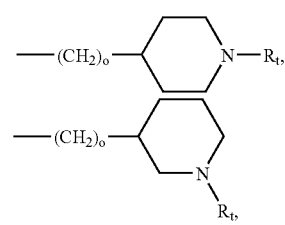

9) —(CH$_2$)$_o$— 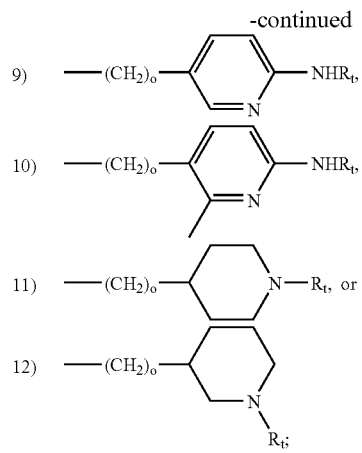

10)

11)

12)

R$_t$ is
1) hydrogen,
2) —C(=NH)—NH$_2$, or
3) a group selected from: —C(=O)O—R$_7$, —C(=O)NH—R$_7$, —S(O$_2$)—R$_7$, —C(=O)—R$_7$, and hydrogen,
wherein
R$_7$ is R$_{7a}$, R$_{7b}$, R$_{7c}$ or R$_{7d}$;
R$_{7a}$ is alkyl or aminoalkyl optionally and independently substituted with one or more substituents independently selected from R$_s$;
R$_{7b}$ is aryl, arylalkyl or Het optionally and independently substituted with one or more substituents independently selected from R$_s$;
R$_{7c}$ is phenyl, benzyl or phenethyl optionally and independently substituted with one or more substituents independently selected from R$_s$;
R$_{7d}$ is
1) —(CH$_2$)$_l$—NR$_d$R$_{d'}$,
2) —(CH$_2$)$_l$—CO$_2$R$_e$,
3) —(CH$_2$)$_m$-aryl-(CH$_2$)$_n$—NR$_d$R$_{d'}$,
4) —CH(NR$_d$R$_{d'}$)—(CH$_2$)$_o$—NR$_d$R$_{d'}$,
5) —(CH$_2$)$_m$-1,4 cyclohexyl-(CH$_2$)$_n$—NR$_d$R$_{d'}$,
6) —(CH=CH)$_k$—(CH$_2$)$_p$—NR$_d$R$_{d'}$, 7) 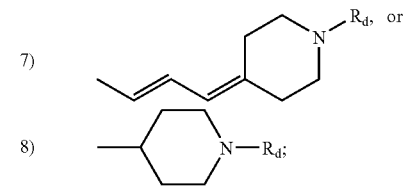

8)

R$_d$ and R$_{d'}$ are the same or different and independently selected from
1) hydrogen,
2) —C(=O)-alkyl,
3) —C(O)-alkenyl,
4) —C(O)-alkynyl,
5) —C(=O)-aryl,
6) —C(=O)-arylalkyl,
7) —C(=O)-Het,
8) a group selected from: —C(=O)O—R$_7$, —C(=O)NH—R$_7$, —S(O$_2$)—R$_7$, —C(=O)—R$_7$, and hydrogen,
9) —C(=O)-alkyl-NH$_2$, 10) —C(=O)(CH$_2$)$_m$-aryl-(CH$_2$)$_n$—NH$_2$,
11) —C(=O)(CH$_2$)$_m$-aryl-(CH$_2$)$_n$-Het,
12) —C(=O)(CH$_2$)$_m$-1,4 cyclohexyl-(CH$_2$)$_n$—NH$_2$,
13) —C(=O)(CH$_2$)$_m$-aryl-OH,
14) —C(=O)(CH$_2$)$_m$-aryl-SO$_2$—NH$_2$,
15) —C(=O)(CH$_2$)$_m$-aryl-(CH$_2$)$_n$—NHC(=O)-alkyl,
16) —C(=O)(CH$_2$)$_m$-Het,
17) —C(=O)(CH$_2$)$_m$—S-Het,
18) —SO$_2$-aryl,
19) —SO$_2$-aryloxy, and
20) —SO2-arylalkyl,
wherein alkyl, alkenyl, alkynyl, aryl, arylalkyl, aryloxy and Het are optionally and independently substituted with one or more substituents independently selected from R$_s$;
R$_e$ and R$_{e'}$ are the same or different and independently selected from
1) hydrogen,
2) alkyl,
3) alkenyl,
4) alkynyl,
5) aryl,
6) arylalkyl,
7) Het,
8) alkylaryl,
9) —(CH$_2$)$_o$-aryl-(CH$_2$)$_m$—NH$_2$,
10) —(CH$_2$)$_o$—NH-aryl,
11) —(CH$_2$)$_o$-1,4 cyclohexyl-(CH$_2$)$_m$—NH$_2$,
12) —(CH$_2$)$_o$-aryloxy,
13) —(CH$_2$)$_o$-aryl-NH$_2$, 14) 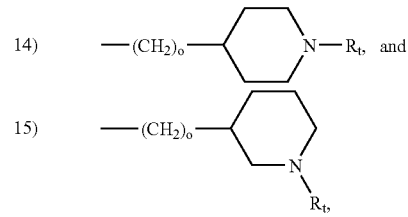 and

15)

wherein alkyl, alkenyl, alkynyl, aryl, arylalkyl and Het are optionally and independently substituted with one or more substituents independently selected from R$_s$;
R$_s$ is
1) halogen,
2) hydrogen,
3) lower alkyl
4) —CN,
5) —CF$_3$,
6) —C(=O)OR$_e$,
7) —C(=O)R$_e$,
8) —C(=NH)—NH$_2$,
9) —C(=NR$_d$)(NR$_d$R$_{d'}$),
10) —NR$_d$R$_{d'}$,
11) —NR$_e$C(=O)R$_e$,
12) —NR$_e$C(=O)OR$_e$,
13) —NR$_e$C(=O)NR$_e$R$_{e'}$,
14) —NH—C(=NH)NH$_2$,
15) —NO$_2$,
16) —OCF$_3$,
17) —OH,
18) —OR$_e$,
19) —OC(=O)R$_e$,
20) —OC(=O)NR$_e$R$_{e'}$, 21) —SR$_e$,
22) —S(O)$_k$R$_e$,
23) —S(O)$_2$OR$_e$,
24) —S(O)$_k$NR$_e$R$_{e'}$, or
25) a group selected from: —C(=O)O—R$_7$, —C(=O)NH—R$_7$, —S(O$_2$)—R$_7$, —C(=O)—R$_7$, and hydrogen;

R$_d$ and R$_{d'}$ taken together with the atoms to which they are attached form a mono- or bi-cyclic heterocyclic ring of 3 to 7 members each containing 0–3 additional heteroatoms each independently selected from nitrogen, oxygen and sulfur;

R$_e$ and R$_{e'}$ taken together with the atoms to which they are attached form a mono- or bi-cyclic heterocyclic ring of 3 to 7 members each containing 0–3 additional heteroatoms each independently selected from nitrogen, oxygen and sulfur;

k is an integer from 1 to 2;
l is an integer from 1 to 10;
m is a number from 0 to 4;
n is a number from 0 to 4;
o is an integer from 1 to 4;
p is an integer from 1 to 2; and Het is heterocycle, heterocyclealkyl, heteroaryl or heteroarylalkyl;

Z is selected from the group consisting of:
(i) any amino acid, peptide, protein, or amino acid side chain moiety;
(ii) any moiety selected from the group consisting of substituted or unsubstituted alkyl, aryl, arylalkyl, heterocycle, heterocyclealkyl, heteroaryl and heteroarylalkyl moieties
wherein a substituted moiety has at least one hydrogen atom replaced by halogen oxo, hydroxy, haloalkyl —R, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —NRSO$_2$R, —Si(R)$_3$, or —OP(OR)$_3$,
wherein each occurrence of R is the same or different and independently hydrogen, alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocycle or a substituted heterocycle;
(iii) the amino acid side chains of hydroxylysine, homoserine, homotyrosine, homophenylalanine, citrulline, kynurenine, 4-aminophenylalanine, 3-(2-naphthyl)-alanine, 3-(1-naphthyl) alanine, methionine sulfone, t-butyl-alanine, t-butylglycine, 4-hydroxyphenylglycine, aminoalanine, phenylglycine, vinylalanine, prop argyl-glycine, 1,2,4-triazolo-3-alanine, 4,4,4-trifluoro-threonine, thyronine, 6-hydroxytryptophan, 5-hydro-xytryptophan, 3-hydroxykynurenine, 3-aminotyrosine, trifuoromethylalanine, 2-thienylalanine, (2-(4-pyridyl)ethyl)cysteine, 3,4-dimethoxy-phenylalanine, 3,5-bistrifluoro-phenylalanine, 3-($_2$-thiazolyl)-alanine, ibotenic acid, 1-amino-lcyclopentane carboxylic acid, 1-amino-lcyclohexanecarboxylic acid, quisqualic acid, 3-trifluoromethylphenylalanine, 4-trifluoromethylphenylalanine, cyclohexylalanine, cyclohexylglycine, thiohistidine, 3-methoxytyrosine, elastatinal, norleucine, norvaline, alloisoleucine, homoarginine, thioproline, dehydroproline, hydroxy-proline, isonipectotic acid, homoproline, cyclohexyl-glycine, α-amino-n-butyric acid, cyclohexylalanine, aminophenylbutyric acid, phenylalanines substituted at the ortho, meta, or para position of the phenyl moiety with one or two of lower alkyl, lower alkoxy, halogen or nitro group, or substituted with a methylenedioxy group; β-2- and 3-thienylalanine, β-2- and 3-furanylalanine, β-2-, 3- and 4-pyridylalanine, β-(benzothienyl-2- and 3-yl)alanine, β-(1 and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-sulfo-tyrosine, 3-carboxy-tyrosine, 3-phospho-tyrosine, 4-methane sulfonic acid ester of tyrosine, 4-methane phosphonic acid ester of tyrosine, 3,5-diiodotyrosine, 3-nitro-tyrosine, ε-alkyl lysine and δ-alkyl ornithine;
wherein any of these moieties may be substituted with a methyl group at the alpha, beta or gamma positions, a halogen at any aromatic residue on the amino side chain, or an appropriate protective group at the O, N, or S atoms of the side chain moieties;
(iv) peptides which are N-alkylated, N-acylated or N-sulfonylated at the amino termini, peptides in which the carboxy termini are esterified or reduced to a hydroxy or aldehyde, peptides which are N-alkylated at peptide bonds, and peptides which incorporate beta- or gamma-amino acids; and
(v) any moiety selected from the group consisting of
1) hydrogen,
2) alkyl,
3) alkoxy,
4) phenyl,
5) benzyl,
6) phenethyl,
7) 1-napthylmethyl,
8) 2-napthylmethyl,
9) phenylbenzyl,
10) biphenyl,
11) aminoalkyl,
12) aryl,
13) arylalkyl,
14) Het,
15) a group selected from R$_{7d}$,
16) —(CH$_2$)$_o$—N(R$_d$R$_{d'}$),
17) —(CH$_2$)$_m$-aryl-NHR$_t$
18) —(CH$_2$)$_m$-aryl-NR$_d$R$_{d'}$,
19) —(CH$_2$)$_o$—CO$_2$R$_e$,
20) —(CH$_2$)$_o$—C(=O)—NR$_e$R$_{e'}$,
21) —(CH$_2$)$_o$—O—R$_f$,
22) —(CH$_2$)$_o$—SO$_2$-aryl, or
23) —(CH$_2$)$_o$-Het,
wherein alkyl, phenyl, benzyl, phenethyl, 1-napthylmethyl, 2-napthylmethyl, phenylbenzyl, biphenyl, aminoalkyl, aryl, arylalky and Het are optionally and independently substituted with one or more substituents independently selected from R$_s$;

R$_f$ is selected from
1) hydrogen,
2) alkyl,
3) alkenyl,
4) alkynyl,
5) aryl, 6) arylalkyl,
7) Het,
8) alkylaryl,
9) —C(O)-alkyl,
10) —C(=O)-aryl,
11) —C(=O)-arylalkyl,
12) —C(=O)-Het,
13) —C(=O)-alkylaryl,
14) —C(=O)—NH-alkyl,
15) —C(=O)—NH-aryl,
16) —C(=O)—NH-arylalkyl,
17) —C(=O)—NH-Het, and
18) —C(=O)—NH-alkylaryl;

$R_1$, $R_2$, $R_3$, $R_4$ and $R_5$ are the same or different and independently:

(a) an amino acid side chain moiety; (b) any moiety selected from the group consisting of substituted or unsubstituted alkyl, aryl, arylalkyl, heterocycle, heterocyclealkyl, heteroaryl and heteroarylalkyl moieties wherein a substituted moiety has at least one hydrogen atom replaced by halogen oxo, hydroxy, haloalkyl —R, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —NRSO$_2$R, —Si(R)$_3$, or —OP(OR)$_3$, wherein each occurrence of R is the same or different and independently hydrogen, alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocycle or a substituted heterocycle; or (c) the amino acid side chains of hydroxylysine, homoserine, homotyrosine, homophenylalanine, citrulline, kynurenine, 4-aminophenylalanine, 3-(2-naphthyl)-alanine, 3-(1-naphthyl) alanine, methionine sulfone, t-butyl-alanine, t-butylglycine, 4-hydroxyphenylglycine, aminoalanine, phenylglycine, vinylalanine, prop argyl-glycine, 1,2,4-triazolo-3-alanine, 4,4,4-trifluoro-threonine, thyronine, 6-hydroxytryptophan, 5-hydro-xytryptophan, 3-hydroxykynurenine, 3-aminotyrosine, triflioromethyl-alanine, 2-thienylalanine, (2-(4-pyridyl)ethyl)cysteine, 3,4-dimethoxy-phenylalanine, 3,5-bistrifluoro-phenylalanine,3-(2-thiazolyl)-alanine, ibotenic acid, 1-amino-lcyclopentane-carboxylic acid, 1-amino-lcyclohexanecarboxylic acid, quisqualic acid, 3-trifluoromethylphenylalanine, 4-trifluoromethylphenylalanine, cyclohexylalanine, cyclohexylglycine, thiohistidine, 3-methoxytyrosine, elastatinal, norleucine, norvaline, alloisoleucine, homoarginine, thioproline, dehydroproline, hydroxy-proline, isonipectotic acid, homoproline, cyclohexyl-glycine, α-amino-n-butyric acid, cyclohexylalanine, aminophenylbutyric acid, phenylalanines substituted at the ortho, meta, or para position of the phenyl moiety with one or two of lower alkyl, lower alkoxy, halogen or nitro group, or substituted with a methylenedioxy group; β-2- and 3-thienylalanine, β-2- and 3-furanylalanine, β-2-, 3- and 4-pyridylalanine, β-(benzothienyl-2- and 3-yl)alanine, β-(1 and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-sulfo-tyrosine, 3-carboxy-tyrosine, 3-phospho-tyrosine, 4-methane sulfonic acid ester of tyrosine, 4-methane phosphonic acid ester of tyrosine, 3,5-diiodotyrosine, 3-nitro-tyrosine, ε-alkyl lysine and δ-alkyl ornithine;

wherein any of these moieties may be substituted with a methyl group at the alpha, beta or gamma positions, a halogen at any aromatic residue on the amino side chain, or an appropriate protective group at the O, N, or S atoms of the side chain moieties; and any two adjacent CH groups of the fused bicyclo compound optionally form a double bond.

2. The compound according to claim 1 wherein $R_2$ is hydrogen.

3. The compound according to claim 2 wherein $R_3$ is hydrogen.

4. The compound according to claim 1 having the structure:

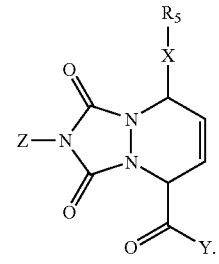

5. The compound according to claim 4 having the structure:

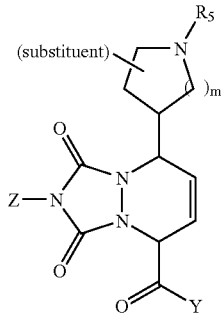

wherein
m is 1, 2, 3, or 4;
the substitutent is halogen oxo, hydroxy, haloalkyl —R, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —NRSO$_2$R, —Si(R)$_3$, or —OP(OR)$_3$, wherein each occurrence of R is the same or different and independently hydrogen, alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocycle or a substituted heterocycle; and $R_5$, taken together with the substitutent, may optionally form a substituted or unsubstituted heterocycle.

6. The compound according to claim 5 having the structure:

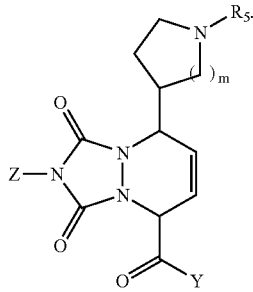

7. The compound according to claim 6 having the structure:

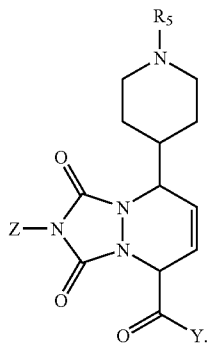

8. The compound according to claim 7 wherein Y and Z are the same or different and independently an amino acid side chain moiety or an amino acid side chain derivative.

9. The compound according to claim 5 wherein
Y is —$NHR_6$;
$R_6$ is
1) —$(CH_2)_f$—$NHR_t$,
2) —$(CH_2)_f$-Het-$NHR_t$,
3) —$(CH_2)_o$-aryl—$(CH_2)_n$—$R_t$,
4) —$(CH_2)_o$-aryl—$(CH_2)_n$—$NHR_t$,
5) —$(CH_2)_o$-cyclohexyl—$(CH_2)_m$—$NHR_t$,
6) —$(CH=CH)_k$—$(CH_2)_p$—$NHR_t$, 7) 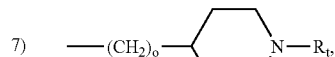

8) 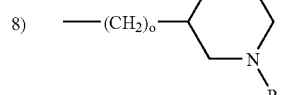

9) 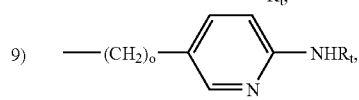

10) 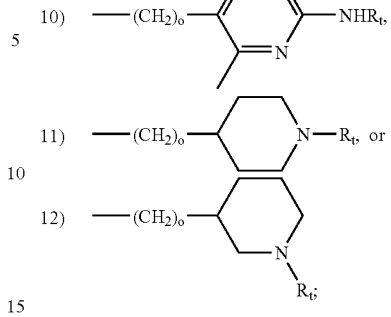

11) —$(CH_2)_o$-[piperidine]-$R_t$, or

12) —$(CH_2)_o$-[tetrahydropyridine]-$R_t$;

$R_t$ is
1) hydrogen,
2) —C(=NH)—$NH_2$, or
3) a group selected from: —C(=O)O—$R_7$, —C(=O)NH—$R_7$, —S(O_2)—$R_7$, —C(=O)—$R_7$, and hydrogen, wherein
$R_7$ is $R_{7a}$, $R_{7b}$, $R_{7c}$ or $R_{7d}$;
$R_{7a}$ is alkyl or aminoalkyl optionally and independently substituted with one or more substituents independently selected from $R_s$;
$R_{7b}$ is aryl, arylalkyl or Het optionally and independently substituted with one or more substituents independently selected from $R_s$;
$R_{7c}$ is phenyl, benzyl or phenethyl optionally and independently substituted with one or more substituents independently selected from $R_s$;
$R_{7d}$ is
1) —$(CH_2)_f$—$NR_dR_{d'}$,
2) —$(CH_2)_f$—$CO_2R_e$,
3) —$(CH_2)_m$-aryl-$(CH_2)_n$—$NR_dR_{d'}$,
4) —$CH(NR_dR_{d'})$—$(CH_2)_o$—$NR_dR_{d'}$,
5) —$(CH_2)_m$-1,4 cyclohexyl-$(CH_2)_n$—$NR_dR_{d'}$,
6) —$(CH=CH)_k$—$(CH_2)_p$—$NR_dR_{d'}$, 7) 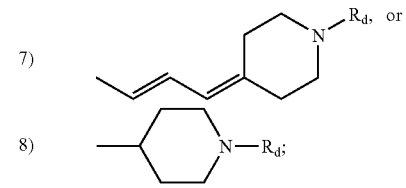

8) [piperidine]-$R_d$;

$R_d$ and $R_{d'}$ are the same or different and independently selected from
1) hydrogen,
2) —C(=O)-alkyl,
3) —C(=O)-alkenyl,
4) —C(=O)-alkynyl,
5) —C(=O)-aryl,
6) —C(=O)-arylalkyl,
7) —C(=O)-Het,
8) a group selected from: —C(=O)O—$R_7$, —C(=O)NH—$R_7$, —S(O_2)—$R_7$, —C(O)—$R_7$, and hydrogen,
9) —C(=O)-alkyl-$NH_2$,
10) —C(=O)$(CH_2)_m$-aryl-$(CH_2)_n NH_2$,
11) —C(=O)$(CH_2)_m$-aryl-$(CH_2)_n$-Het,
12) —C(=O)$(CH_2)_m$-1,4 cyclohexyl-$(CH_2)_n$—$NH_2$, 13) —C(=O)(CH$_2$)$_m$-aryl-OH,
14) —C(=O)(CH$_2$)$_m$-aryl-SO$_2$—NH$_2$,
15) —C(=O)(CH$_2$)$_m$-aryl—(CH$_2$)$_n$—NHC(=O)-alkyl,
16) —C(=O)(CH$_2$)$_m$-Het,
17) —C(=O)(CH$_2$)$_m$—S-Het,
18) —SO$_2$-aryl,
19) —SO$_2$-aryloxy, and
20) —SO2-arylalkyl,
wherein alkyl, alkenyl, alkynyl, aryl, arylalkyl, aryloxy and Het are optionally and independently substituted with one or more substituents independently selected from R$_s$;
R$_e$ and R$_{e'}$ are the same or different and independently selected from
1) hydrogen,
2) alkyl,
3) alkenyl,
4) alkynyl,
5) aryl,
6) arylalkyl,
7) Het,
8) alkylaryl,
9) —(CH$_2$)$_o$-aryl-(CH$_2$)$_m$—NH$_2$,
10) —(CH$_2$)$_o$—NH-aryl,
11) —(CH$_2$)$_o$-1,4 cyclohexyl-(CH$_2$)$_m$—NH$_2$,
12) —(CH$_2$)$_o$-aryloxy,
13) —(CH$_2$)$_o$-aryl-NH$_2$,

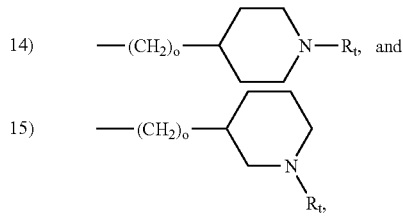

14) —(CH$_2$)$_o$— [piperidine]—N—R$_t$, and
15) —(CH$_2$)$_o$— [piperidine N-R$_t$], wherein alkyl, alkenyl, alkynyl, aryl, arylalkyl and Het are optionally and independently substituted with one or more substituents independently selected from R$_s$;
R$_s$ is
1) halogen,
2) hydrogen,
3) lower alkyl
4) —CN,
5) —CF$_3$,
6) —C(=O)OR$_e$,
7) —C(=O)R$_e$,
8) —C(=NH)—NH$_2$,
9) —C(=NR$_d$)(NR$_d$R$_{d'}$),
10) —NR$_d$R$_{d'}$,
11) —NR$_e$C(=O)R$_e$,
12) —NR$_e$C(=O)OR$_e$,
13) —NR$_e$C(=O)NR$_e$R$_{e'}$,
14) —NH—C(=NH)NH$_2$,
15) —NO$_2$,
16) —OCF$_3$,
17) —OH,
18) —OR$_e$,
19) —OC(=O)R$_e$,
20) —OC(=O)NR$_e$R$_{e'}$,
21) —SR$_e$,
22) —S(O)$_k$R$_e$,
23) —S(O)$_2$OR$_e$,
24) —S(O)$_k$NR$_e$R$_{e'}$, or
25) a group selected from: —C(=O)O—R$_7$, —C(=O)NH—R$_7$, —S(O$_2$)—R$_7$, —C(=O)—R$_7$, and hydrogen;
R$_d$ and R$_{d'}$ taken together with the atoms to which they are attached form a mono- or bi-cyclic heterocyclic ring of 3 to 7 members each containing 0–3 additional heteroatoms each independently selected from nitrogen, oxygen and sulfur;
R$_e$ and R$_{e'}$ taken together with the atoms to which they are attached form a mono- or bi-cyclic heterocyclic ring of 3 to 7 members each containing 0–3 additional heteroatoms each independently selected from nitrogen, oxygen and sulfur;
k is an integer from 1 to 2;
l is an integer from 1 to 10;
m is a number from 0 to 4;
n is a number from 0 to 4;
o is an integer from 1 to 4;
p is an integer from 1 to 2; and
Het is heterocycle, heterocyclealkyl, heteroaryl or heteroarylalkyl.

10. The compound of claim 9,
wherein
Z is
1) hydrogen,
2) alkyl,
3) alkoxy,
4) phenyl,
5) benzyl,
6) phenethyl,
7) 1-napthylmethyl,
8) 2-napthylmethyl,
9) phenylbenzyl,
10) biphenyl,
11) aminoalkyl,
12) aryl,
13) arylalkyl,
14) Het,
15) a group selected from R$_{7d}$,
16) —(CH$_2$)$_o$—N(R$_d$R$_{d'}$),
17) —(CH$_2$)$_m$-aryl-NHR$_t$,
18) —(CH$_2$)$_m$-aryl-NR$_d$R$_{d'}$,
19) —(CH$_2$)$_o$—CO$_2$R$_e$,
20) —(CH$_2$)$_o$—C(=O)—NR$_e$R$_{e'}$,
21) —(CH$_2$)$_o$—O—R$_f$,
22) —(CH$_2$)$_o$—SO$_2$-aryl, or
23) —(CH$_2$)$_o$-Het,
wherein alkyl, phenyl, benzyl, phenethyl, 1-napthylmethyl, 2-napthylmethyl, phenylbenzyl, biphenyl, aminoalkyl, aryl, arylalky and Het are optionally and independently substituted with one or more substituents independently selected from R$_s$;

$R_f$ is selected from
1) hydrogen,
2) alkyl,
3) alkenyl,
4) alkynyl,
5) aryl,
6) arylalkyl,
7) Het,
8) alkylaryl,
9) —C(O)-alkyl,
10) —C(=O)-aryl,
11) —C(=O)-arylalkyl,
12) —C(=O)-Het,
13) —C(=O)-alkylaryl,
14) —C(=O)—NH-alkyl,
15) —C(=O)—NH-aryl,
16) —C(=O)—NH-arylalkyl,
17) —C(=O)—NH-Het, and
18) —C(=O)—NH-alkylaryl.

11. The compound according to claim 1 having the following conformation:

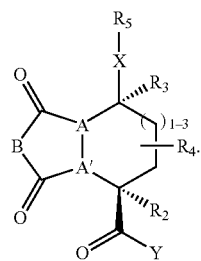

12. The compound according to claim 1 having the following conformation:

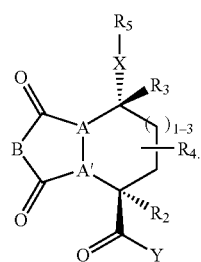

13. The compound according to claim 1 having the following conformation:

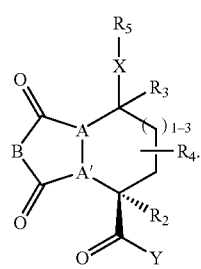

14. The compound according to claim 1 having the following conformation:

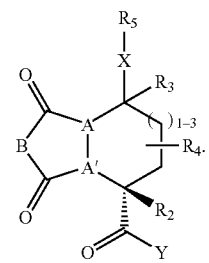

15. The compound according to claim 1 having the following conformation:

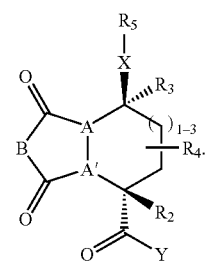

16. The compound according to claim 1 having the following conformation:

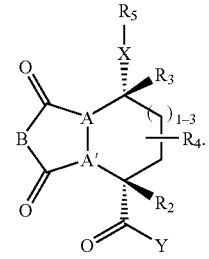

17. The compound according to claim 7 wherein Y and Z are the same or different and independently a substituted or unsubstituted alkyl, aryl, arylalkyl, heterocycle, heterocyclealkyl, heteroaryl or heteroarylalkyl, wherein a substituted moiety has at least one hydrogen atom replaced by halogen oxo, hydroxy, haloalkyl —R, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO$_2$R, —NRSO$_2$R, —Si(R)$_3$, or —OP(=OR)$_3$, wherein each occurrence of R is the same or different and independently hydrogen, alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocycle or a substituted heterocycle.

18. The compound according to claim 7 having the structure
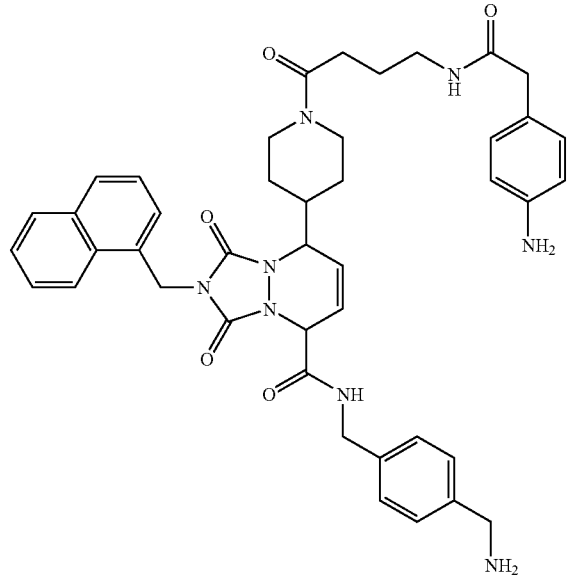
19. The compound according to claim 7 having the structure
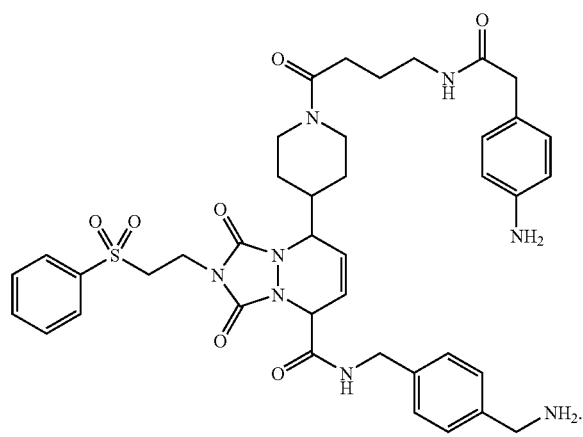
20. The compound according to claim 7 having the structure
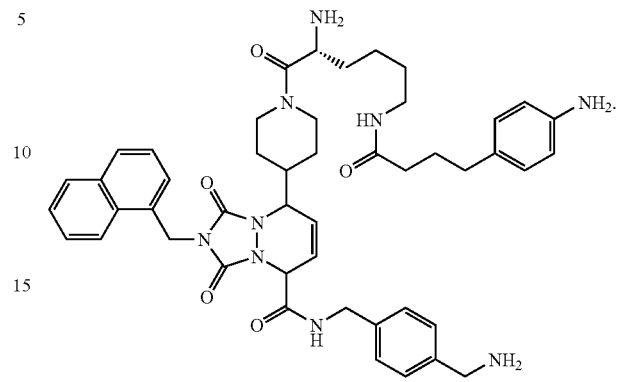
21. The compound according to claim 7 having the structure
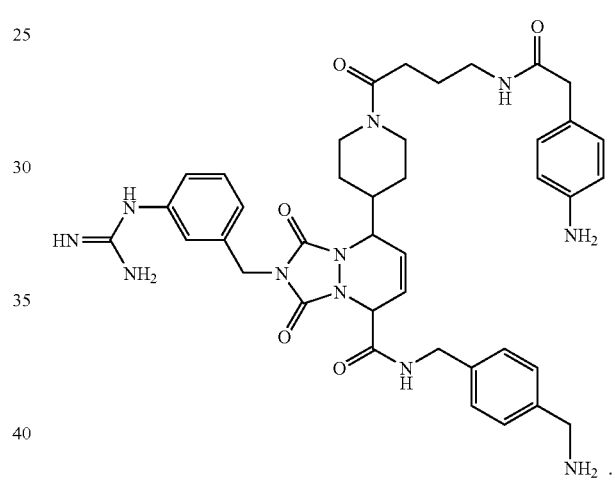
22. The compound according to claim 7 having the structure
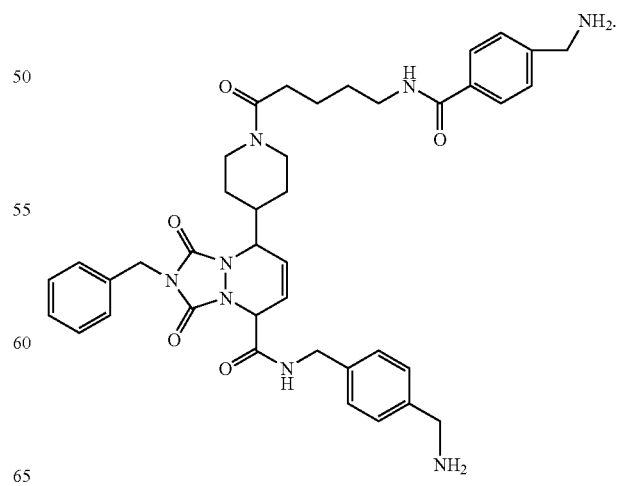

23. The compound according to claim 7 having the structure

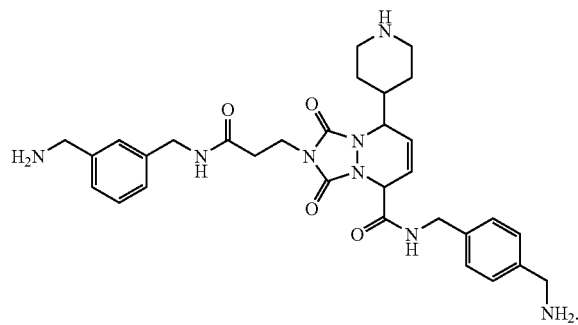

24. The compound according to claim 9 wherein m is 2 and the substituent is a hydrogen atom.

25. The compound according to claim 10 wherein m is 2 and the substituent is a hydrogen atom.

26. The compound according to claim 10 wherein the compound is
  (i) N-{4-[(acetoxyamino)methyl]benzyl}-8-{1-[4-({[4-(acetylamino)phenyl]acetyl}amino)butanoyl]-4-piperidinyl}-2-(1-naphthylmethyl)-1,3-dioxo-2,3,5,8-tetrahydo-1H-[1,2,4]triazolo[1,2-a]pyridazine-5-carboxamide;
  (ii) N-[4-(aminomethyl)benzyl]-8-[1-(4-{[4-aminophenyl)acetyl]amino}butanoyl)-4-piperidinyl]-2-(1-naphthylmethyl)-1,3-dioxohexahydro-1H-[1,2,4]triazolo[1,2-a]pyridazine-5-carboxamide; or
  (iii) N-[4-(aminomethyl)benzyl]-8-[1-(4-{[4-aminophenyl)acetyl]amino}butanoyl)-4-piperidinyl]-2-(1-naphthylmethyl)-1,3-dioxo-2,3,7,8-tetrahydo-1H-[1,2,4]triazolo[1,2-a]pyridazine-5-carboxamide.

27. A library of compounds comprising a plurality of library members, wherein at least one library member is a compound of claim 1.

28. A composition comprising a compound of claim 1 and a pharmaceutically acceptable carrier.

29. A method for treating allergic airway inflammation, comprising administering to a warm-blooded animal in need thereof an effective amount of the composition of claim 28.

30. A method of treating asthma or ulcerative colitis, comprising administering to a mammal in need of such treatment an amount of the composition of claim 28 effective in treating such condition.

* * * * *

UNITED STATES PATENT AND TRADEMARK OFFICE
CERTIFICATE OF CORRECTION

PATENT NO. : 7,053,214 B2
APPLICATION NO. : 10/367575
DATED : May 30, 2006
INVENTOR(S) : Ogbu et al.

It is certified that error appears in the above-identified patent and that said Letters Patent is hereby corrected as shown below:

Column 151, line 4, the right-hand formula should appear as follows:
--9) –C(=0)-alkyl,--

Column 151, line 48, please change "triflioromethyl-alanine" to --trifuoromethyl-alanine--.

Column 154, line 62, please change "–C(0)–$R_7$" to -- –C(=0)–$R_7$--.

Column 157, line 10, the right-hand formula should appear as follows:
--9) –C(=0)-alkyl,--

Column 161, line 22, for the claim reference numeral "10" should read --1--.

Signed and Sealed this

Tenth Day of April, 2007

JON W. DUDAS
*Director of the United States Patent and Trademark Office*